(12) United States Patent
Kahn

(10) Patent No.: US 9,374,394 B2
(45) Date of Patent: *Jun. 21, 2016

(54) METHODS AND SYSTEMS FOR ONLINE COUNSELING SESSIONS AND CLINICS

(71) Applicant: Justin Kahn, Salt Lake City, UT (US)

(72) Inventor: Justin Kahn, Salt Lake City, UT (US)

(*) Notice: Subject to any disclaimer, the term of this patent is extended or adjusted under 35 U.S.C. 154(b) by 186 days.

This patent is subject to a terminal disclaimer.

(21) Appl. No.: 14/259,027

(22) Filed: Apr. 22, 2014

(65) Prior Publication Data

US 2014/0229547 A1     Aug. 14, 2014

Related U.S. Application Data

(63) Continuation-in-part of application No. 13/372,365, filed on Feb. 13, 2012, now Pat. No. 8,718,245.

(60) Provisional application No. 61/443,657, filed on Feb. 16, 2011, provisional application No. 61/545,992, filed on Oct. 11, 2011.

(51) Int. Cl.
*H04N 7/14*     (2006.01)
*H04L 29/06*    (2006.01)

(52) U.S. Cl.
CPC ................... *H04L 65/4023* (2013.01)

(58) Field of Classification Search
USPC .............. 348/14.01, 14.08, 14.07; 379/93.21, 379/158, 202.01
See application file for complete search history.

(56) References Cited

U.S. PATENT DOCUMENTS

2002/0029350 A1* 3/2002 Cooper et al. ................ 713/200

* cited by examiner

*Primary Examiner* — Olisa Anwah
(74) *Attorney, Agent, or Firm* — Michael F. Krieger; Kirton McConkie

(57) ABSTRACT

Methods and systems for online counseling sessions conducted over the Internet are disclosed. In some configurations, a method for remotely conducting counseling sessions between a client and an expert using an IP-based network includes providing a website accessible to the network wherein the expert and a client both have access to the website. In such configurations, upon accessing and logging into the website, the client is permitted to search a database for online experts and select an appropriate expert for a counseling session. In some configurations, the client initially completes various intake and/or registration forms in a virtual waiting room, wherein such forms are customized per the relevant expert. The method continues as an expert remotely conducts a counseling session with the client via remote means, including video conferencing. Following the counseling session, the client is automatically returned to the virtual waiting room and provided with subsequent counseling based options.

20 Claims, 77 Drawing Sheets

METHODS AND SYSTEMS FOR ONLINE COUNSELING SESSIONS AND CLINICS

RELATED APPLICATIONS

This application is a continuation-in-part of U.S. patent application Ser. No. 13/372,365 filed Feb. 13, 2012 and titled "Methods and Systems for Online Counseling Sessions and Clinics," which claims priority to U.S. Provisional Patent Application Ser. No. 61/443,657 filed Feb. 16, 2011 and titled, "Method and System for Online Psychotherapy Sessions and Clinics," and to U.S. Provisional Patent Application Ser. No. 61/545,992 filed Oct. 11, 2011 and titled, "Methods and Systems for Online Counseling Sessions and Clinics."

FIELD AND BACKGROUND

1. Field

The invention relates generally to methods and systems for conducting counseling sessions. More particularly, the invention relates to methods and systems for counseling sessions and clinics conducted remotely, such as over the Internet and/or via satellite using WIFI as well as other web-based technologies. In addition, the invention relates to methods and systems for conducting remote counseling sessions by means of various mobile devices as well as biofeedback and/or biometric devices configured to interface with an associated network and/or portal to enhance the efficacy and value of the remote counseling sessions as well as to authenticate the identity of a client.

2. Background

Counseling is a means by which people can gain valuable advice from experts. Typically, psychological, psychiatric, medical, genomic, life, business, wedding, academic, legal, or other forms of counseling, occur in an expert's office. In this setting, the expert controls the environment in which the counseling takes place. The client generally schedules an appointment with the expert and then attends the session with the expert at the appointed time. The client and the expert communicate during the counseling session, which generally may include the client conveying information to the expert about the client's needs and/or condition. The information about the client's needs and/or condition may include details of the client's experiences, feelings, history, and other extremely personal information. Upon receiving this information, the expert may then counsel the client depending on the nature of the information revealed to the expert by the client. Some experts provide set training courses to individuals in addition to or in lieu of tailored counseling sessions. Some counseling sessions occur in which there are multiple clients and/or multiple experts, which are sometimes called group counseling sessions.

SUMMARY

The invention relates generally to methods and systems for conducting counseling sessions. More particularly, the invention relates to methods and systems for counseling sessions and clinics conducted remotely, such as over the Internet and/or via satellite using WIFI as well as other web-based technologies. In addition, the invention relates to methods and systems for conducting remote counseling sessions by means of various mobile devices as well as biofeedback and/or biometric devices configured to interface with an associated network and/or portal to enhance the efficacy and value of the remote counseling sessions.

Accordingly, methods and systems for online counseling sessions conducted over the Internet are disclosed. In some configurations, a method for remotely conducting counseling sessions between a client and an expert using an IP-based network includes providing a website accessible to the network wherein the expert and a client both have access to the website. In such configurations, upon accessing and logging into the website, the client is permitted to search a database for online experts and select an appropriate expert for a counseling session. In some configurations, the client initially completes various intake and/or registration forms in a virtual waiting room, wherein such forms are customized per the relevant expert. The method continues as an expert remotely conducts a counseling session with the client via remote means, including video conferencing. Following the counseling session, the client is automatically returned to the virtual waiting room and provided with subsequent counseling based options.

In some configurations, the methods of the present invention are directed to expert marketing capabilities and/or strategies. In other configurations, the methods of the present invention are directed to client scheduling or calendaring for counseling sessions, including synchronization with Outlook™, Gmail™, iCal™ or other electronic and/or web-based calendaring systems or programs. In still other configurations, email, text, SMS messaging, instant messaging and the like are employed to confirm appointments and/or provide reminders of upcoming appointments, to customize general information presented to individual clients, to secure client access to personalized reports and documentation generated by the expert which, in some configurations, are accessible to individual client and expert only, to provide access to products for purchase selected by the expert for the client, to provide a full accounting and payment system for experts as well as clients, to facilitate client rating and feedback on the expert relative to services rendered or previously provided, and many other aspects as further disclosed herein.

In some configurations, the network and associated portal employed or used to practice various configurations of the invention may further be utilized to provide training or educational services for experts categorized by field, topic, and/or experience level. Accordingly, in various configurations, the methods and systems of the present invention provide resources for both clients seeking counseling as well as experts seeking additional education or training. In all such configurations, various forms of electronic communication can be used to supplement online counseling sessions and/or training/education such as on demand products, live webcast products, electronic documents or print products and so forth. Experts seeking to use the systems and methods of the present invention can search for and find additional training and/or educational serves from other experts available through the service in much the same way that clients seeking counseling can find specific experts in a relevant field.

Some configurations enable clients to access counseling services when and where it is most convenient for them, and increase the flexibility of counseling by offering 24-hour availability for pay-per-minute or other pay-per-view sessions. Some configurations allow experts in any stage of their practice to provide more support to existing clients and to procure new clients regardless of geographical limitations.

In some configurations, when scheduling an appointment, a client logs in to the expert's website or other type of Internet portal and accesses a scheduling calendar which displays the available counseling sessions. According to some configurations, the expert has the ability to alter the calendar so that the view is client dependent. By way of example, in some embodiments the calendar may be manipulated so that fewer "available" counseling sessions are displayed for these clients. In some configurations, one or more discrete or otherwise independent clinics can also employ the teachings disclosed herein to interface and/or coordinate with one another to simplify inter-office scheduling as well as streamlining other document and/or record keeping as well as a host of services that can be offered to a range of clients. In some configurations, if an expert finds himself or herself without any clients, e.g., due to cancellations, the inability of clients to travel to the office due to severe weather, etc., that expert can place an "available" icon on the homepage so that clients desiring counseling know that they can have immediate access without consulting the calendar.

In some configurations, group counseling sessions can be given. In some configurations, all clients can see the expert and the expert can see all of the clients at the same time on smaller images on one screen. In such configurations, the expert can assess the demeanor of the clients as they interact. In some configurations, the clients will be able to see each other and/or hear each other. In some configurations, online group counseling can be augmented by occasional private conversations. In some further configurations, the client or the expert may press a button sending an indication that they desire a private conversation, the expert may then excuse himself or herself from the group discussion and engage in a private conversation shielded from the view and hearing of the other group members. In some configurations, a hold type button (or a type of privacy button) is provided which allows the client to pause or temporarily suspend a particular session or to otherwise provide the client with an opportunity to put the session on hold without actually ending the session. In this way, the client has the ability to interrupt the session with respect to him or herself without affecting the session relative to other uses in order to protect the client's privacy. Specifically, the client has the ability to pause the session on his or her end so that if something in his or her environment changes, the client can control broadcasting such changes to either the expert and/or the other members of the group, or rather has control in order to avoid such a broadcast.

In various configurations, a "take the floor" feature is offered during a group counseling session. In some configurations, an expert offers a client the opportunity to lead the discussion by illuminating an icon or reference on the screen in the appropriate location. In some embodiments an "emergency" feature is offered to clients who need emergency contact information for an expert and/or an immediate counseling session with an expert.

In some configurations, an expert or other practitioner can designate an assistant who has access to the systems of the present invention, including the portal. In some configurations, for example, an assistant may be a registered nurse or a practitioner's assistant. In such configurations, the assistant is capable of meeting with and/or pre-screening clients. Such configurations further contemplate one or more, including multiple, assistants, some of whom work out of different clinics, working with any number of clients for, in connection with or on behalf of a single practitioner. In this way, one practitioner can be affiliated with multiple clinics and provide counseling or other treatment to multiple clients efficiently and effectively. In some configurations, multiple assistants associated with multiple clinics are associated with multiple practitioners. In such configurations, the assistants may have limited access to client information to preserve various privacy aspects and in some configurations the assistants must be licensed in order to provide assistance.

Additional features and advantages of the invention will be set forth in the description which follows, and in part will be apparent from the description, or may be learned by the practice of the present invention.

BRIEF DESCRIPTION OF THE DRAWINGS

In order that the manner in which the above recited and other features and advantages of the present invention are obtained, a more particular description of the invention will be rendered by reference to specific embodiments thereof, which are illustrated in the appended drawings. Understanding that the drawings depict only typical embodiments of the present invention and are not, therefore, to be considered as limiting the scope of the invention, the present invention will be described and explained with additional specificity and detail through the use of the accompanying drawings in which.

DETAILED DESCRIPTION

Figure 1:
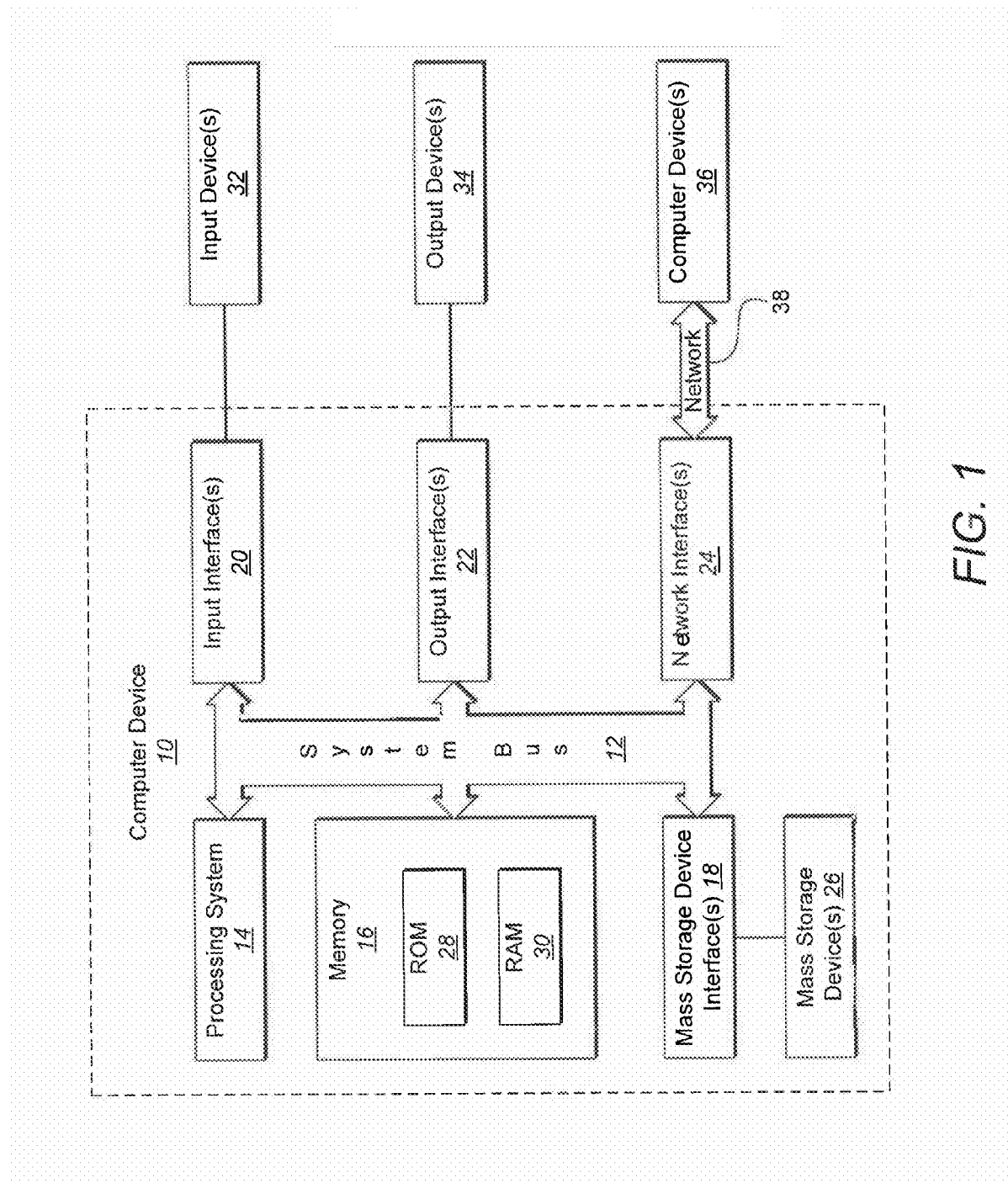
FIG. 1 illustrates a representative operating environment in which various embodiments of the present invention may be practiced.

A description of embodiments of the present invention will now be given. It is expected that the present invention may take many other forms and shapes, hence the following disclosure is intended to be illustrative and not limiting, and the scope of the invention should be determined by reference to the appended claims and their equivalents. The following description supplies specific details in order to provide a thorough understanding. Nevertheless, the skilled artisan would understand that the online counseling sessions and clinics can be implemented and used without employing these specific details. Indeed, the invention can be practiced by modifying the illustrated method and can be used in conjunction with apparatuses and/or techniques conventionally used in the industry. For example, the description focuses on providing psychotherapy counseling online. But it could be easily adapted to provide online genomics, medical, wedding, academic, veteran or other post-traumatic stress, legal or other forms of counseling wherein an expert traditionally meets with his or her clients to provide advice and or associated literature or printed materials.

In understanding the scope of the present invention, the term "configured" as used herein to describe a component, section or part of a device includes hardware and/or software that is constructed and/or programmed to carry out the desired function. In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including," "having" and their derivatives. Also, the terms "part," "section," "portion," "member" or "element" when used in the singular can have the dual meaning of a single part or a plurality of parts. Finally, terms of degree such as "substantially," "about" and "approximately" as used herein mean a reasonable amount of deviation of the modified term such that the end result is not significantly changed.

The terms "client," "patient," "employee," "recipient," etc., may be used herein. Such terms are intended to be used synonymously and refer to a user, group of users, business, and/or other entity seeking counseling or advice via the present invention.

The terms "expert," "provider," "physician," "practitioner," "contractor," "employer," "professional," etc., may be used herein. Such terms are intended to be used synonymously and refer to an individual, a group of individuals, a business, and/or other entity that provides counseling via the present invention.

Various operations may be described as multiple discrete operations in turn, in a manner that may be helpful in understanding embodiments of the present invention; however, the order of description should not be construed to imply that these operations are order dependent.

The description may use the phrases "in an embodiment," "in some embodiments," "in various embodiments," or other similar phrase, which may each refer to one or more of the same or different embodiments. Furthermore, the terms "comprising," "including," "having," and the like, as used with respect to embodiments of the present invention, are synonymous with the definition afforded the term "comprising."

The term "etc." may be used. It should be understood that the term indicates that other examples or elements are possible. The term "etc." should not be interpreted to be limited in kind, category, or similarity to the terms that precede it, but instead indicate that there are other possible examples or elements that could be given that may or may not be wholly different from the terms that precede it.

For the purposes of the present invention, the phrase "A/B" means "A or B." For the purposes of the present invention, the phrase "A and/or B" means "(A), (B), or (A and B)." For the purposes of the present invention, the phrase "at least one of A, B, and C" means "(A), (B), (C), (A and B), (A and C), (B and C), or (A, B and C)." For the purposes of the present invention, the phrase "(A)B" means "(B) or (AB)," that is, A is an optional element.

With reference now to the several drawing views, FIG. 1 and the corresponding discussion are intended to provide a general description of a suitable operating environment in which embodiments of present invention may be implemented. One skilled in the art will appreciate that some embodiments of the present invention may be practiced by or in connection with one or more computing devices and in a variety of system configurations, including in a networked configuration. However, while the methods and processes disclosed herein have proven to be particularly useful in association with a system comprising a general purpose computer, embodiments of the present invention include utilization of the methods and processes in a variety of environments, including embedded systems with general purpose processing units, digital/media signal processors (DSP/MSP), application specific integrated circuits (ASIC), stand alone electronic devices, and other such electronic environments.

Embodiments of the present invention embrace one or more computer-readable media, wherein each medium may be configured to include or includes thereon data or computer executable instructions for manipulating data. The computer executable instructions include data structures, objects, programs, routines, or other program modules that may be accessed by a processing system, such as one associated with a general-purpose computer capable of performing various different functions or one associated with a special-purpose computer capable of performing a limited number of functions. Computer executable instructions cause the processing system to perform a particular function or group of functions and are examples of program code means for implementing steps for methods disclosed herein. Furthermore, a particular sequence of the executable instructions provides an example of corresponding acts that may be used to implement such steps. Examples of computer-readable media include random-access memory ("RAM"), read-only memory ("ROM"), programmable read-only memory ("PROM"), erasable programmable read-only memory ("EPROM"), electrically erasable programmable read-only memory ("EEPROM"), compact disk read-only memory ("CD-ROM"), or any other device or component that is capable of providing data or executable instructions that may be accessed by a processing system. While embodiments of the present invention embrace the use of all types of computer-readable media, certain embodiments, as recited in the claims, may be limited to the use of tangible, non-transitory computer-readable media, and the phrases "tangible computer-readable medium" and "non-transitory computer-readable medium" (or plural variations) used herein are intended to exclude transitory propagating signals per se.

With reference to FIG. 1, a representative system for implementing embodiments of the present invention comprise computer device 10, which may be a general-purpose or special-purpose computer or any of a variety of consumer electronic devices. For example, computer device 10 may be a personal computer, a notebook computer, a netbook, a personal digital assistant ("PDA") or other hand-held device, a workstation, a minicomputer, a mainframe, a supercomputer, a multi-processor system, a network computer, a processor-based consumer electronic device, or the like.

Computer device 10 includes system bus 12, which may be configured to connect various components thereof and enables data to be exchanged between two or more components. System bus 12 may include one of a variety of bus structures including a memory bus or memory controller, a peripheral bus, or a local bus that uses any of a variety of bus architectures. Typical components connected by system bus 12 include processing system 14 and memory 16. Other components may include one or more mass storage device interfaces 18, input interfaces 20, output interfaces 22, and/or network interfaces 24, each of which will be discussed below.

Processing system 14 includes one or more processors, such as a central processor and optionally one or more other processors designed to perform a particular function or task. It is typically processing system 14 that executes the instructions provided on computer-readable media, such as on memory 16, a magnetic hard disk, a removable magnetic disk, a magnetic cassette, an optical disk, or from a communication connection, which may also be viewed as a computer-readable medium.

Memory 16 includes one or more computer-readable media that may be configured to include or includes thereon data or instructions for manipulating data, and may be accessed by processing system 14 through system bus 12. Memory 16 may include, for example, ROM 28, used to permanently store information, and/or RAM 30, used to temporarily store information. ROM 28 may include a basic input/output system ("BIOS") having one or more routines that are used to establish communication, such as during start-up of computer device 10. RAM 30 may include one or more program modules, such as one or more operating systems, application programs, and/or program data.

One or more mass storage device interfaces 18 may be used to connect one or more mass storage devices 26 to system bus 12. The mass storage devices 26 may be incorporated into or may be peripheral to computer device 10 and allow computer device 10 to retain large amounts of data. Optionally, one or more of the mass storage devices 26 may be removable from computer device 10. Examples of mass storage devices include hard disk drives, magnetic disk drives, tape drives and optical disk drives. A mass storage device 26 may read from and/or write to a magnetic hard disk, a removable magnetic disk, a magnetic cassette, an optical disk, or another computer-readable medium. Mass storage devices 26 and their corresponding computer-readable media provide nonvolatile storage of data and/or executable instructions that may include one or more program modules such as an operating system, one or more application programs, other program modules, or program data. Such executable instructions are examples of program code means for implementing steps for methods disclosed herein.

One or more input interfaces 20 may be employed to enable a user to enter data and/or instructions to computer device 10 through one or more corresponding input devices 32. Examples of such input devices include a keyboard and alternate input devices, such as a mouse, trackball, light pen, stylus, or other pointing device, a microphone, a joystick, a game pad, a satellite dish, a scanner, a camcorder, a digital camera, and the like. Similarly, examples of input interfaces 20 that may be used to connect the input devices 32 to the system bus 12 include a serial port, a parallel port, a game port, a universal serial bus ("USB"), an integrated circuit, a firewire (IEEE 1394), or another interface. For example, in some embodiments input interface 20 includes an application specific integrated circuit (ASIC) that is designed for a particular application. In a further embodiment, the ASIC is embedded and connects existing circuit building blocks.

One or more output interfaces 22 may be employed to connect one or more corresponding output devices 34 to system bus 12. Examples of output devices include a monitor or display screen, a speaker, a printer, a multi-functional peripheral, and the like. A particular output device 34 may be integrated with or peripheral to computer device 10. Examples of output interfaces include a video adapter, an audio adapter, a parallel port, and the like.

One or more network interfaces 24 enable computer device 10 to exchange information with one or more other local or remote computer devices, illustrated as computer devices 36, via a network 38 that may include hardwired and/or wireless links. Examples of network interfaces include a network adapter for connection to a local area network ("LAN") or a modem, wireless link, or other adapter for connection to a wide area network ("WAN"), such as the Internet. The network interface 24 may be incorporated with or peripheral to computer device 10. In a networked system, accessible program modules or portions thereof may be stored in a remote memory storage device. Furthermore, in a networked system computer device 10 may participate in a distributed computing environment, where functions or tasks are performed by a plurality of networked computer devices.

Those skilled in the art will appreciate that embodiments of the present invention embrace a variety of different system configurations. For example, in one embodiment the system configuration includes an output device (e.g., a multifunctional peripheral (MFP) or other printer/plotter, a copy machine, a facsimile machine, a monitor, etc.) that performs multi-colorant rendering. In another embodiment, the system configuration includes one or more client computer devices, optionally one or more server computer devices, and a connection or network communication that enables the exchange of communication to an output device, which is configured to perform multi-colorant rendering.

Figure 2:
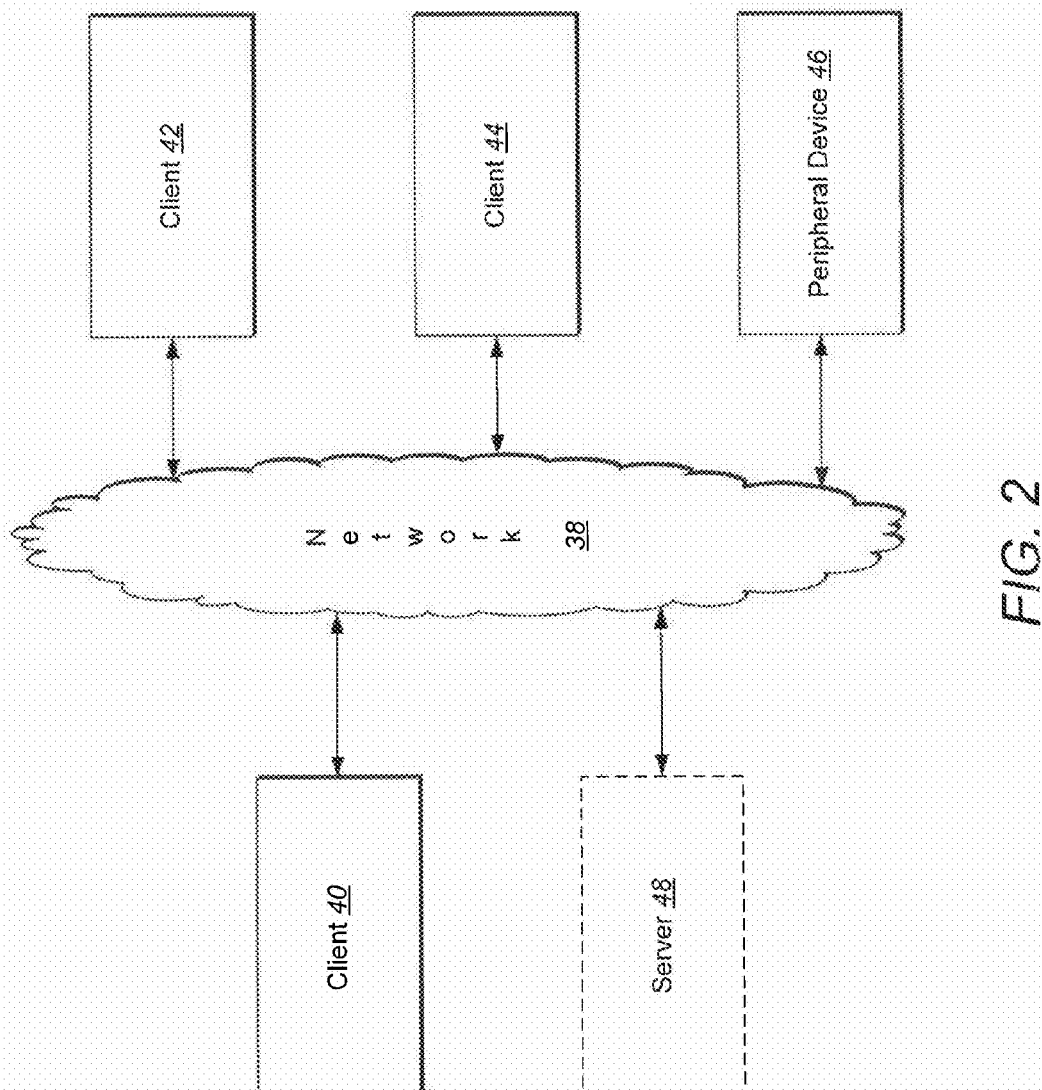
FIG. 2 illustrates a representative networked system configuration that may be used in association with embodiments of various embodiments of the present invention.

Thus, while those skilled in the art will appreciate that embodiments of the present invention may be practiced in a variety of different environments with many types of system configurations, FIG. 2 provides a representative networked system configuration that may be used in association with embodiments of the present invention. The representative system of FIG. 2 includes a computer device, illustrated as client 40, which is connected to one or more other computer devices (illustrated as client 42 and client 44) and one or more peripheral devices (illustrated as multifunctional peripheral (MFP) MFP 46) across network 38. While FIG. 2 illustrates an embodiment that includes a client 40, two additional clients, client 42 and client 44, one peripheral device, MFP 46, and optionally a server 48, which may be a print server, connected to network 38, alternative embodiments include more or fewer clients, more than one peripheral device, no peripheral devices, no server 48, and/or more than one server 48 connected to network 38. Other embodiments of the present invention include local, networked, or peer-to-peer environments where one or more computer devices may be connected to one or more local or remote peripheral devices. Moreover, embodiments in accordance with the present invention also embrace a single electronic consumer device, wireless networked environments, and/or wide area networked environments, such as the Internet.

Similarly, embodiments of the present invention embrace cloud-based architectures where one or more computer functions are performed by remote computer systems and devices at the request of a local computer device. Thus, returning to FIG. 2, the client 40 may be a computer device having a limited set of hardware and/or software resources. Because the client 40 is connected to the network 38, it may be able to access hardware and/or software resources provided across the network 38 by other computer devices and resources, such as client 42, client 44, server 48, or any other resources. The client 40 may access these resources through an access program, such as a web browser, and the results of any computer functions or resources may be delivered through the access program to the user of the client 40. In such configurations, the client 40 may be any type of computer device or electronic device discussed above or known to the world of cloud computing, including traditional desktop and laptop computers, smart phones and other smart devices, tablet computers, or any other device able to provide access to remote computing resources through an access program such as a browser.

Figure 3:
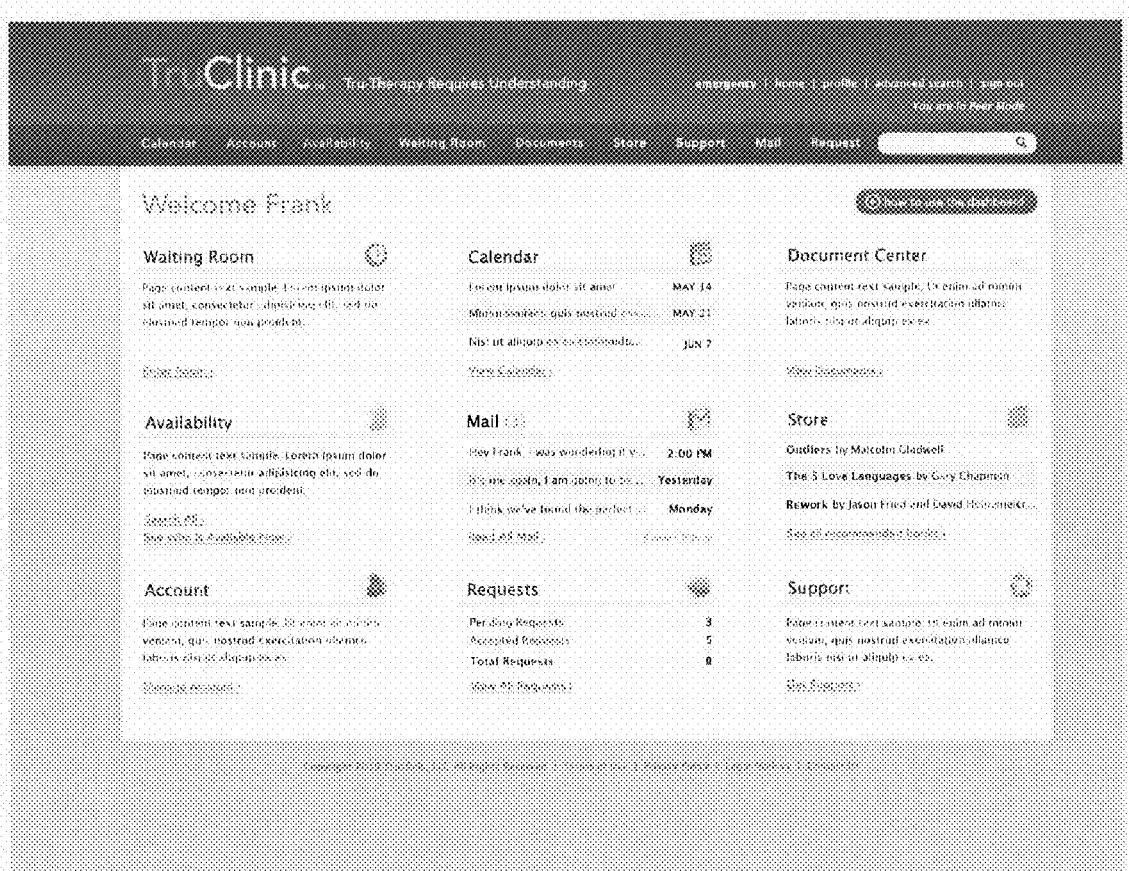
FIGS. 3-77 illustrate a collection of screen captures illustrating various features of the present invention.
Figure 4:
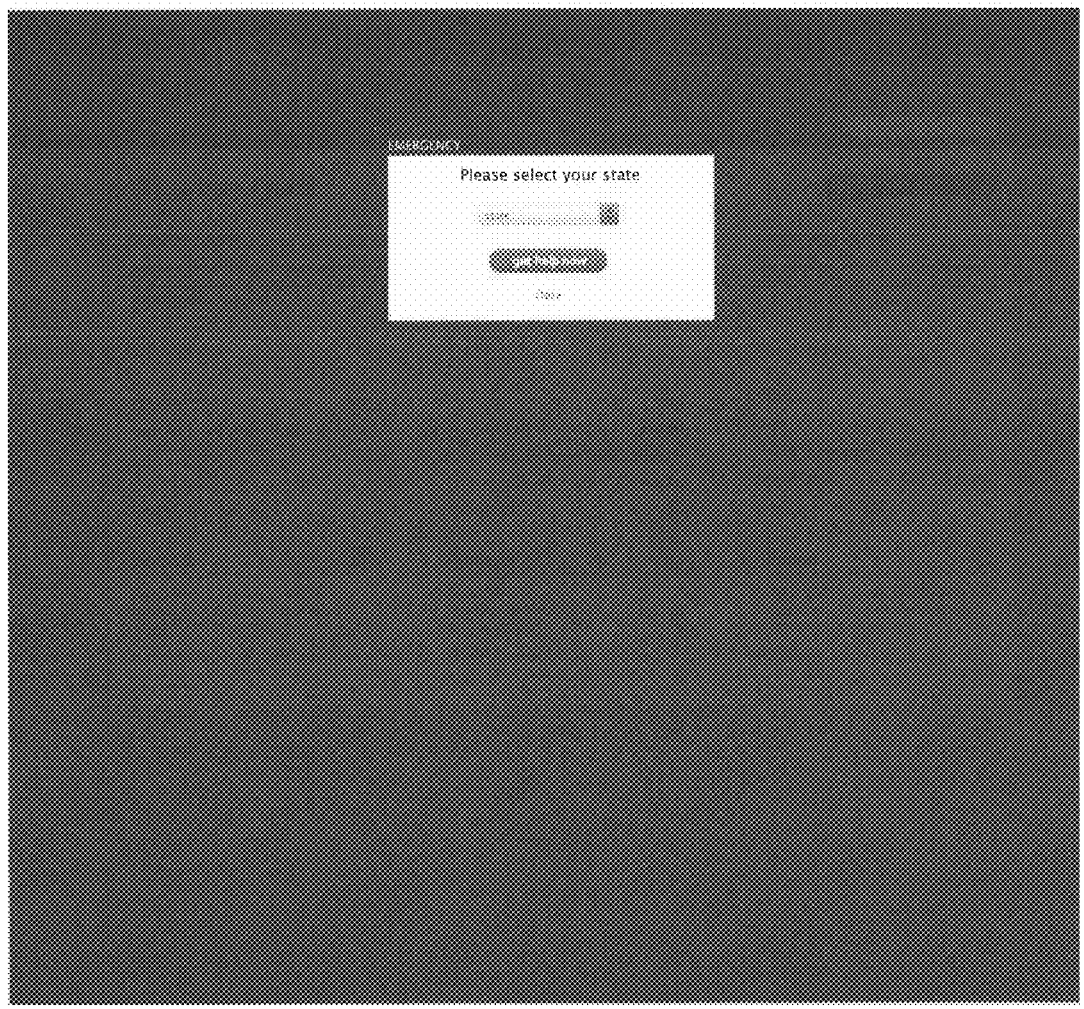
Figure 5:
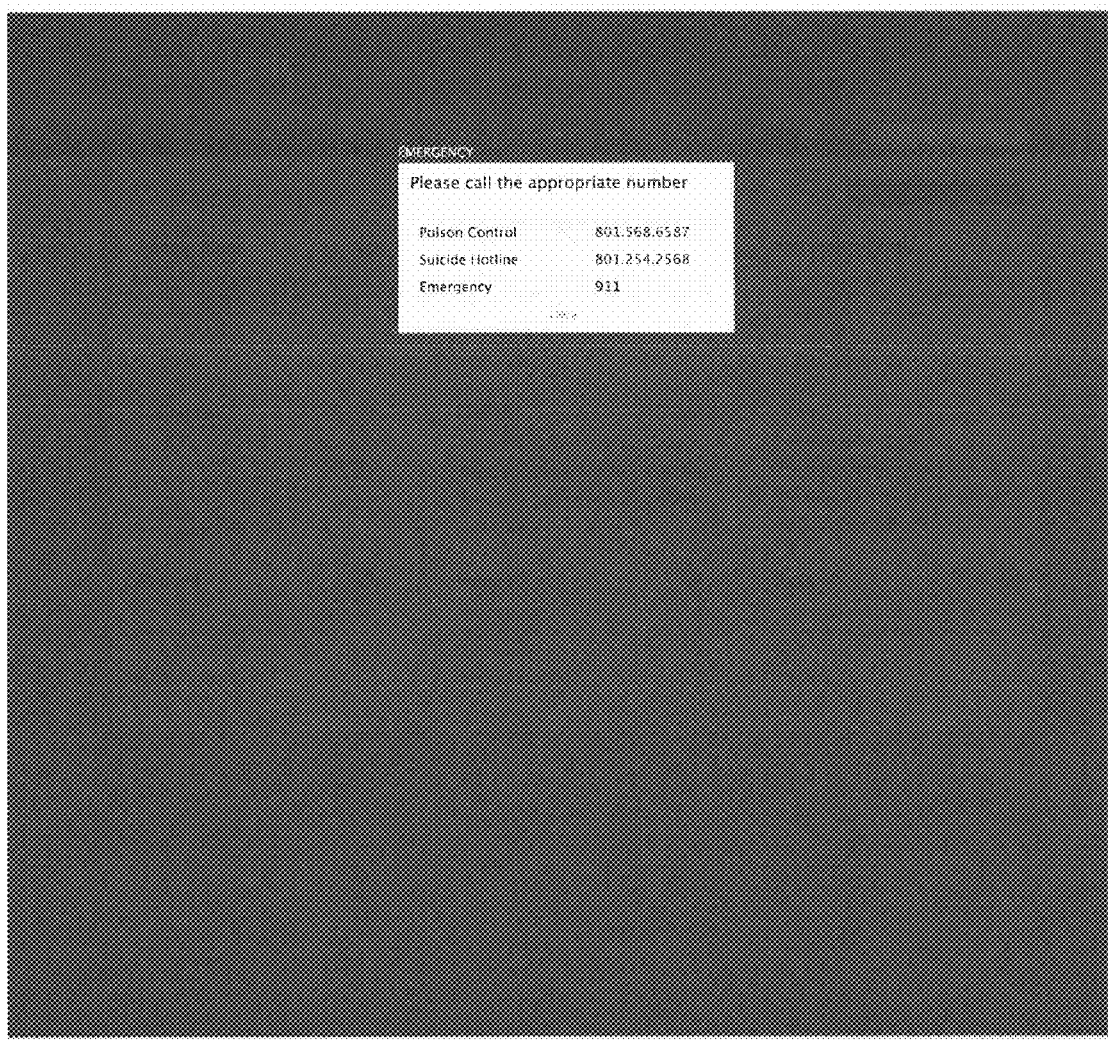
Figure 6:
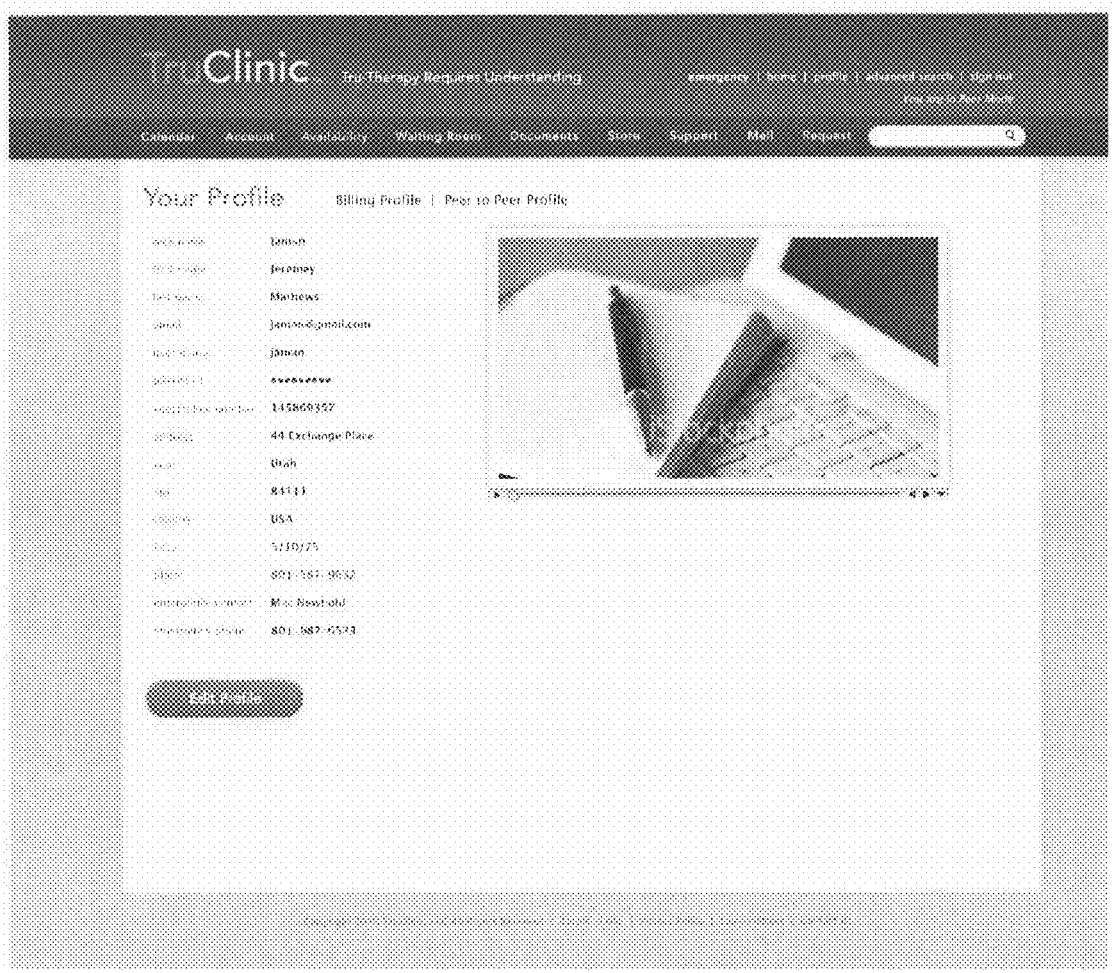
Figure 7:
Figure 8:
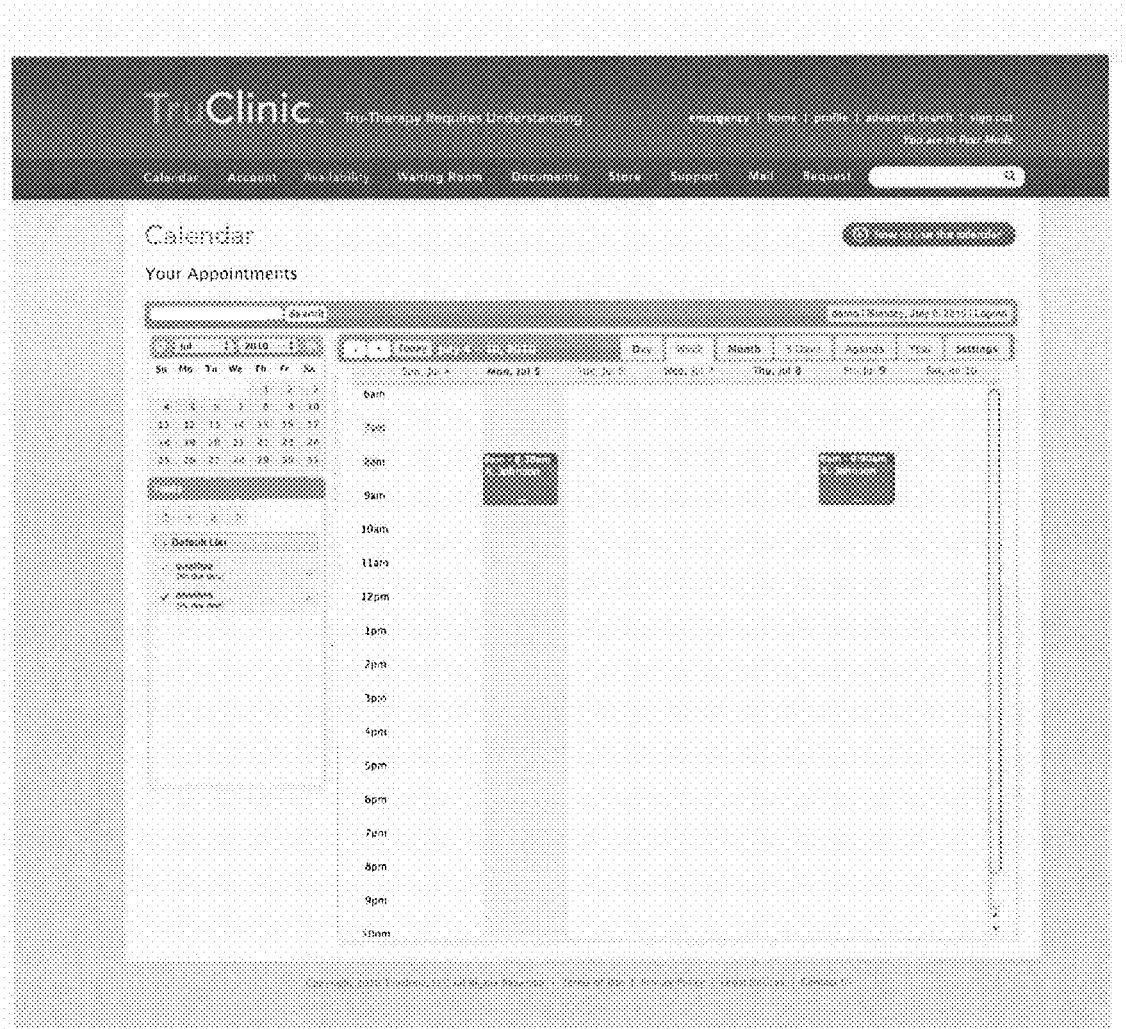
Figure 9:
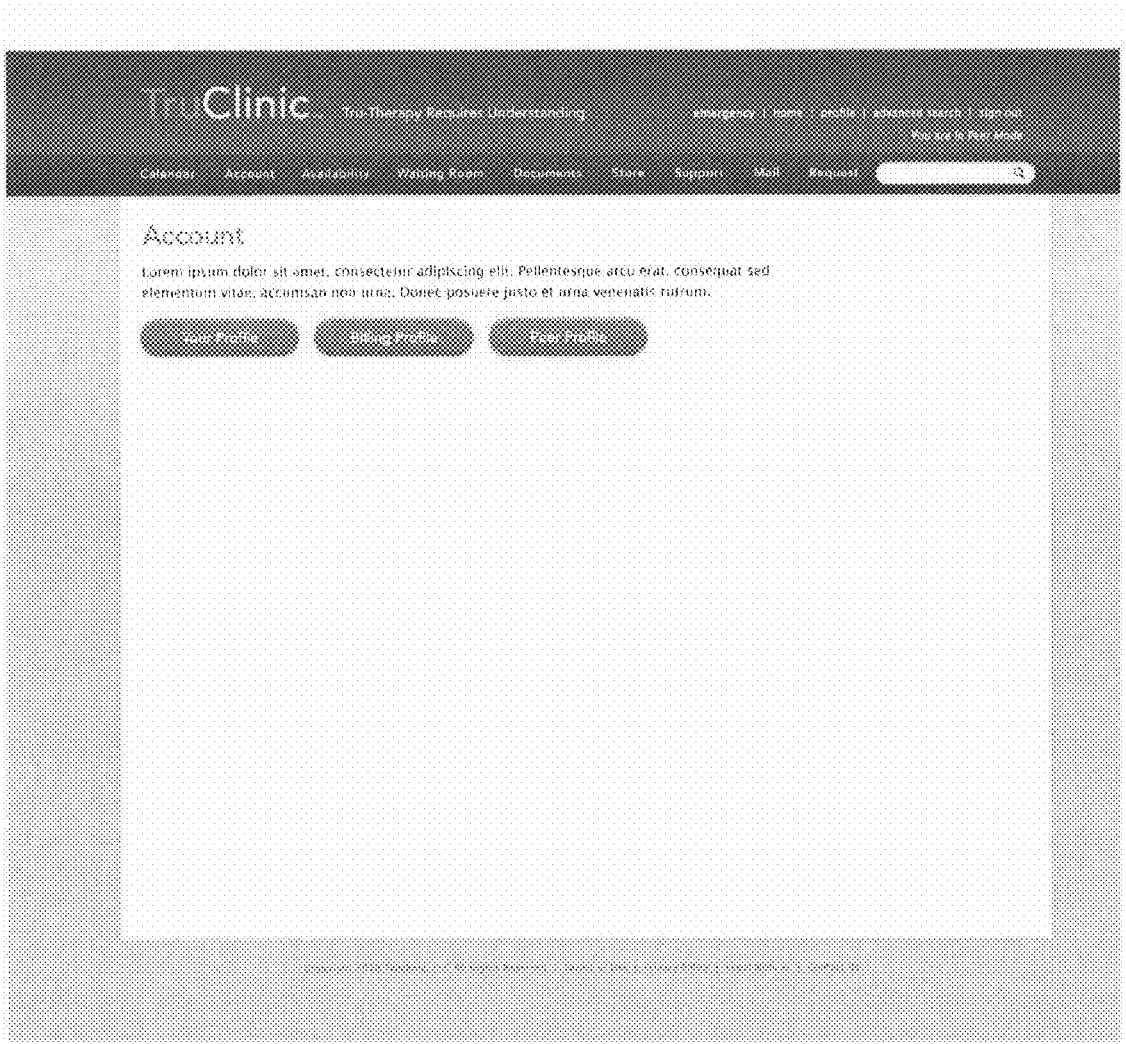
Figure 10:
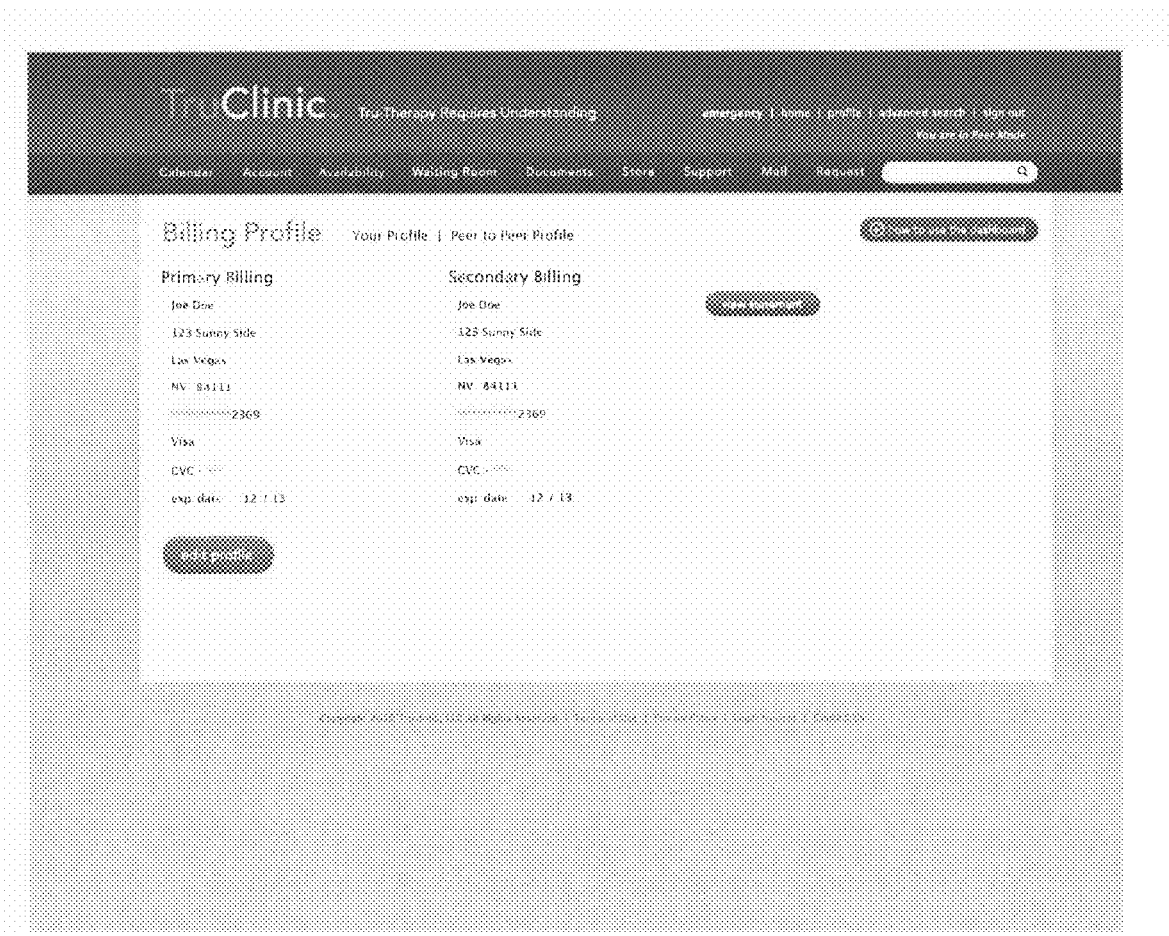
Figure 11:
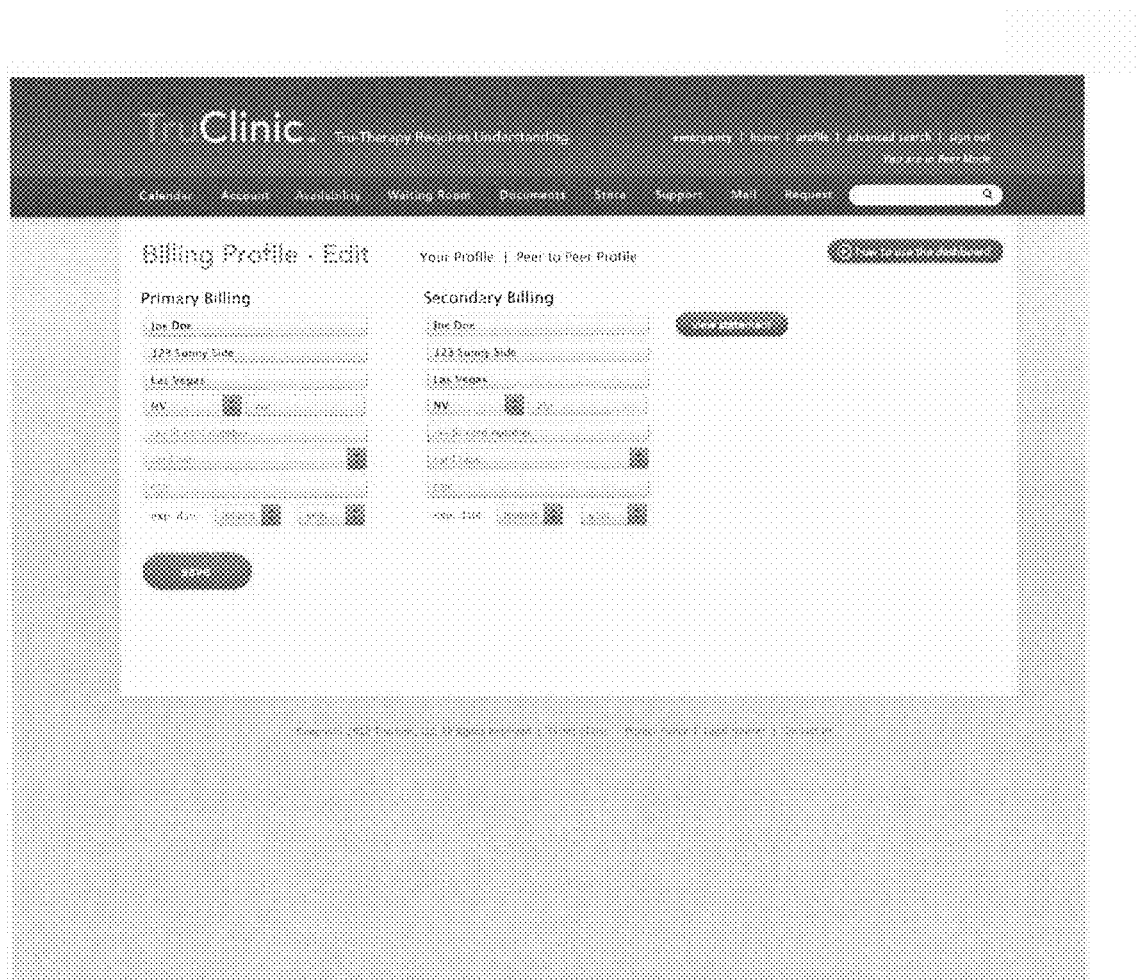
Figure 13:
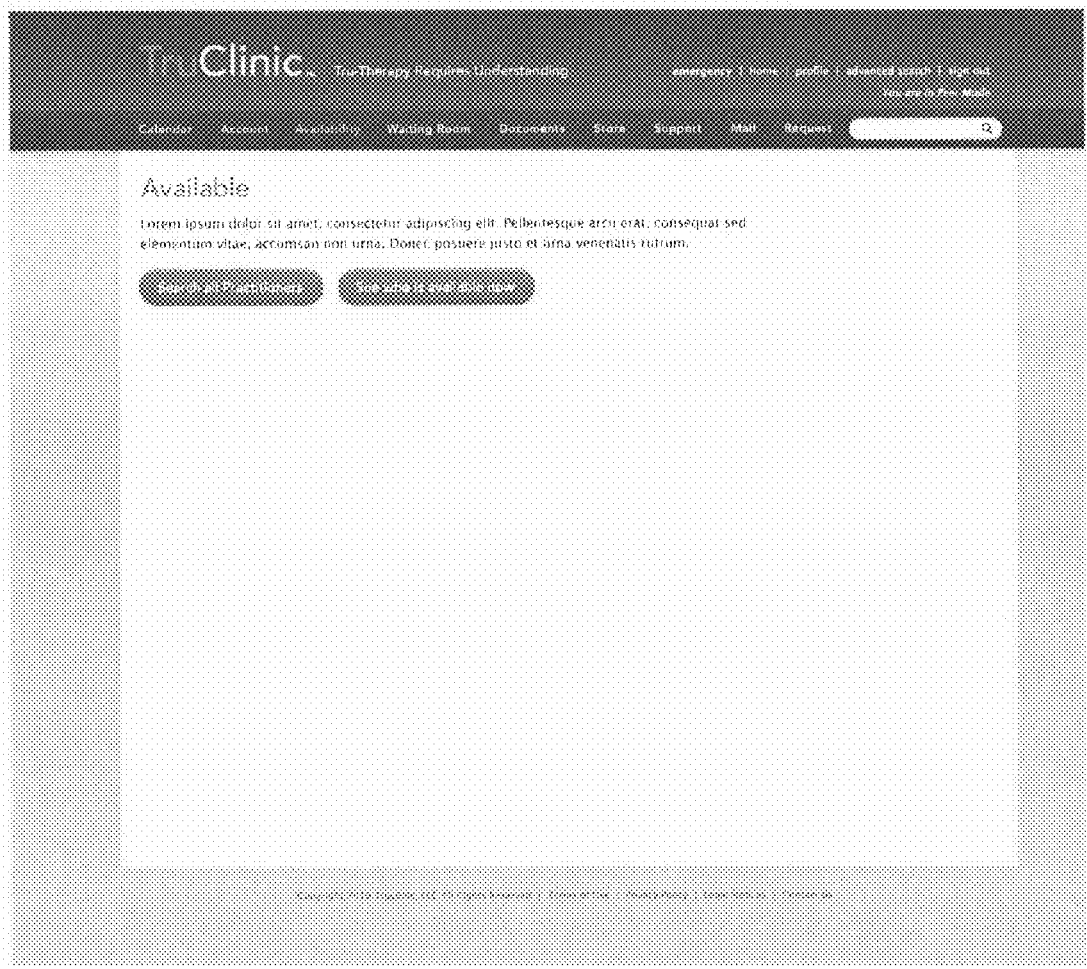
Figure 14:
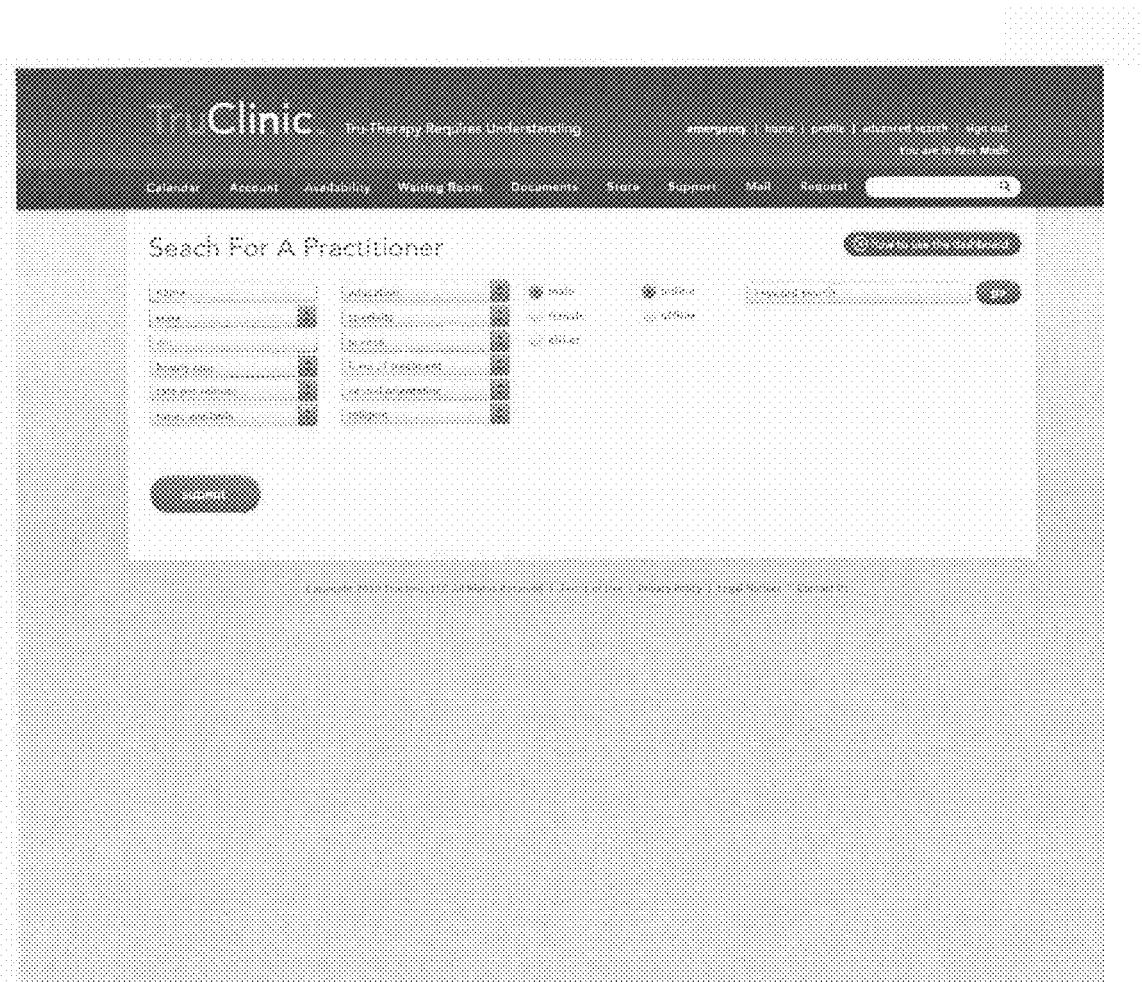
Figure 15:
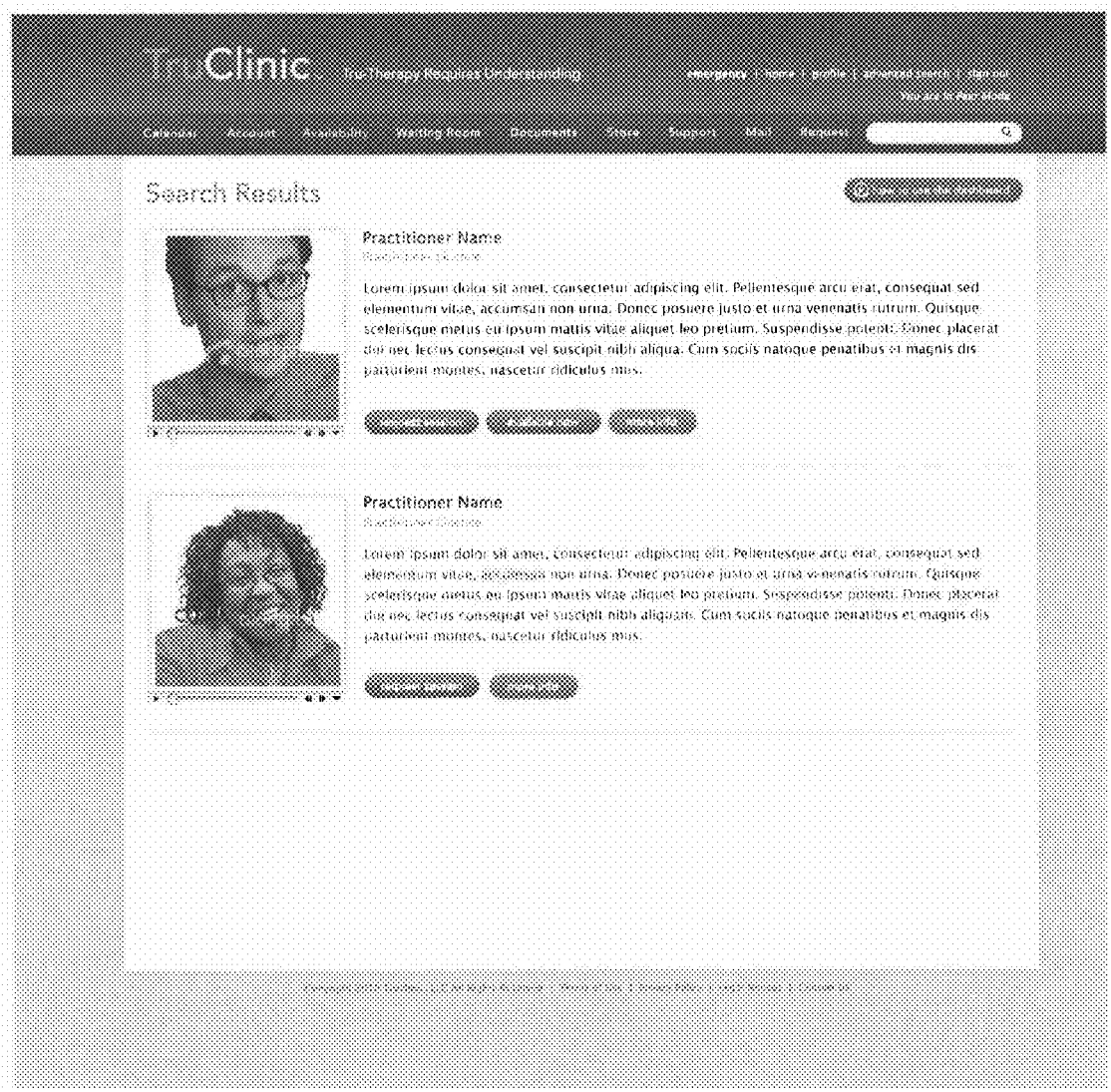
Figure 16:
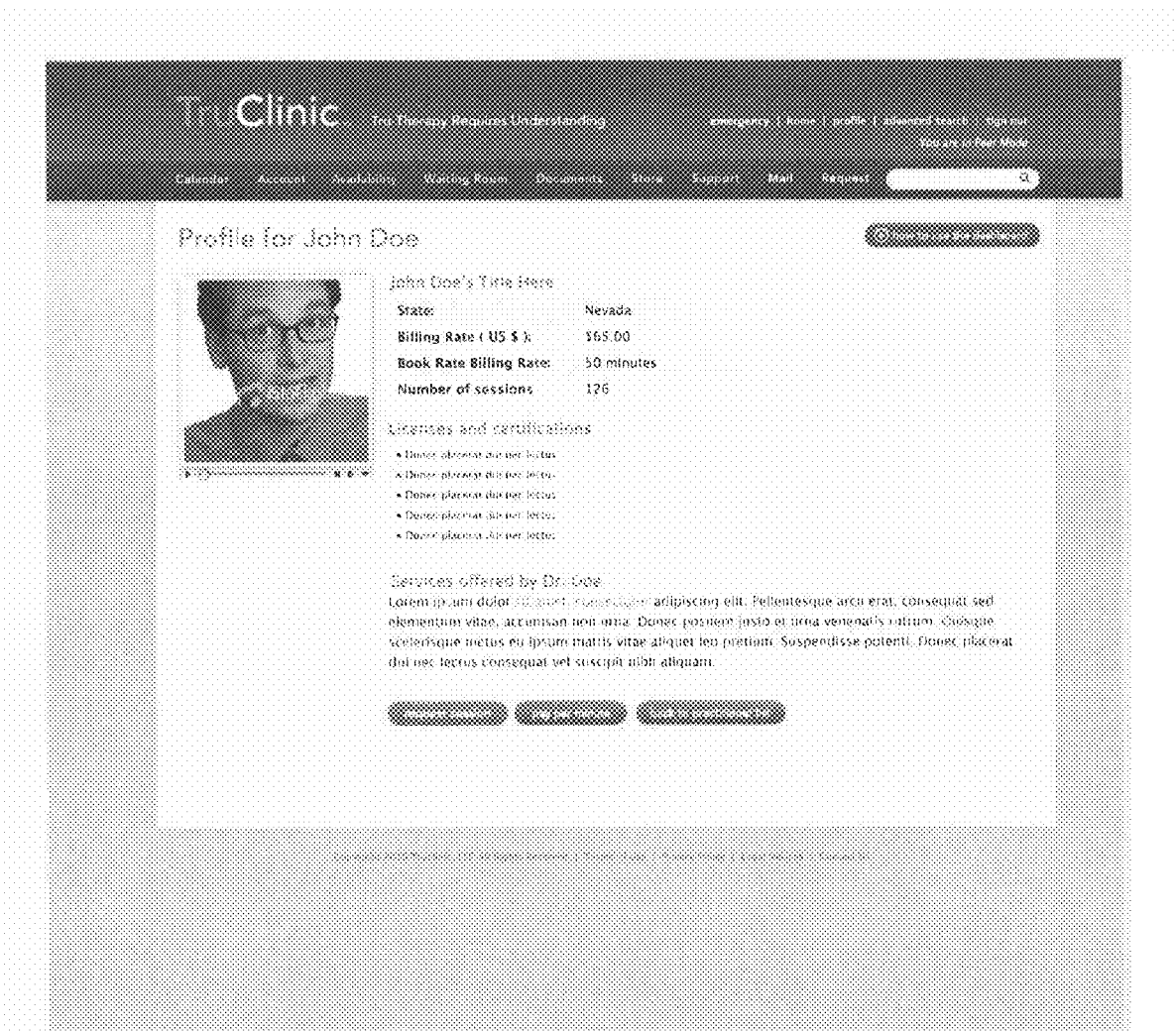
Figure 17:
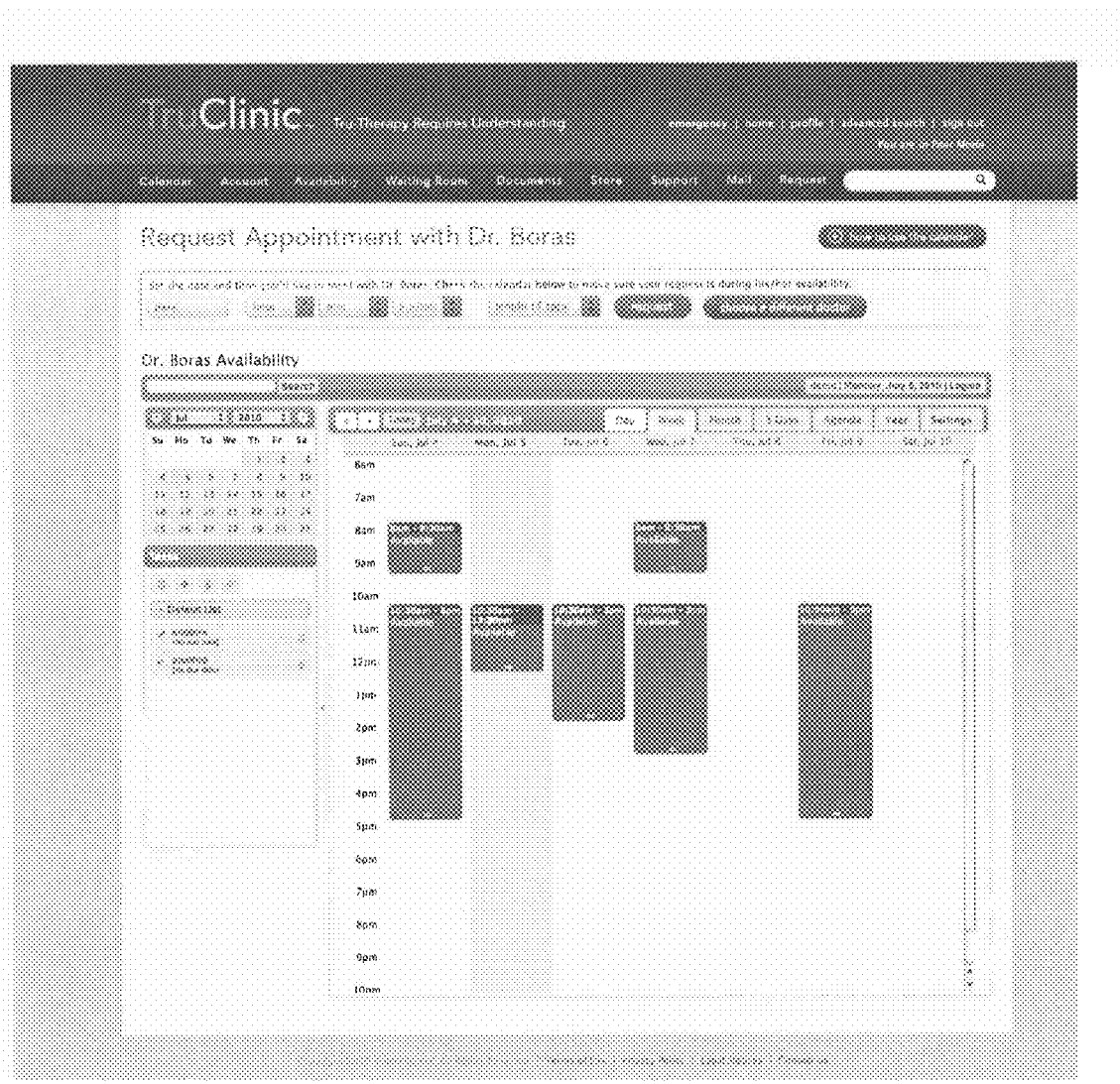
Figure 18:
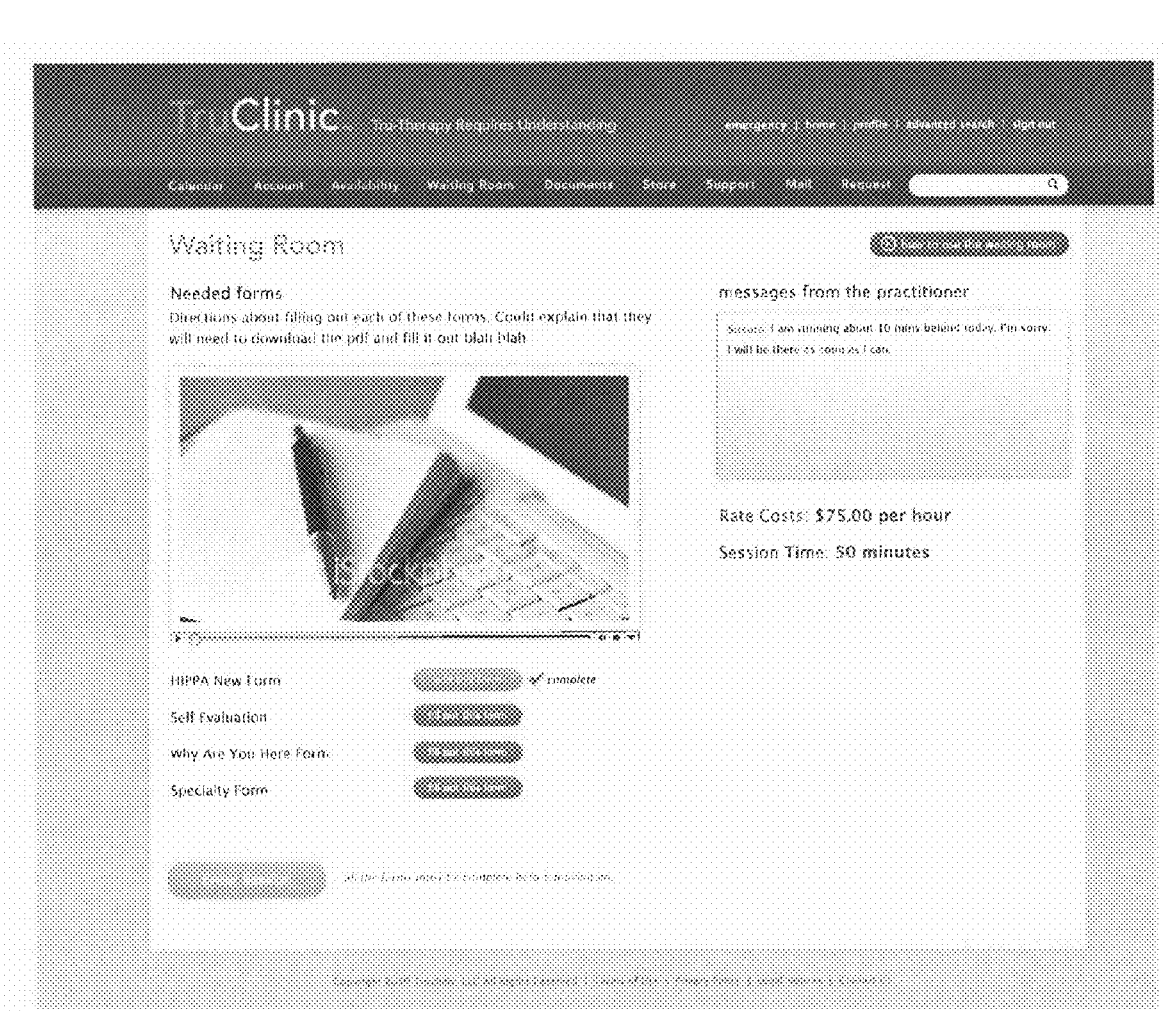
Figure 19:
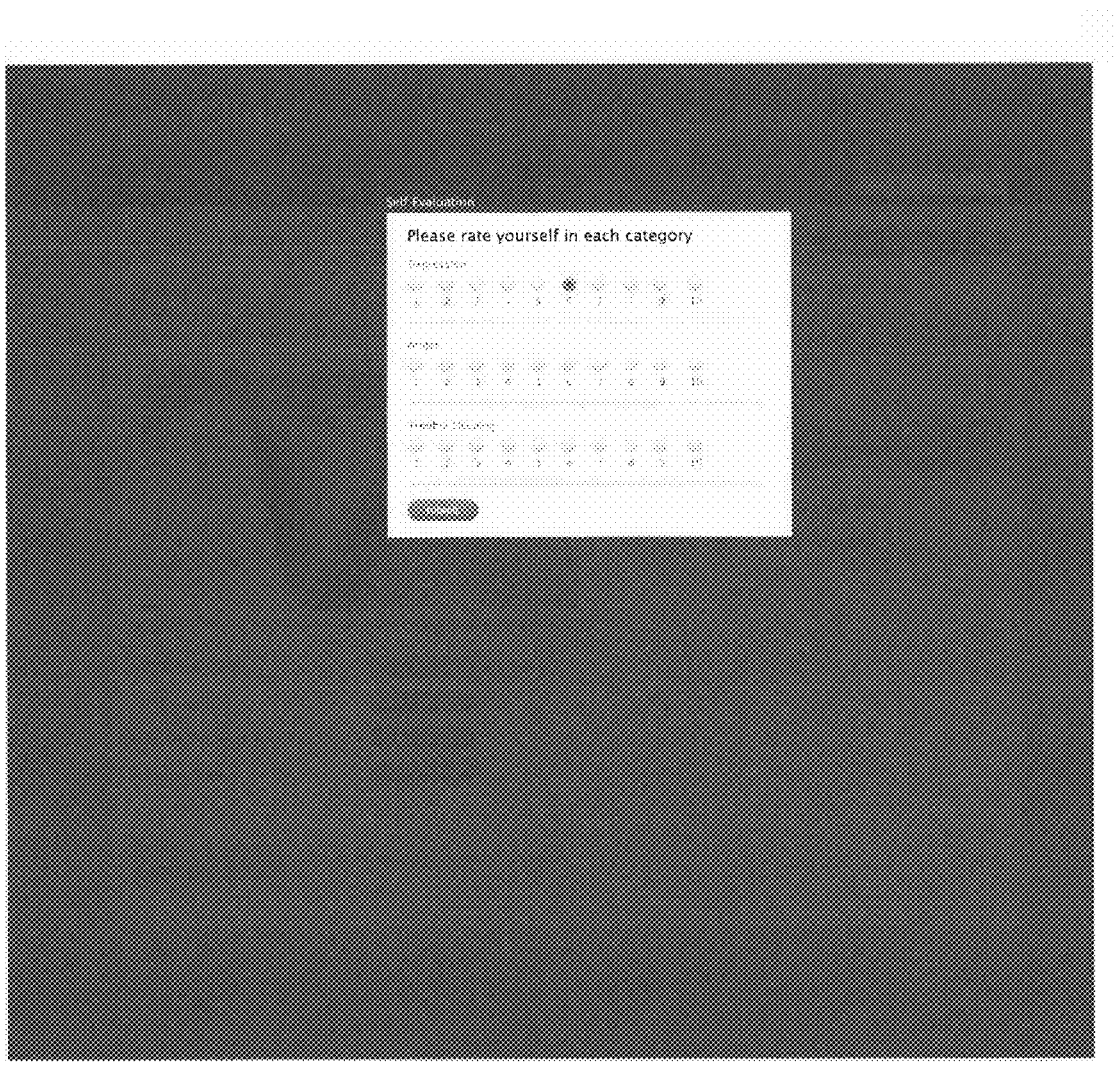
Figure 20:
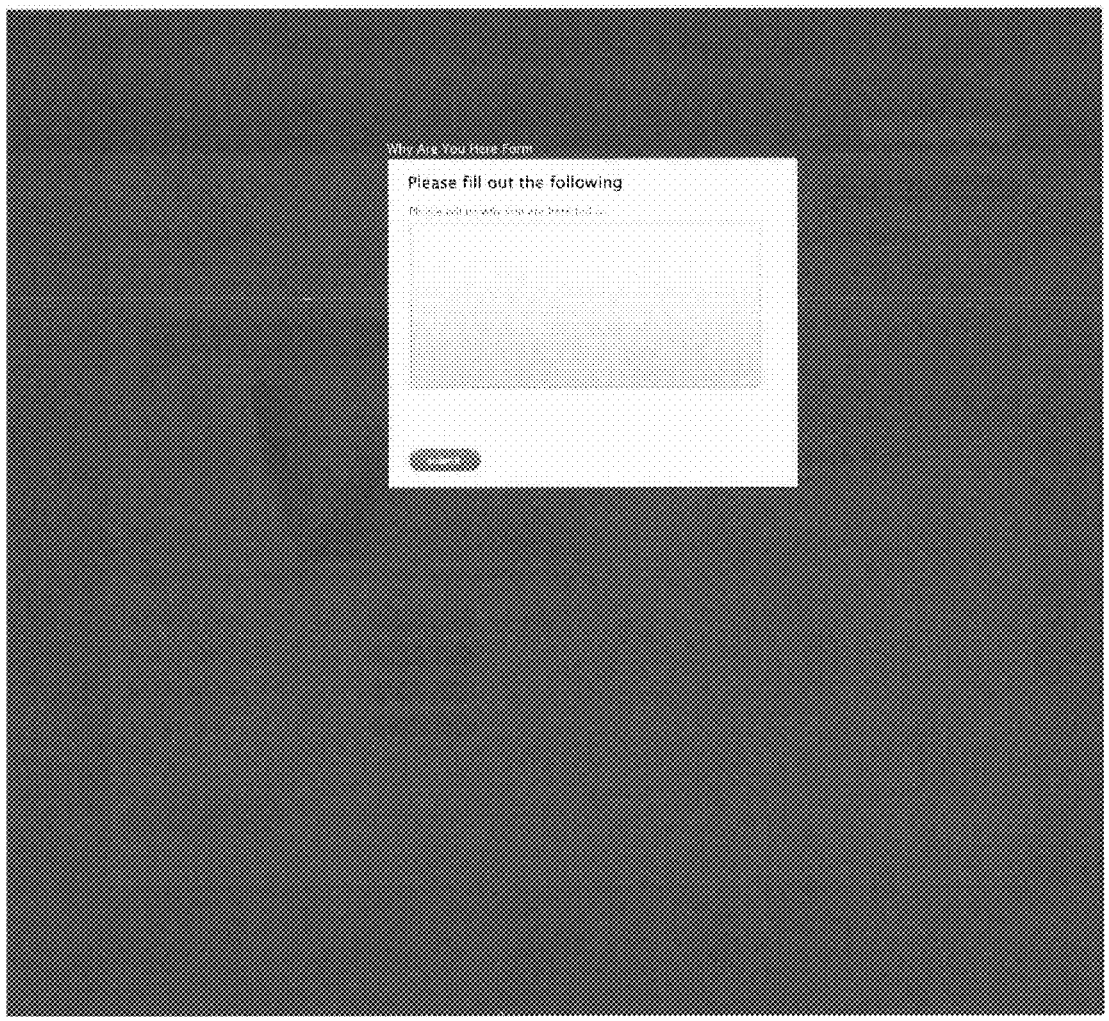
Figure 21:
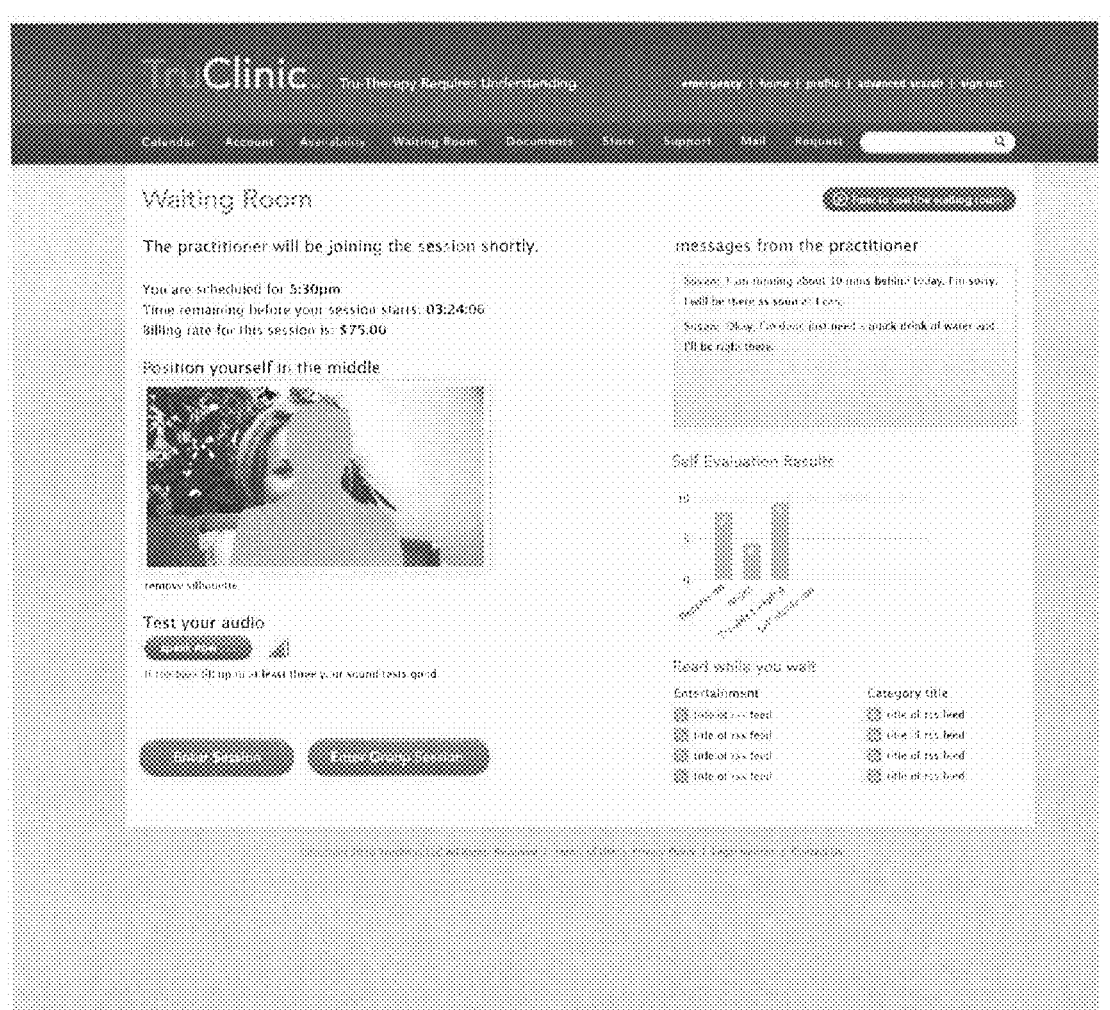
Figure 22:
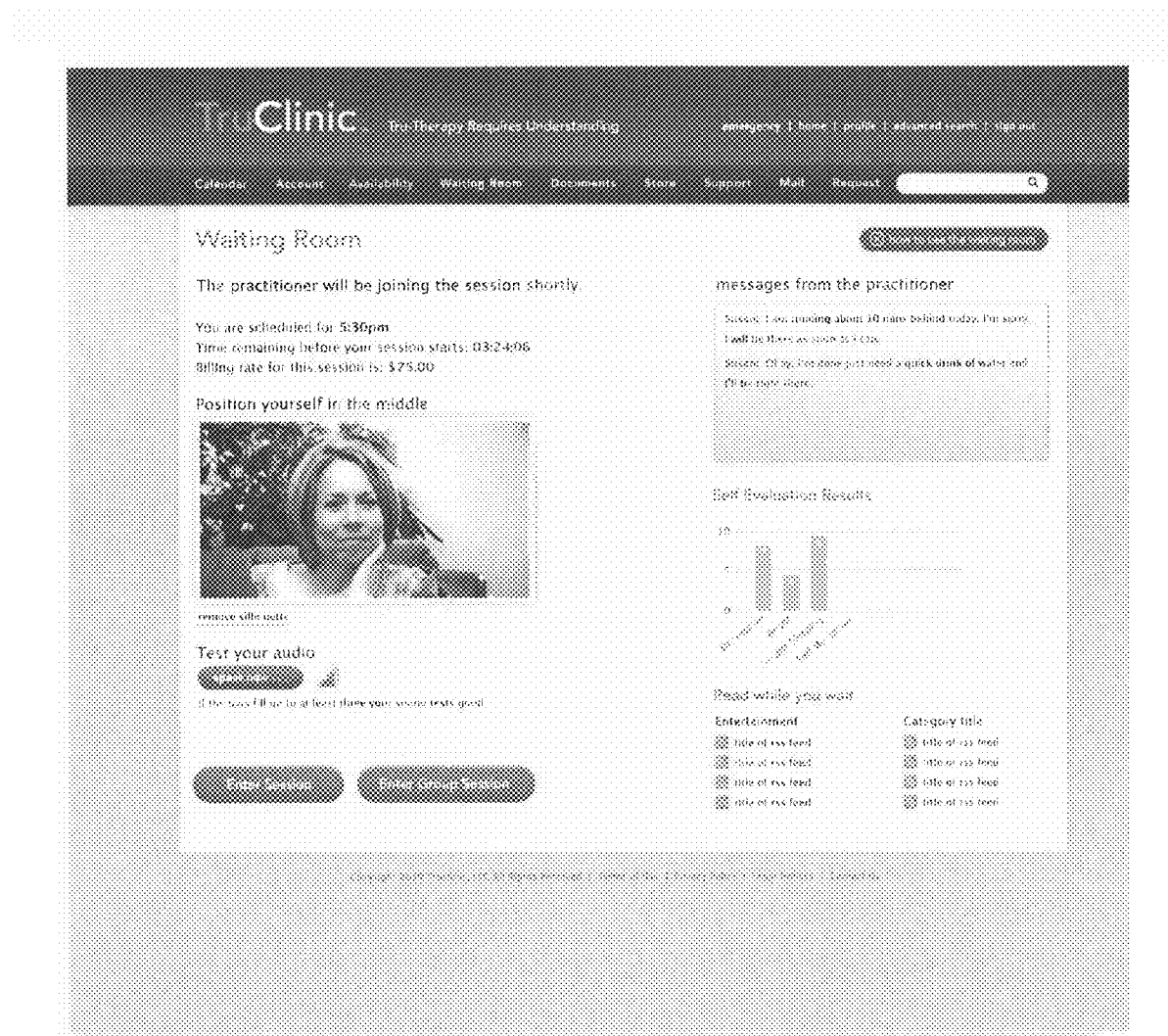
Figure 23:
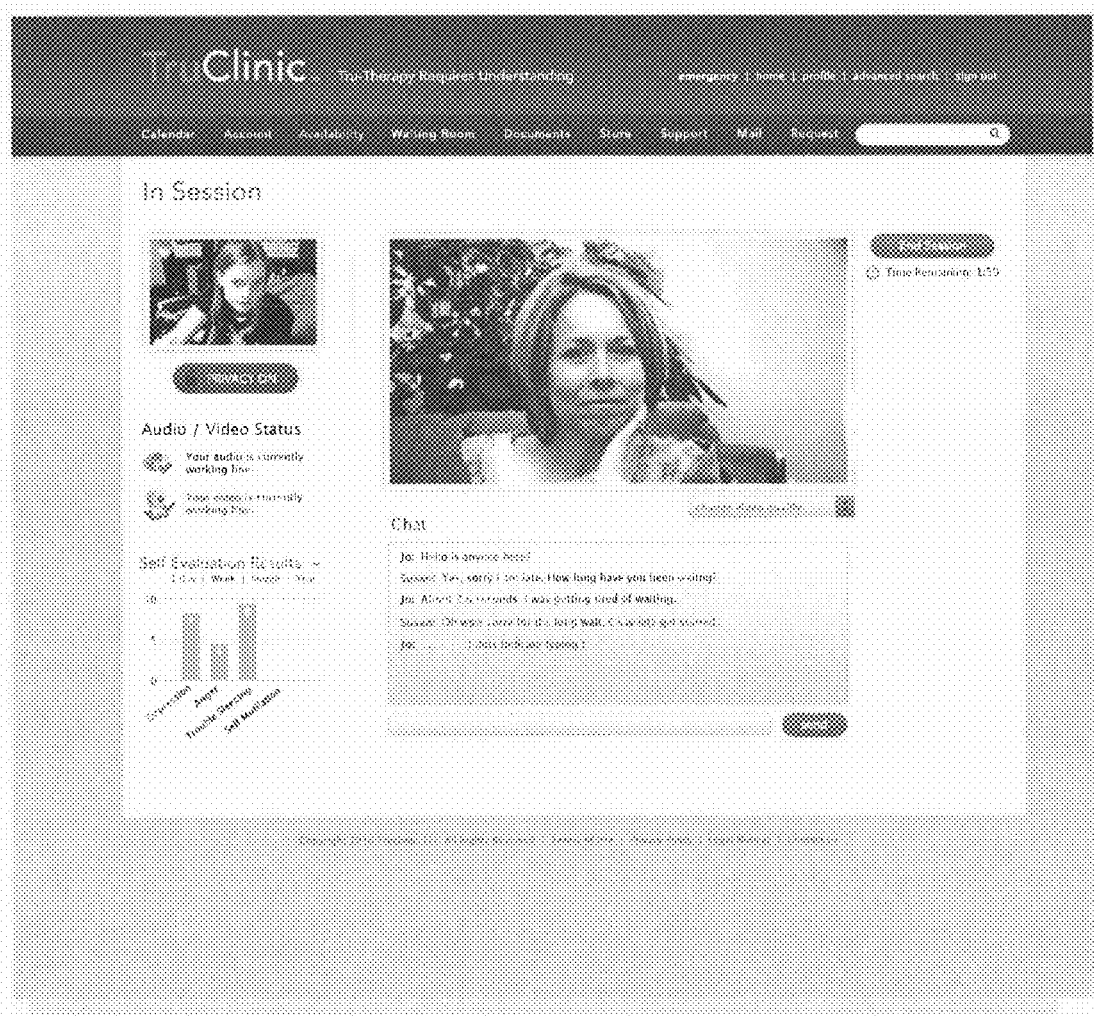
Figure 24:
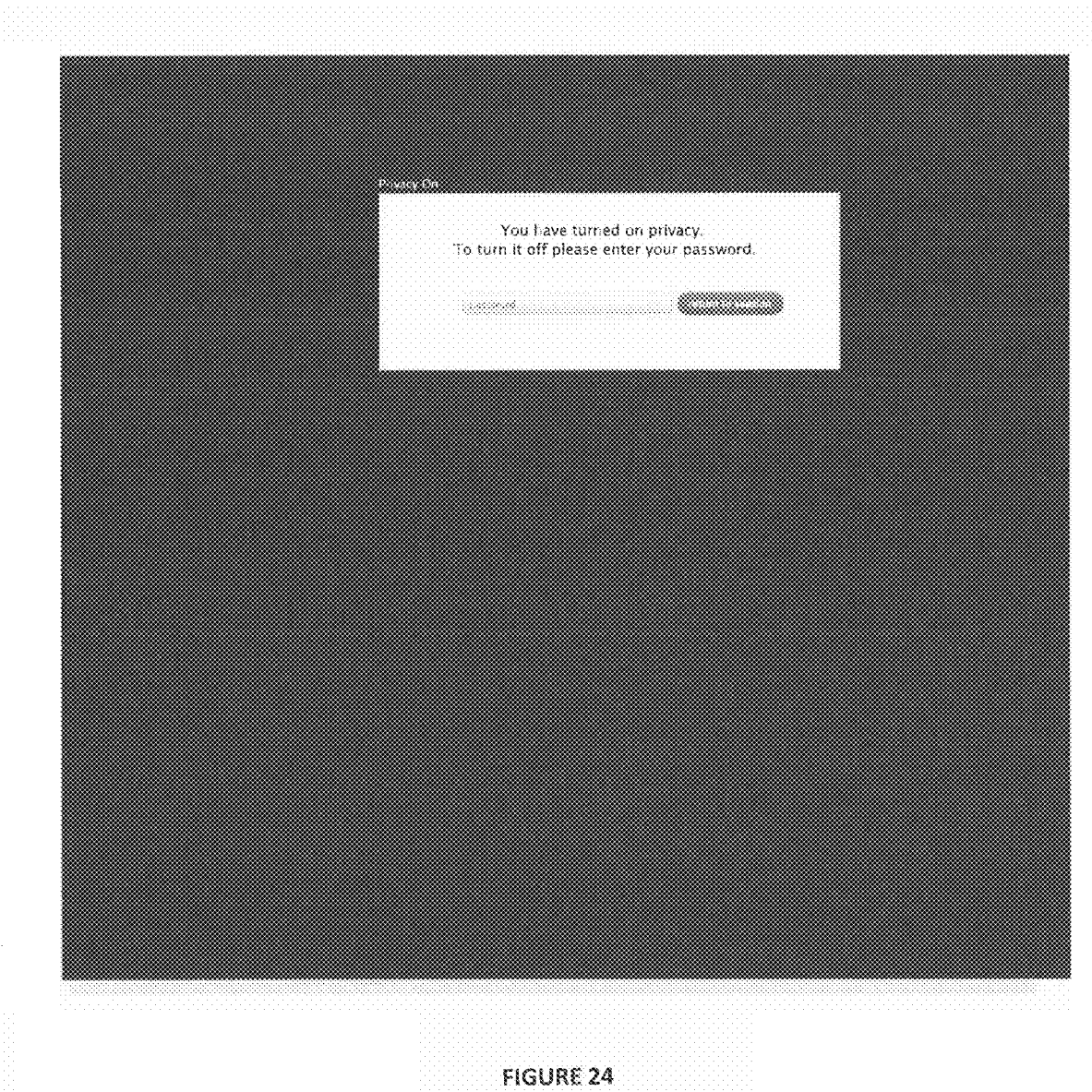
Figure 25:
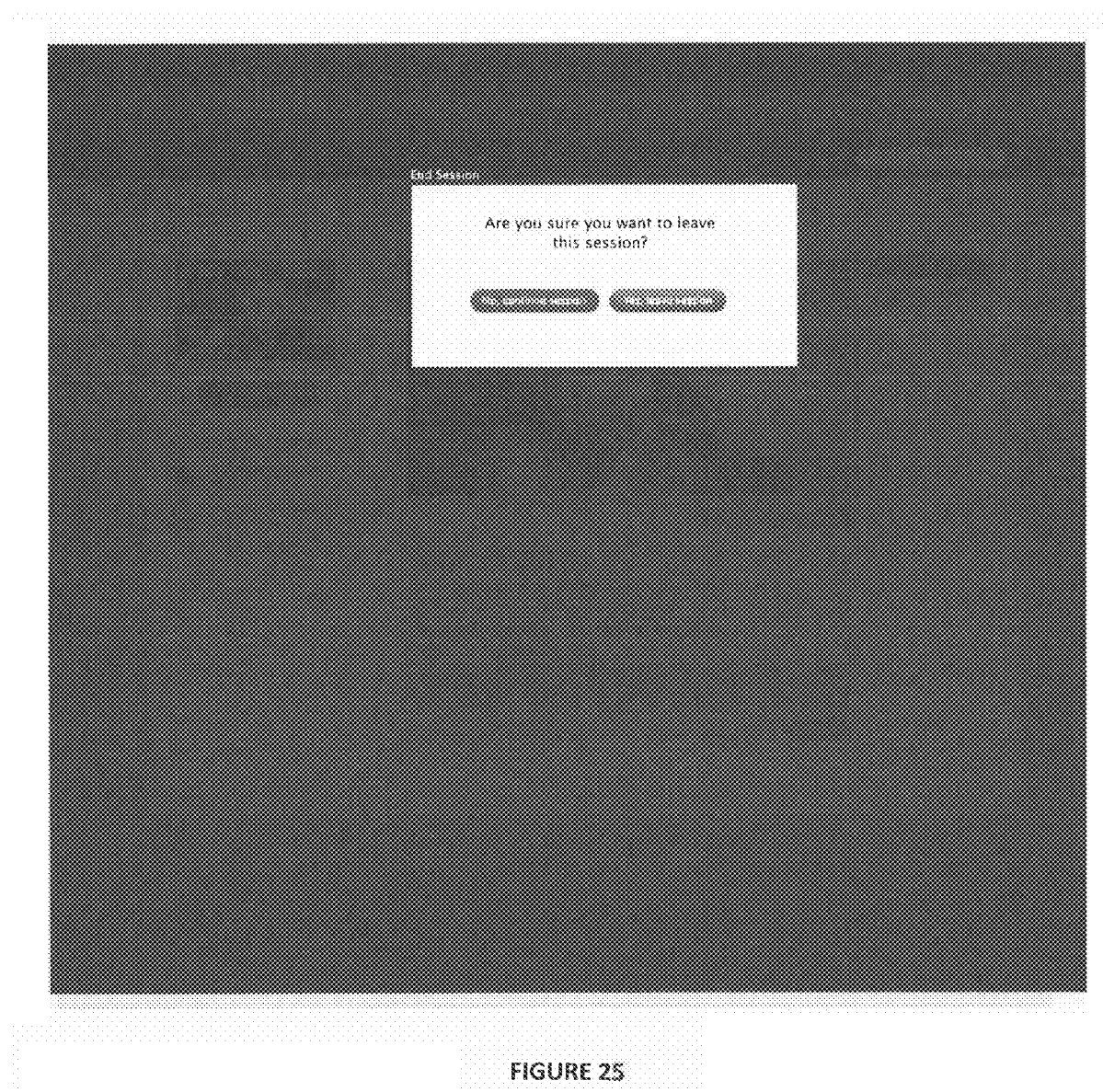
Figure 26:
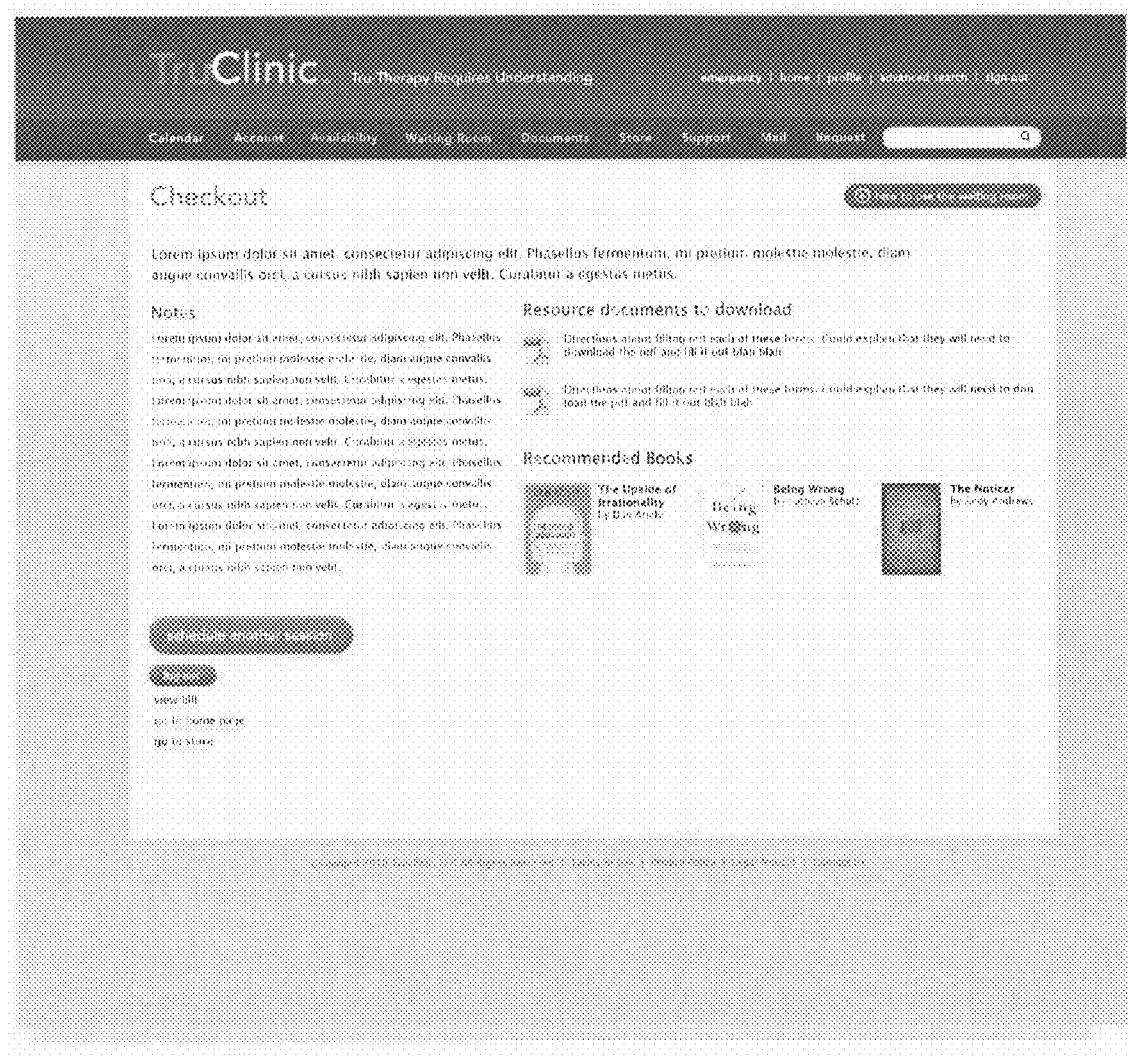
Figure 27:
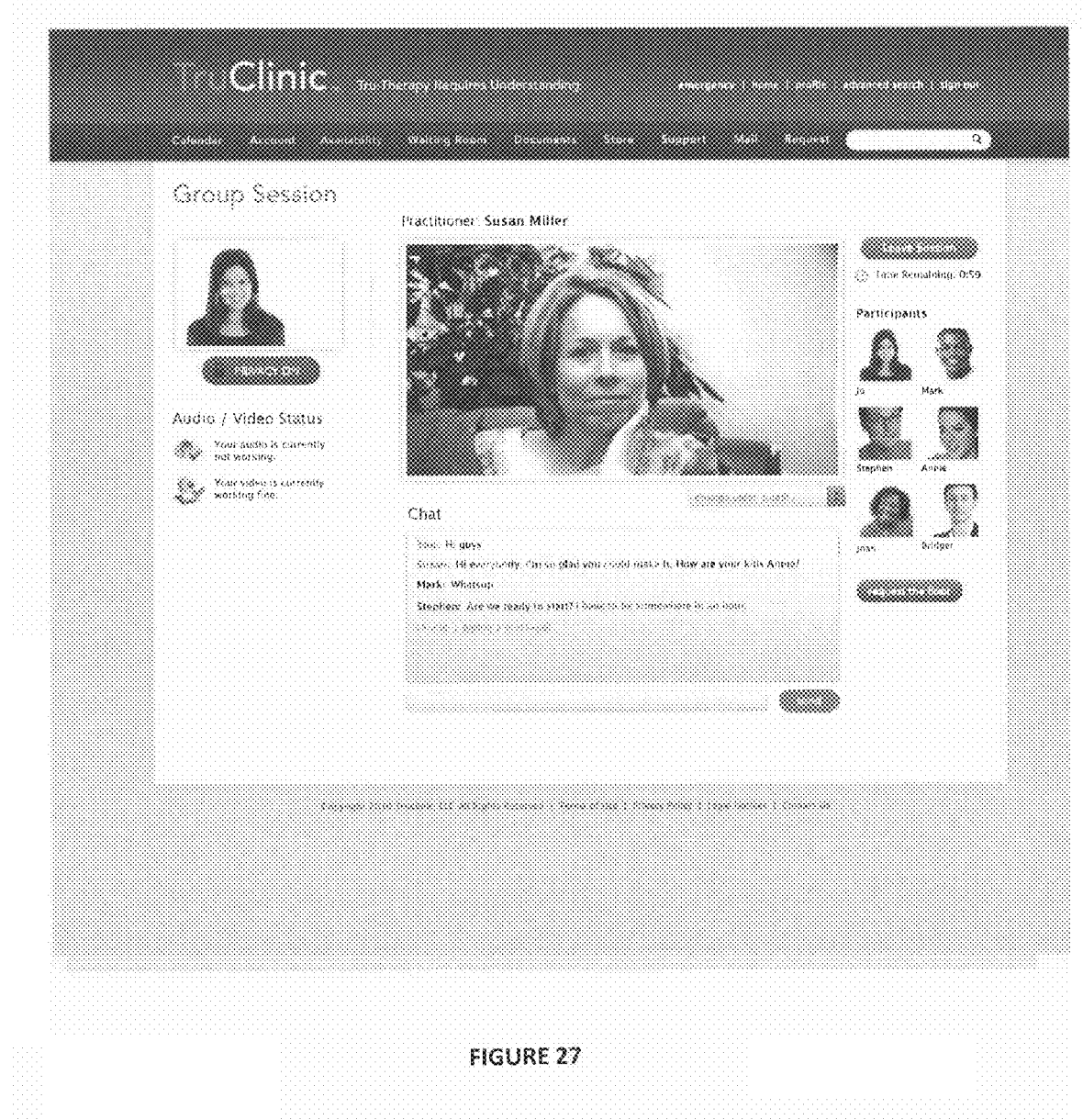
Figure 28:
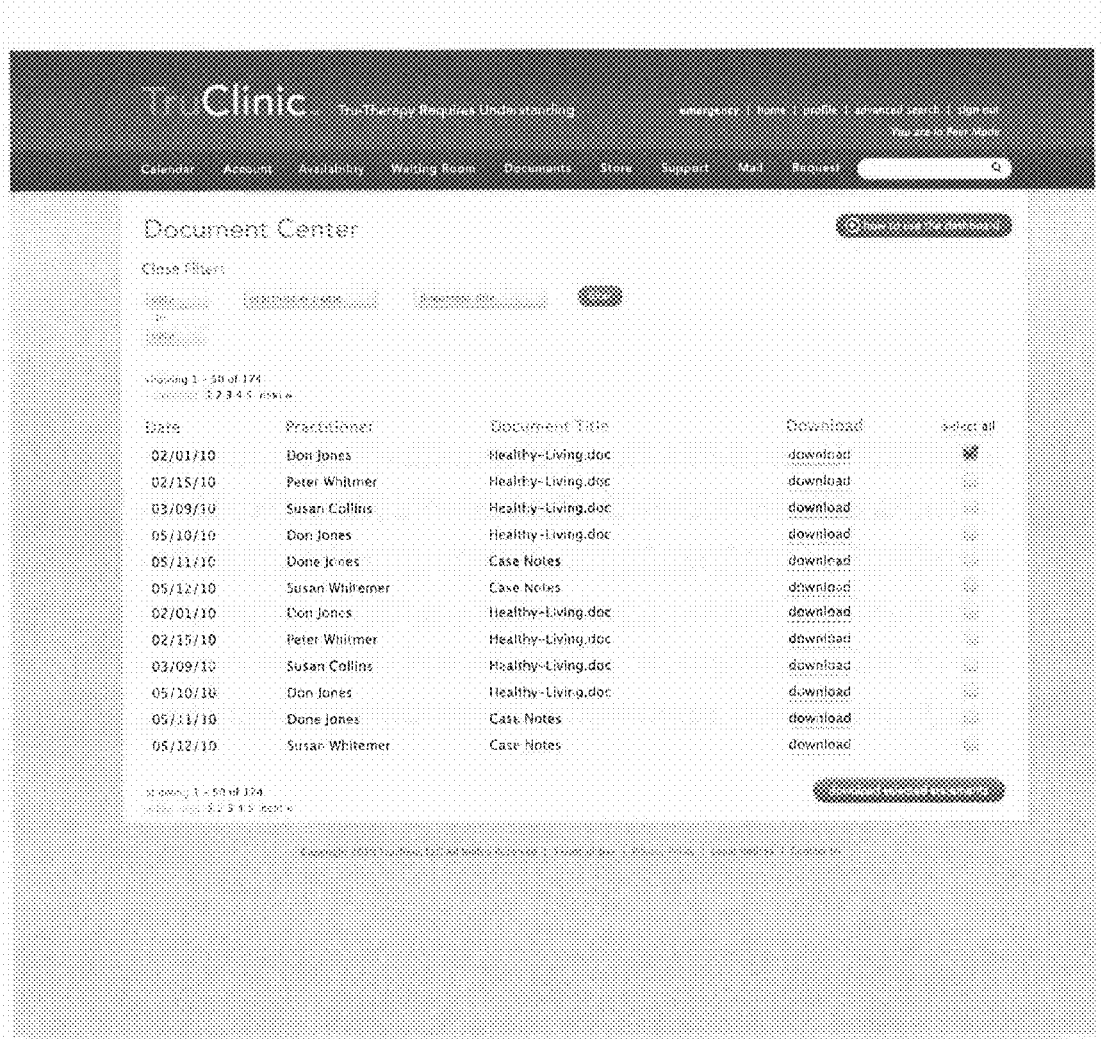
Figure 29:
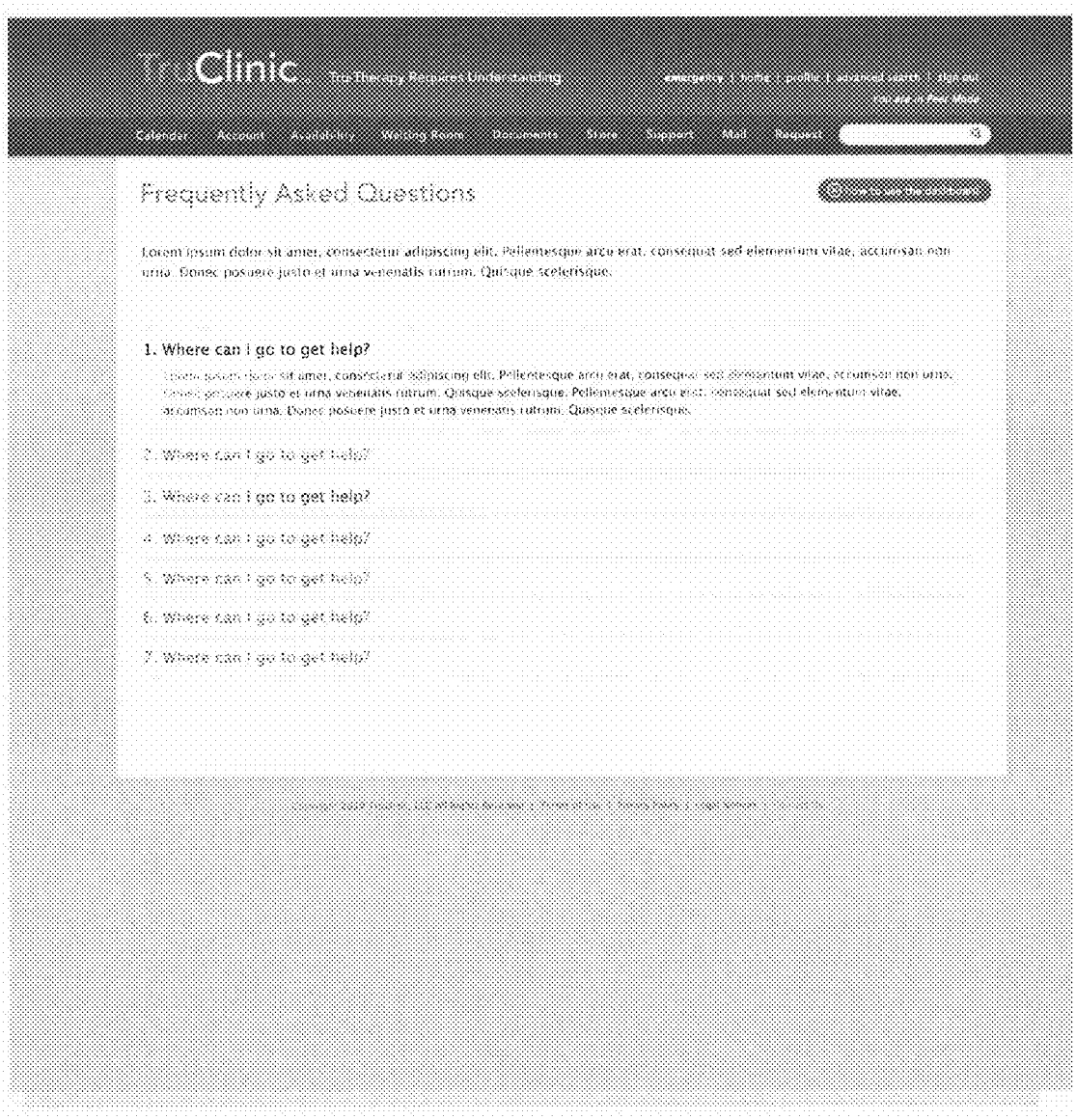
Figure 30:
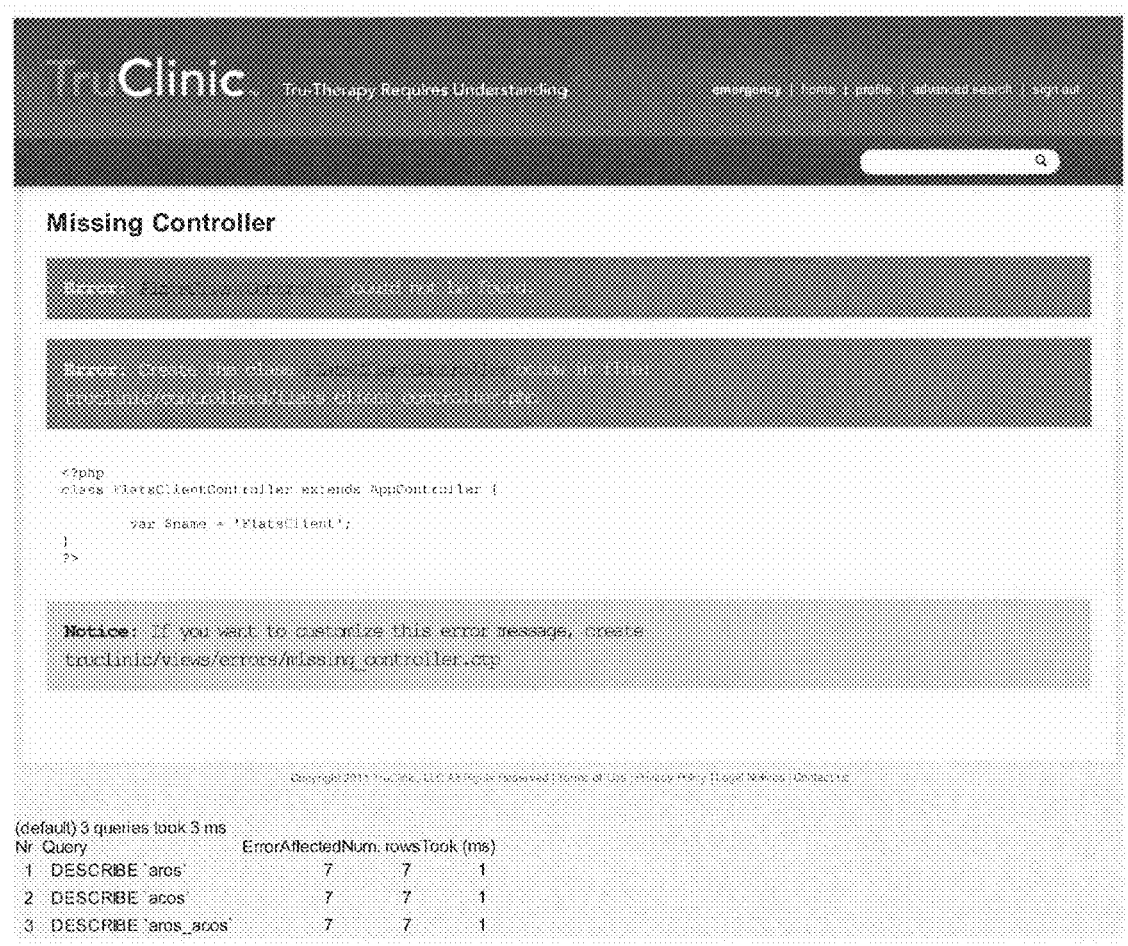
Figure 31:
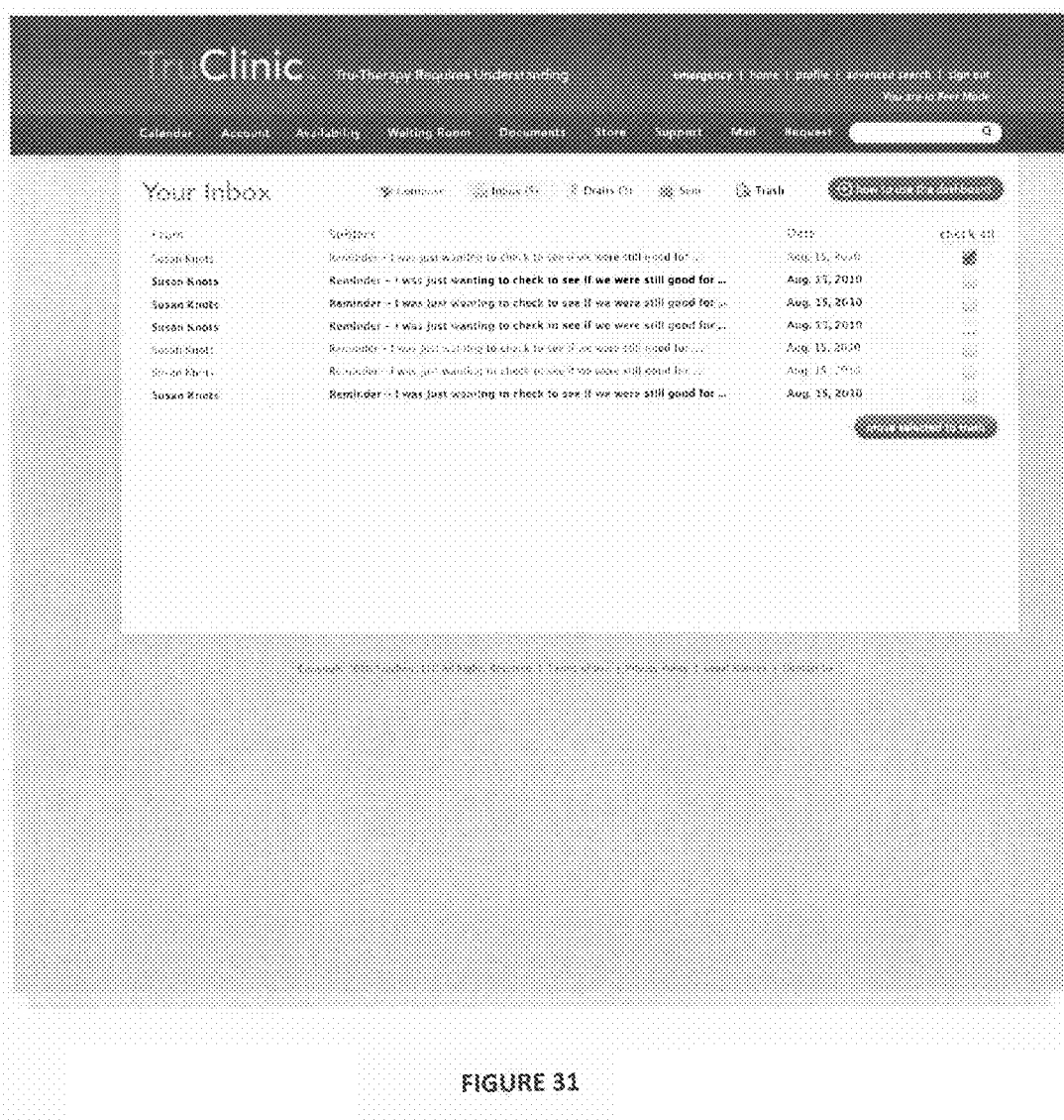
Figure 32:
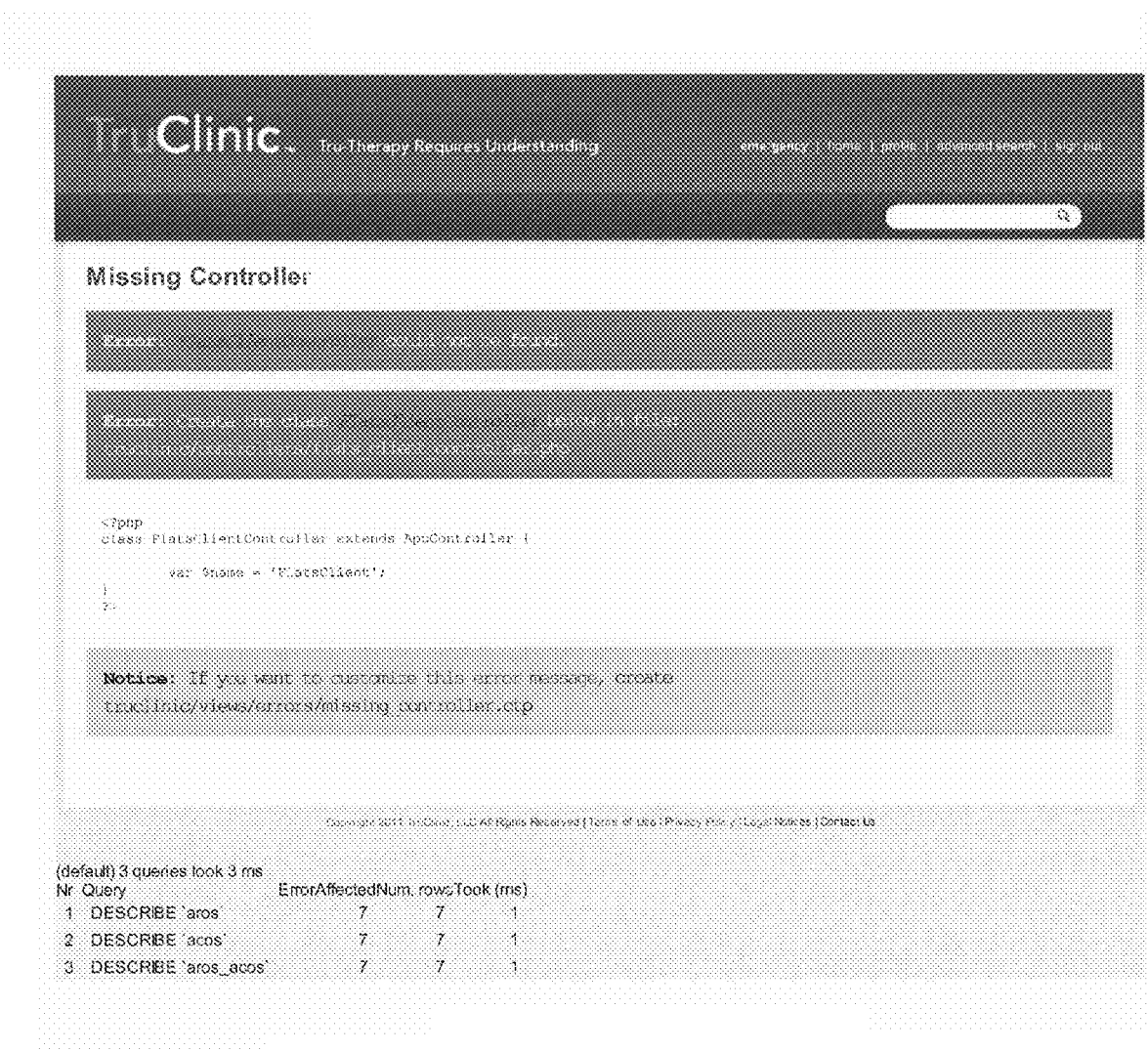
Figure 33:
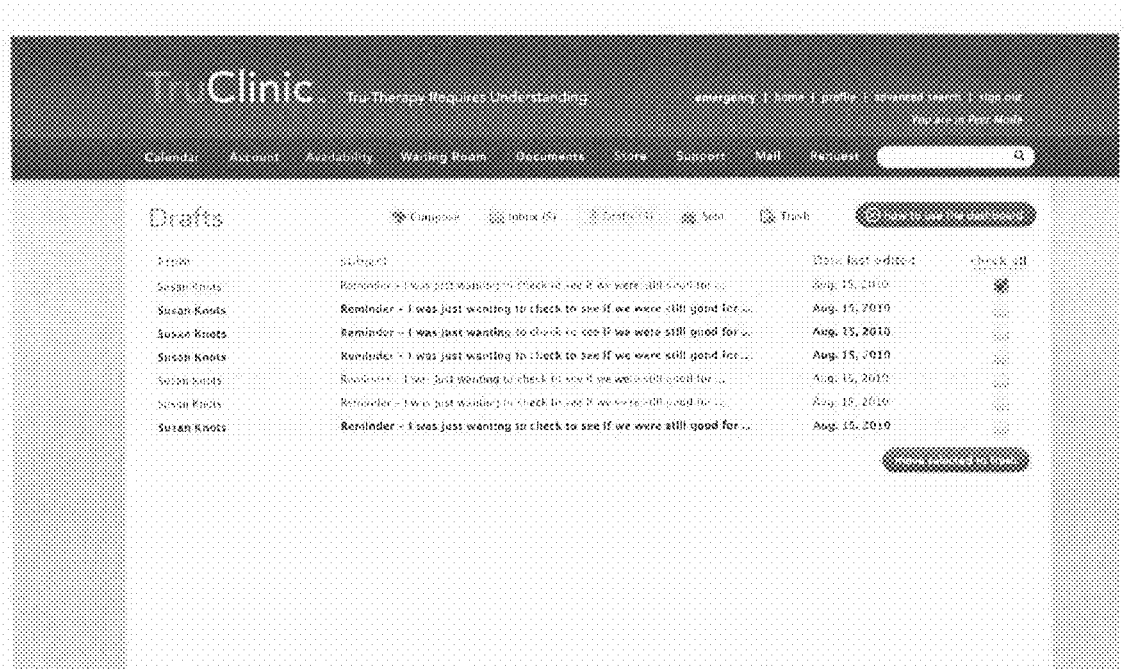
Figure 34:
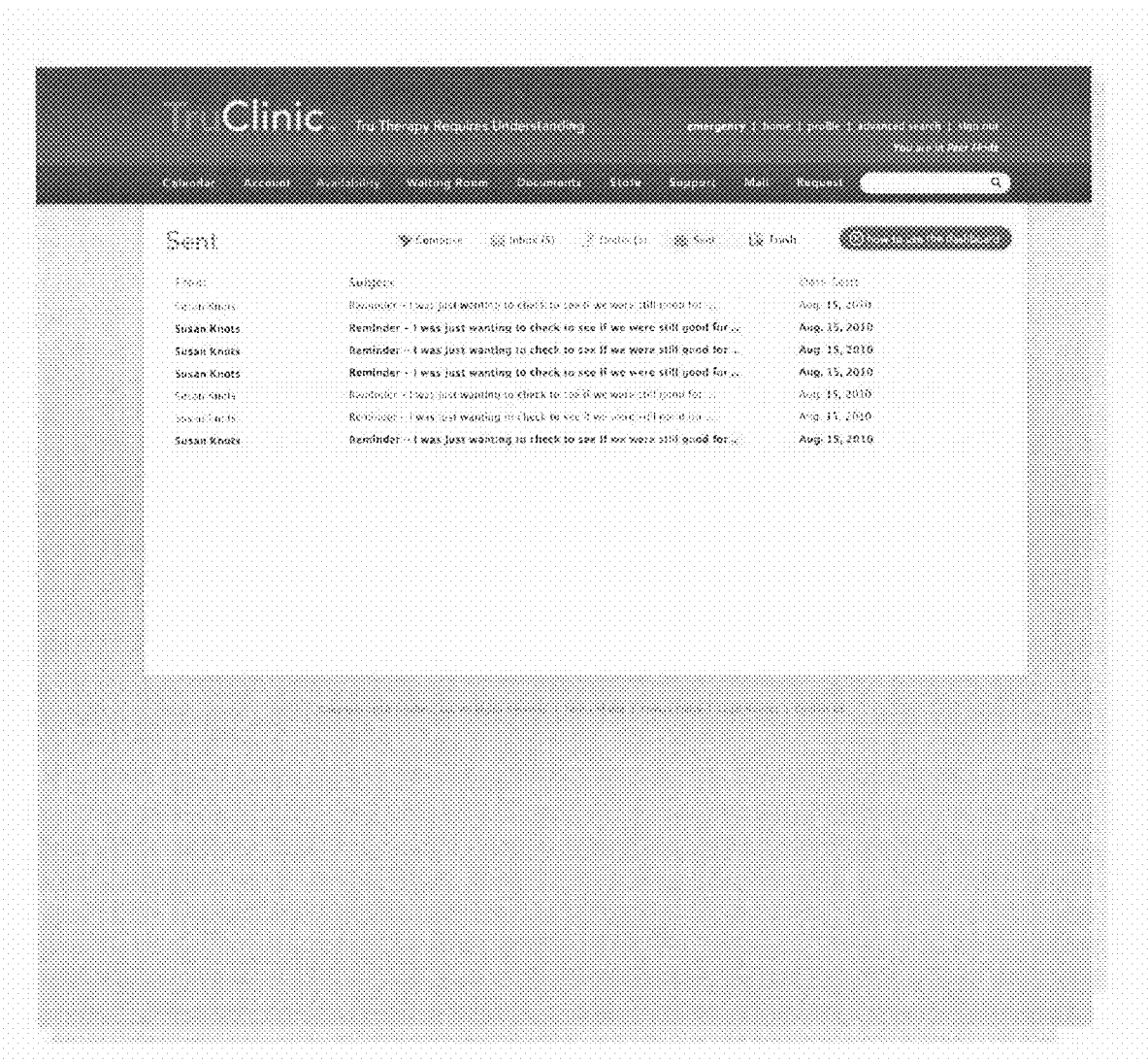
Figure 35:
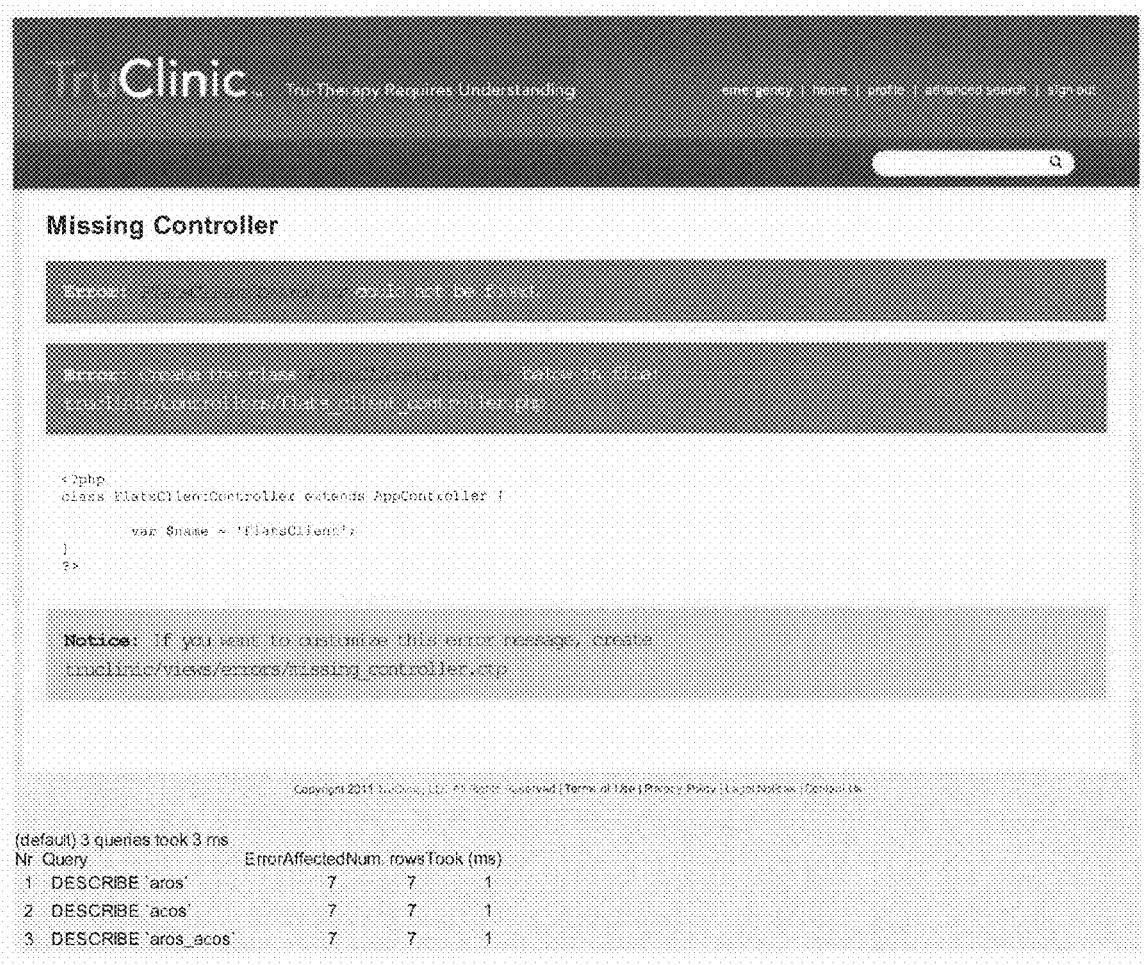
Figure 36:
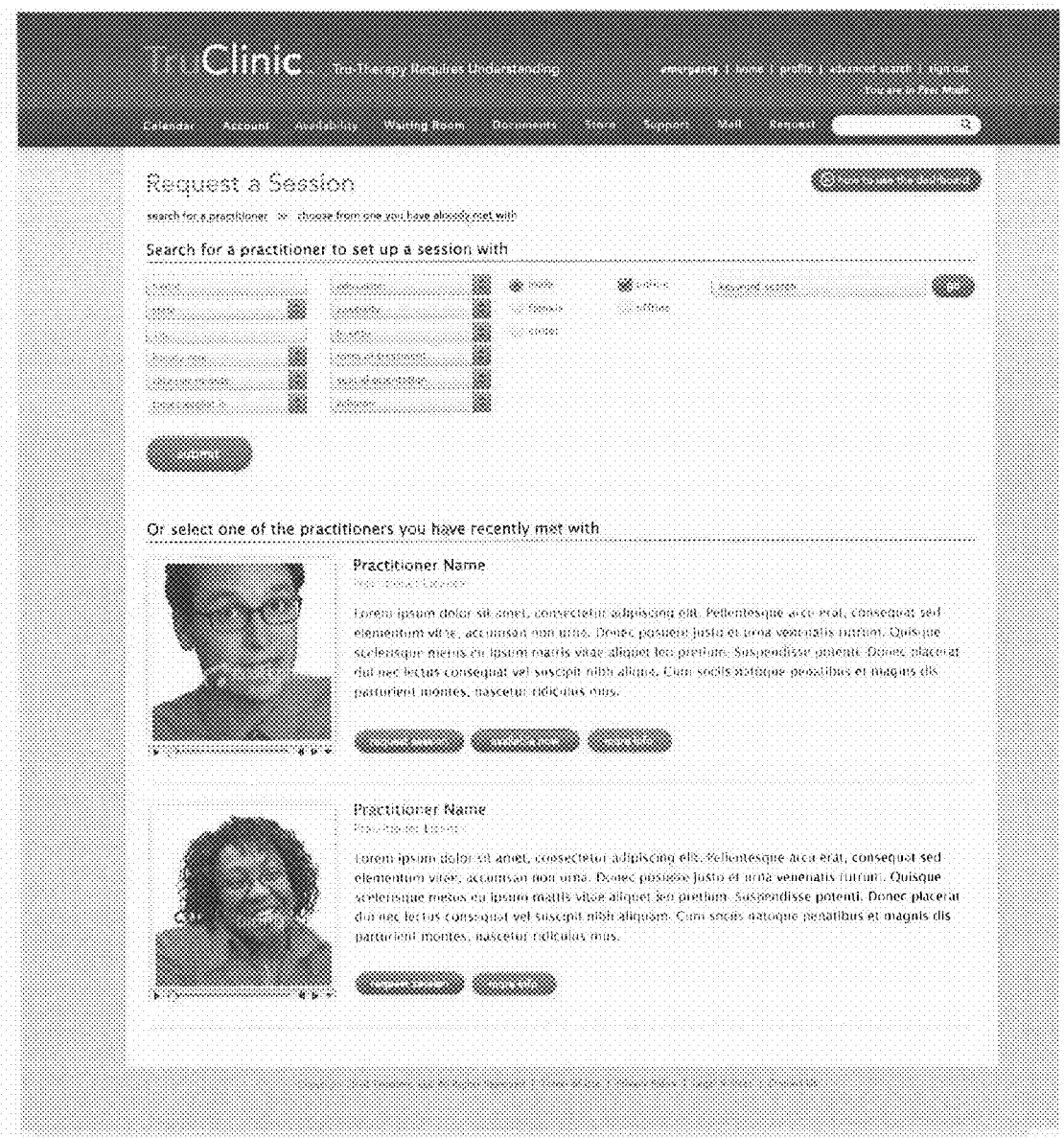
Figure 37:
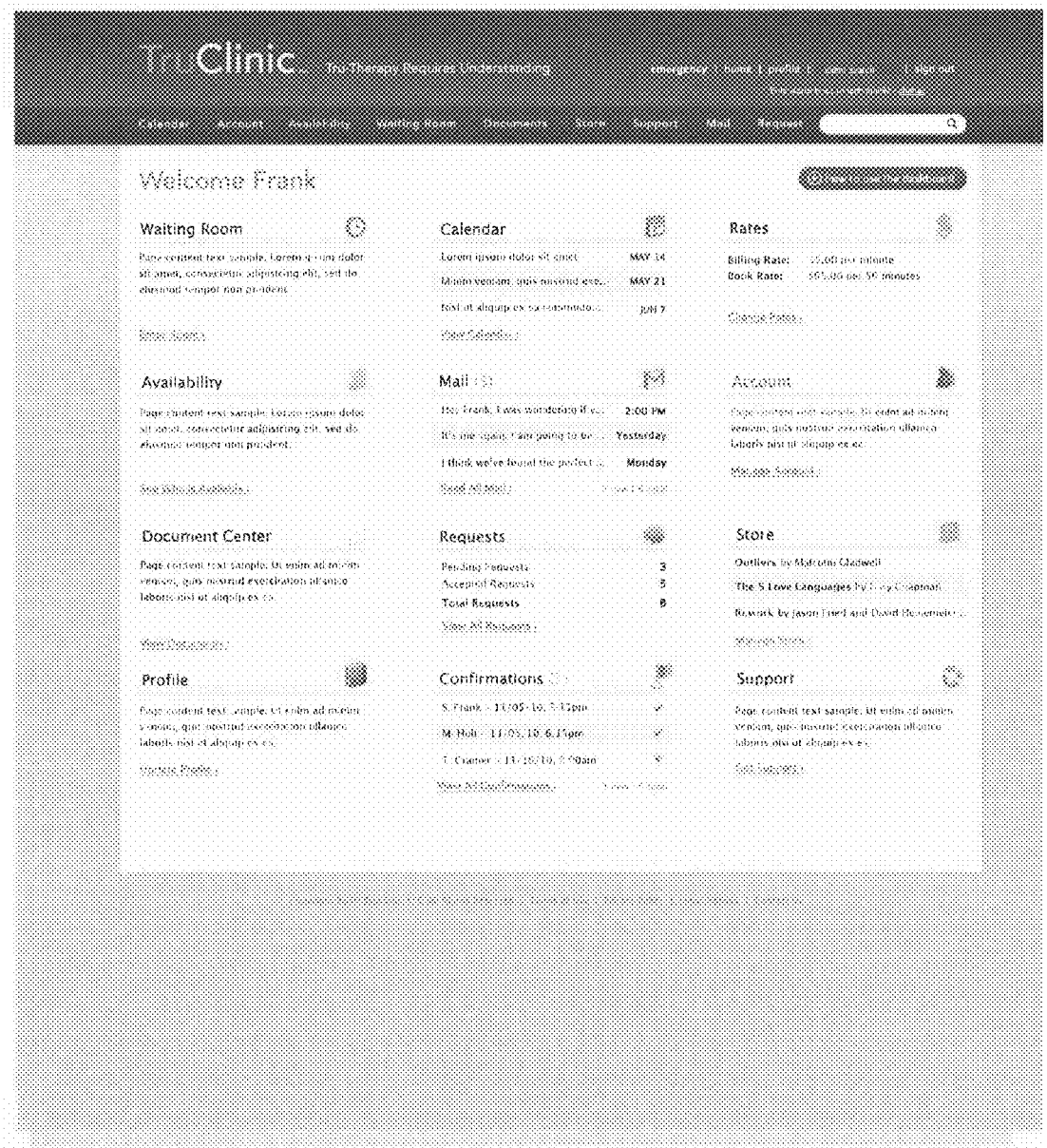
Figure 38:
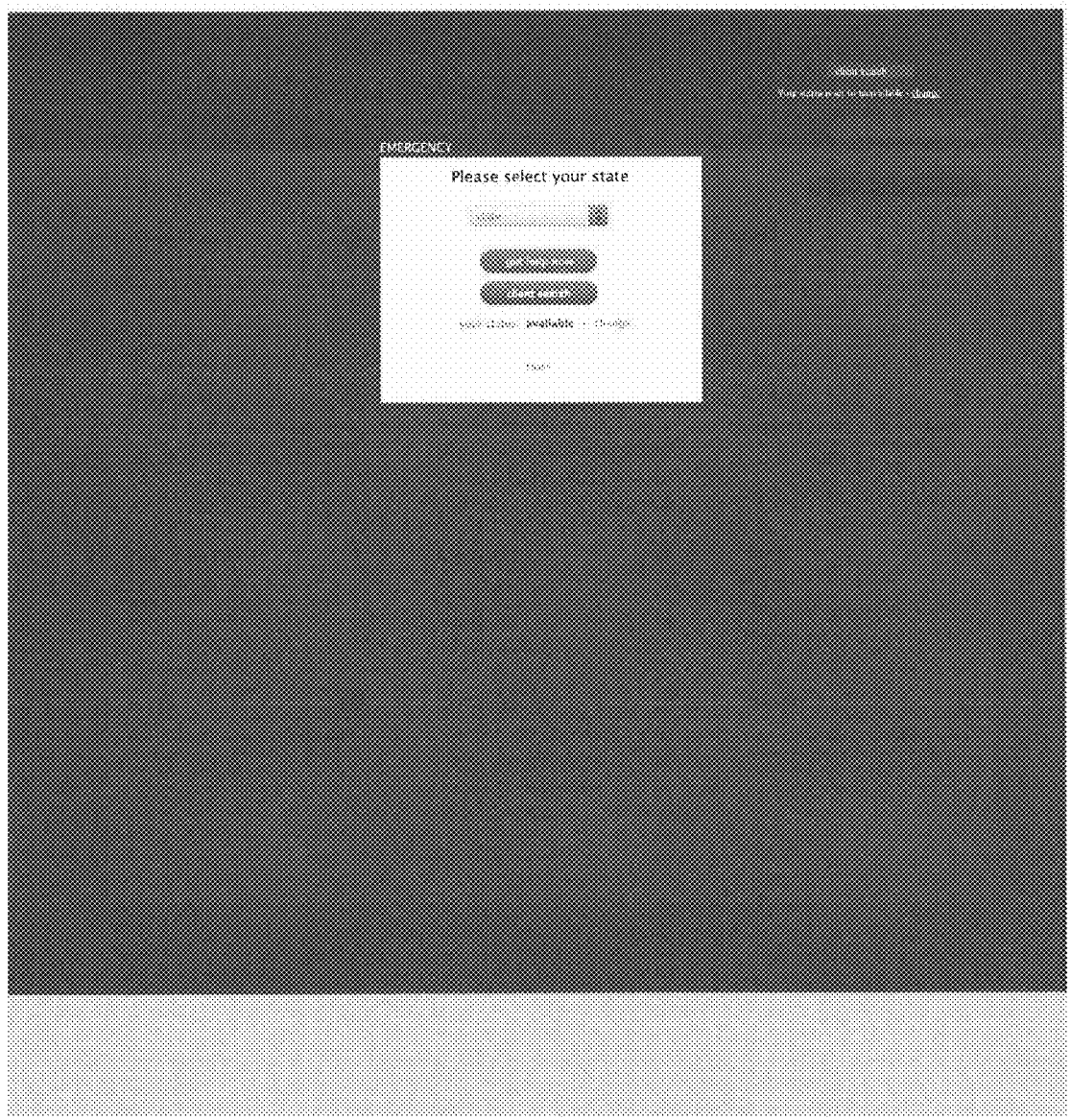
Figure 39:
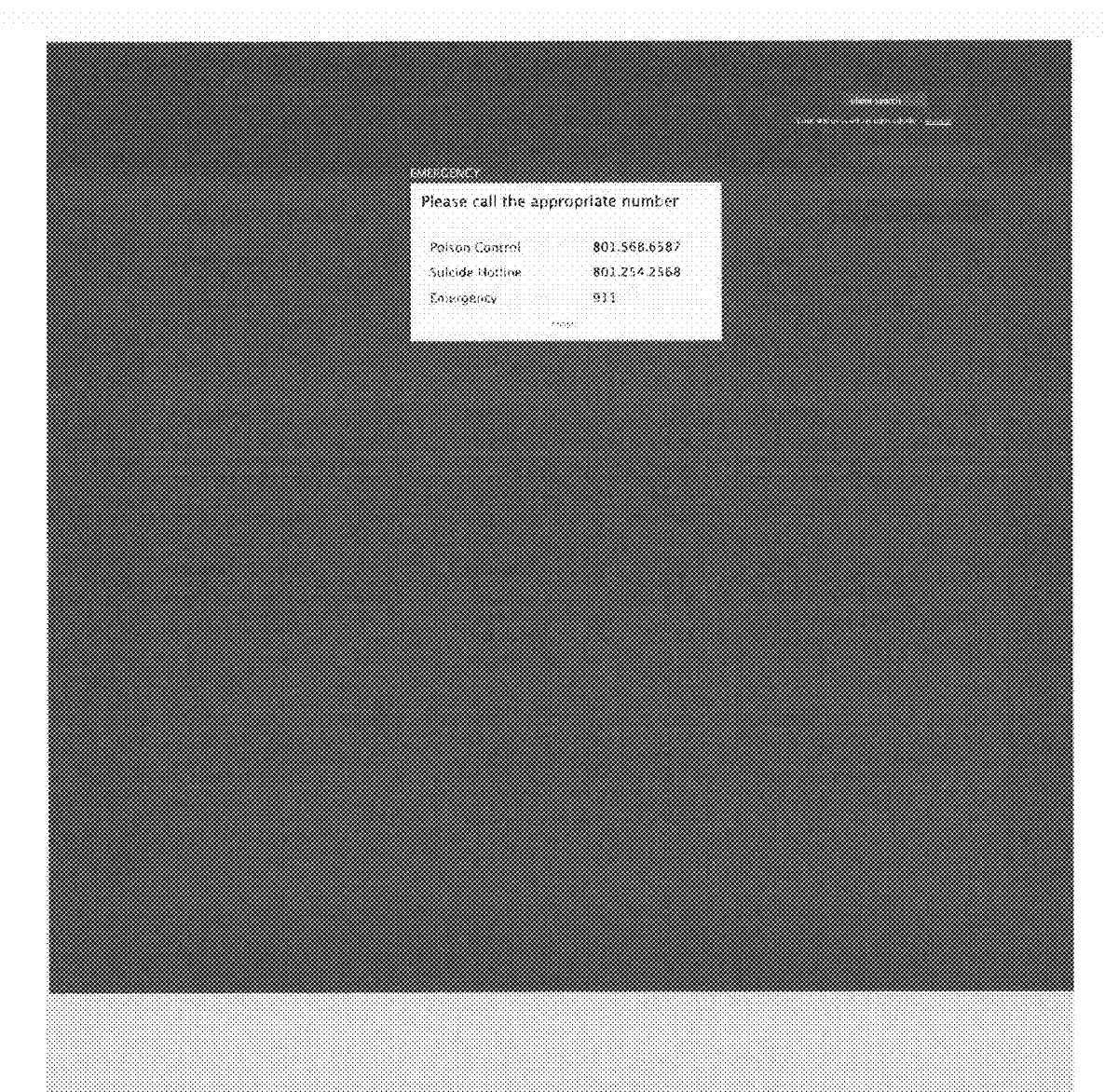
Figure 40:
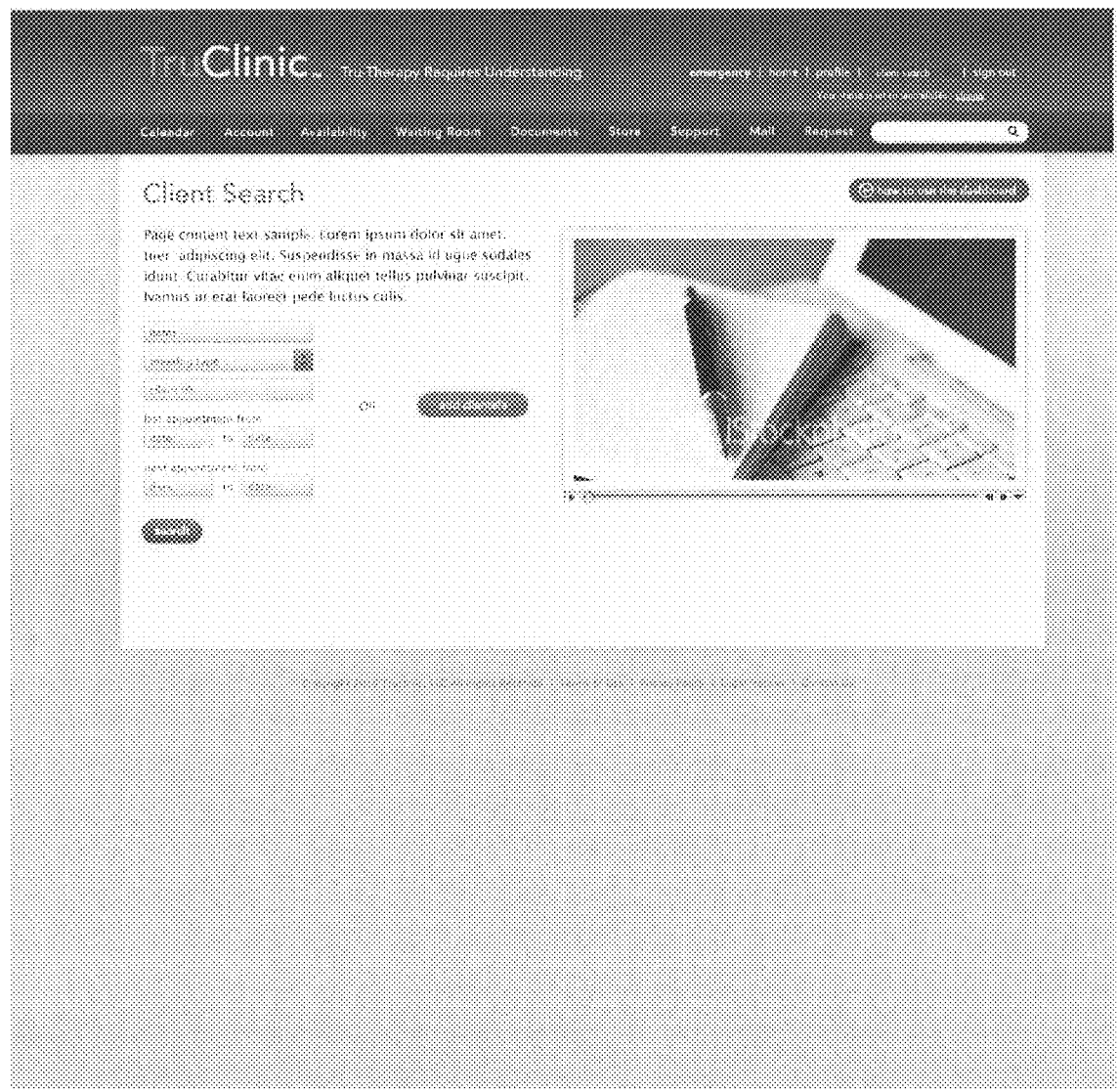
Figure 42:
Figure 43:
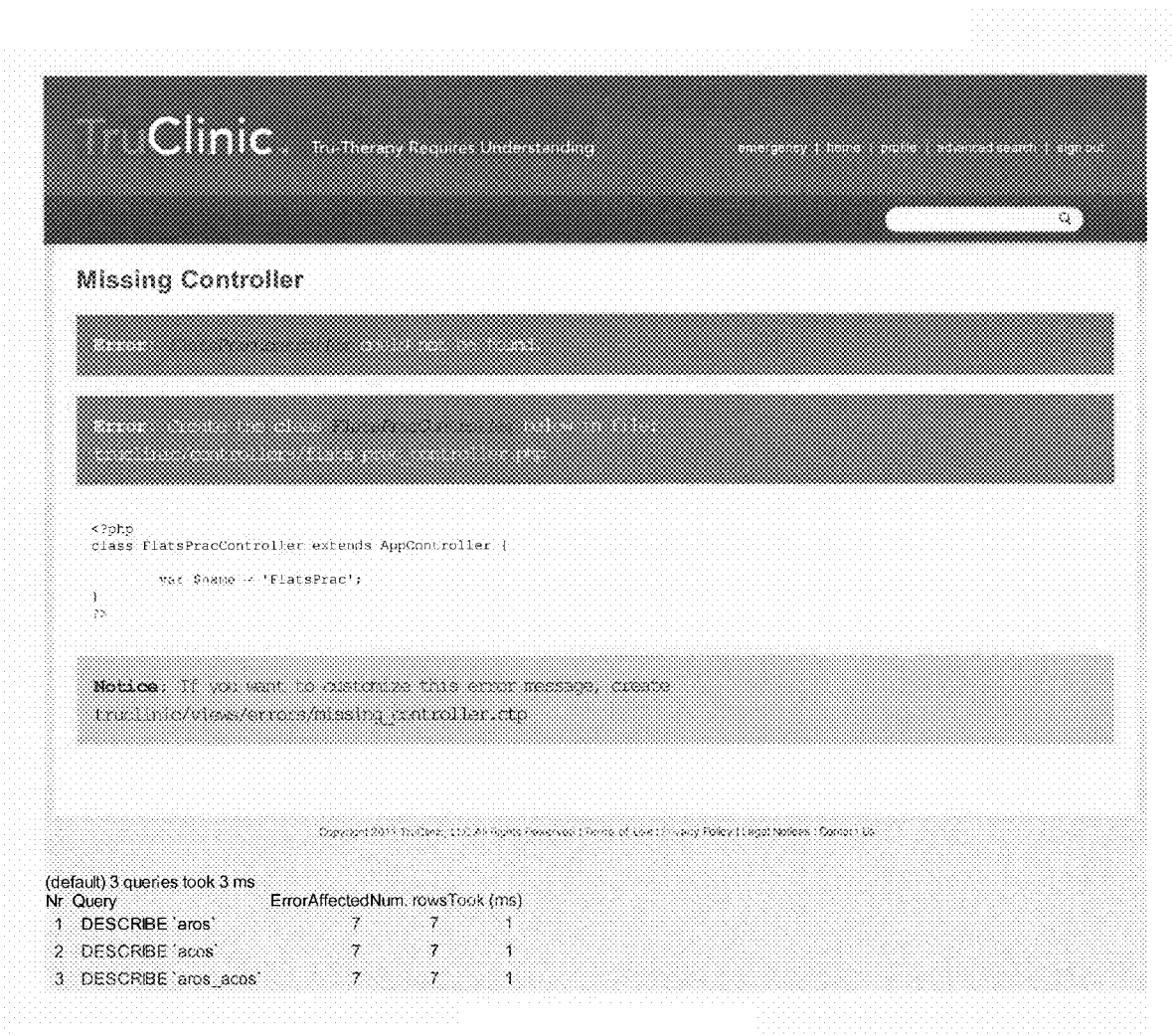
Figure 44:
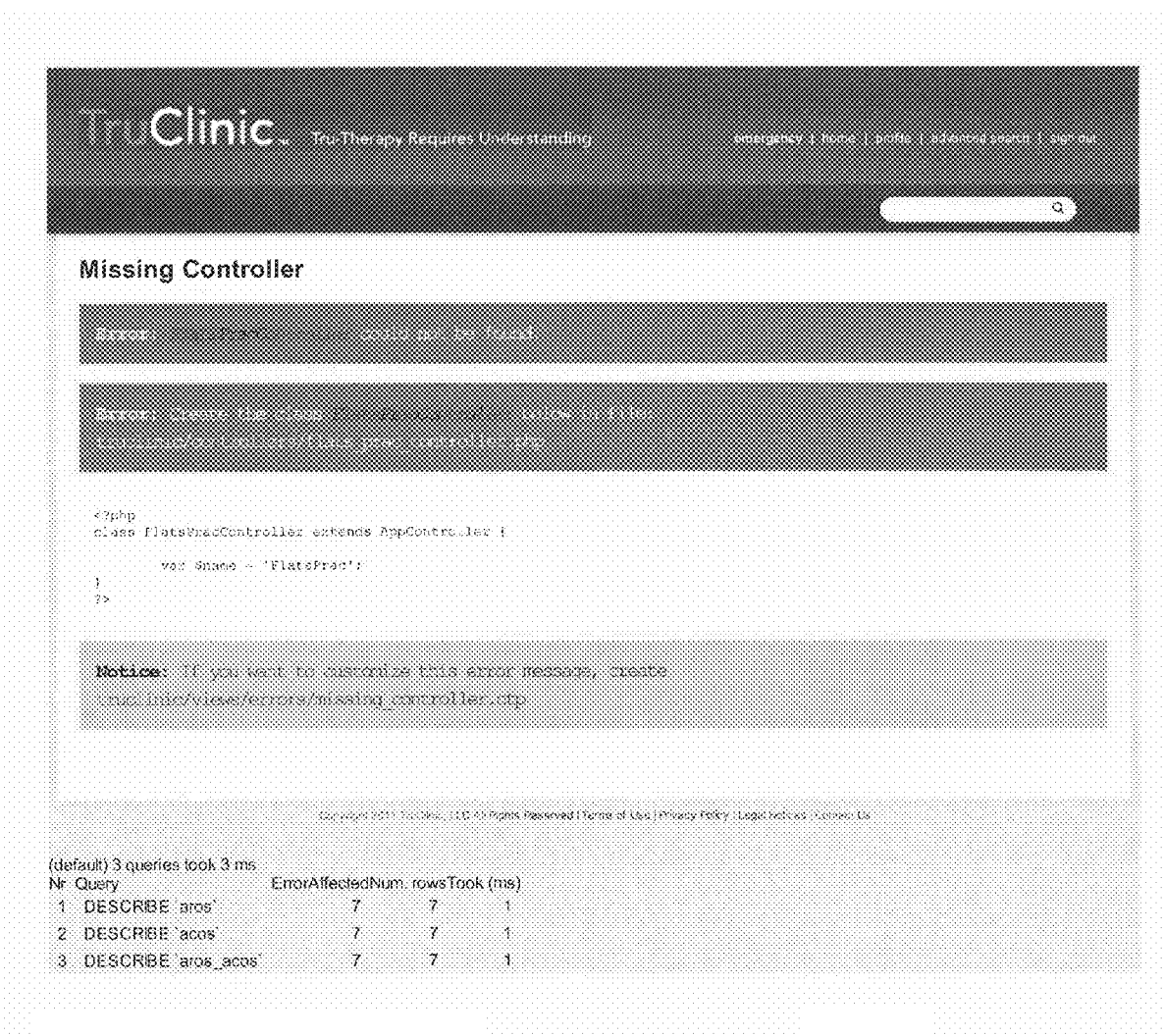
Figure 45:
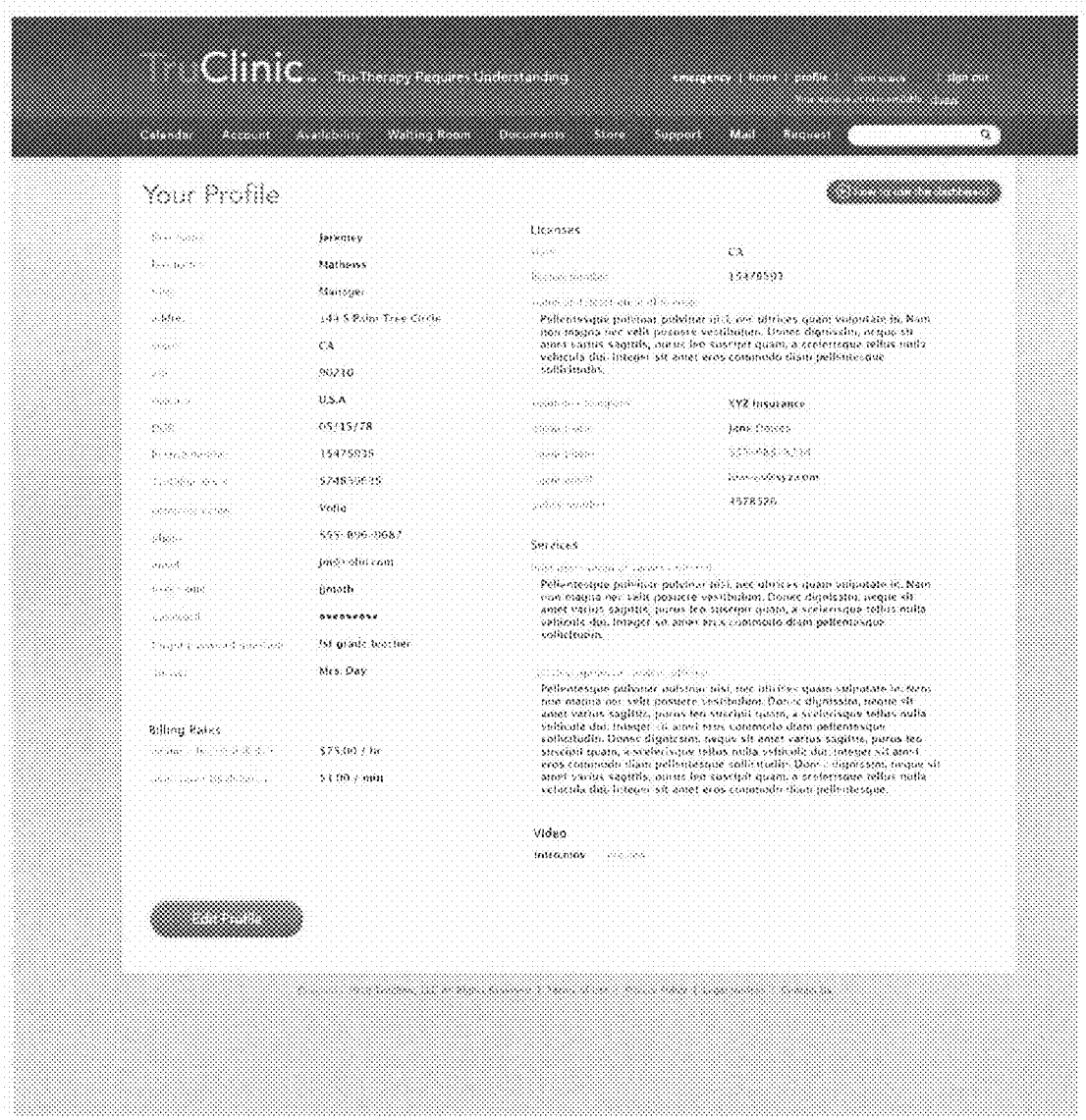
Figure 46:
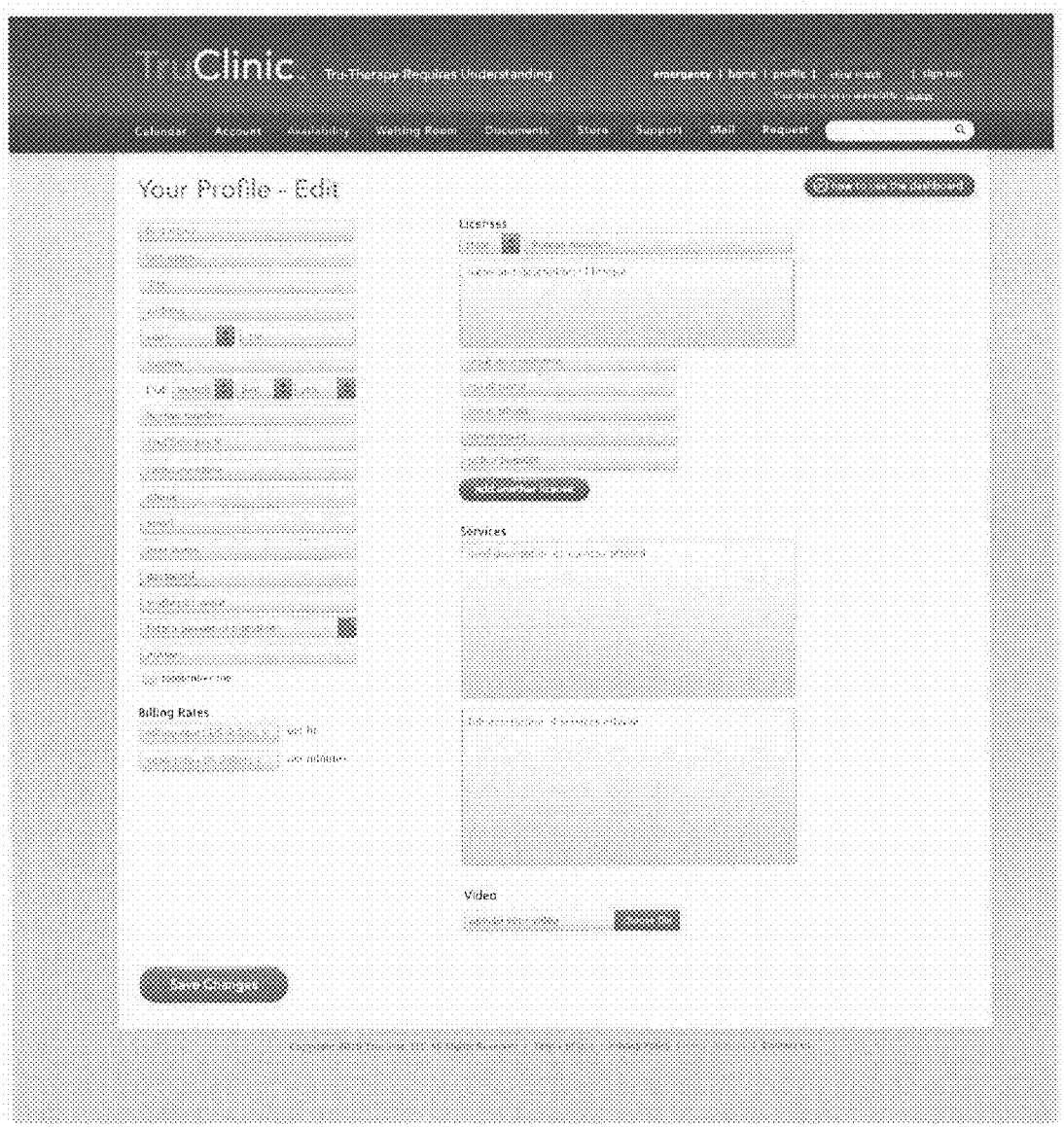
Figure 47:
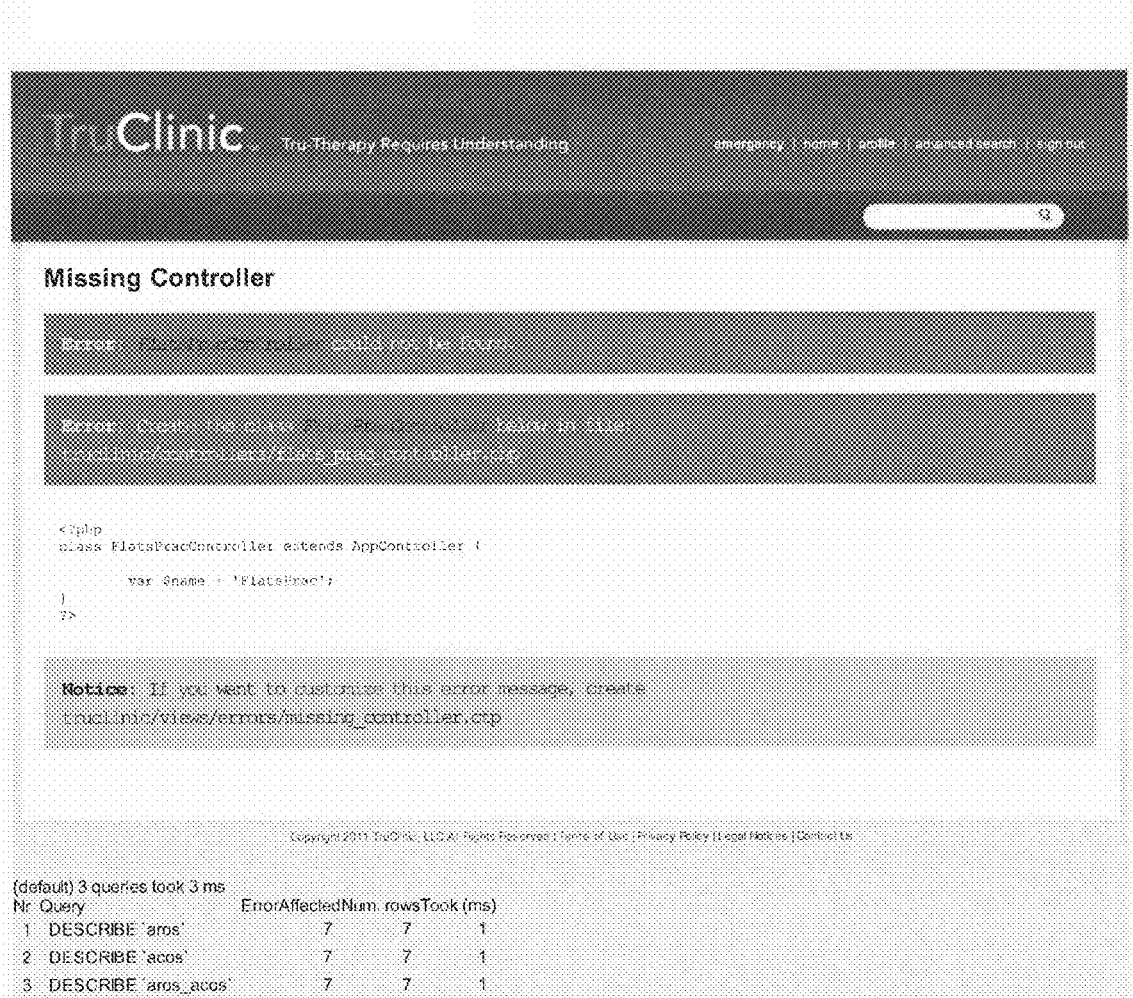
Figure 48:
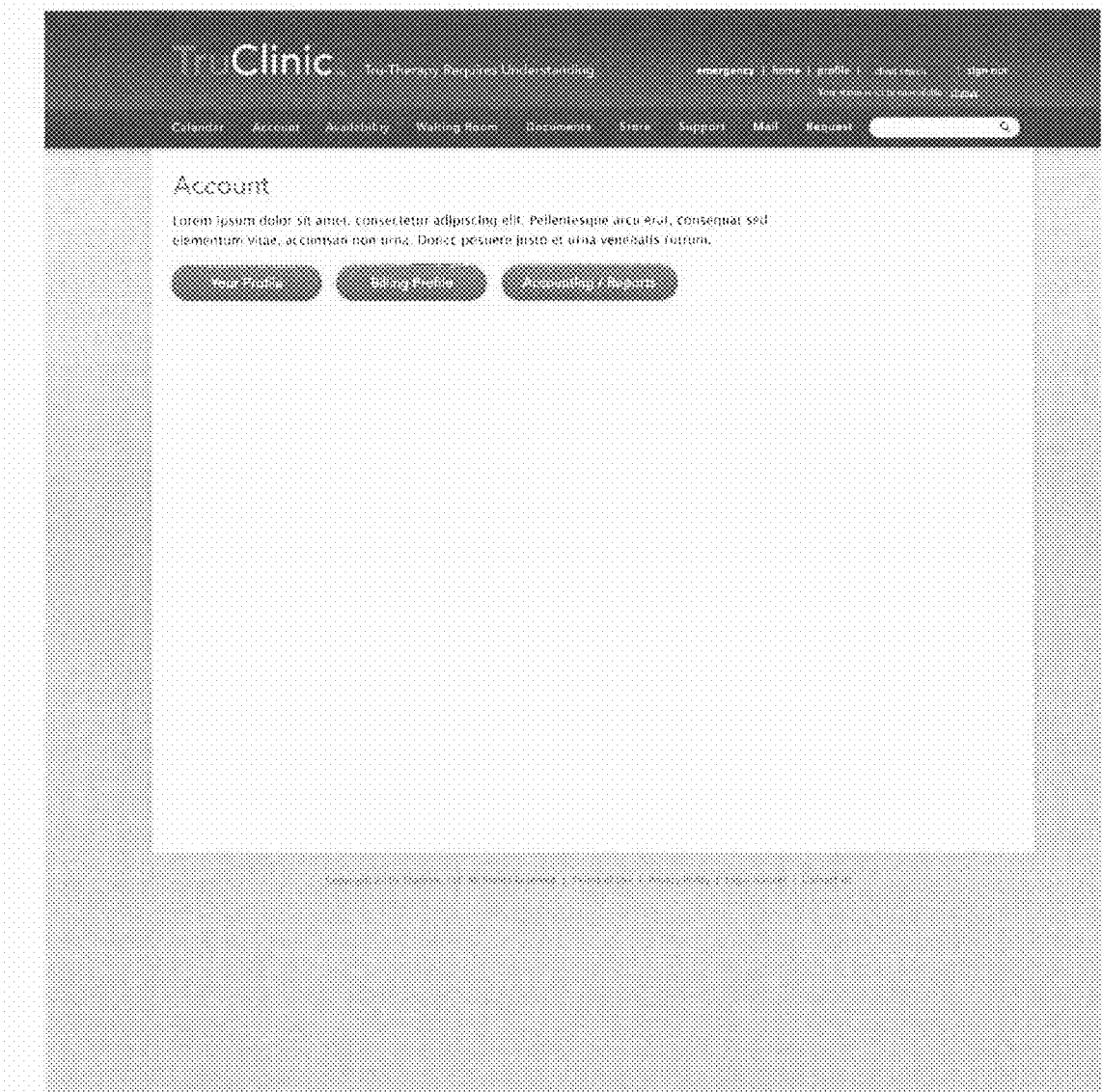
Figure 49:
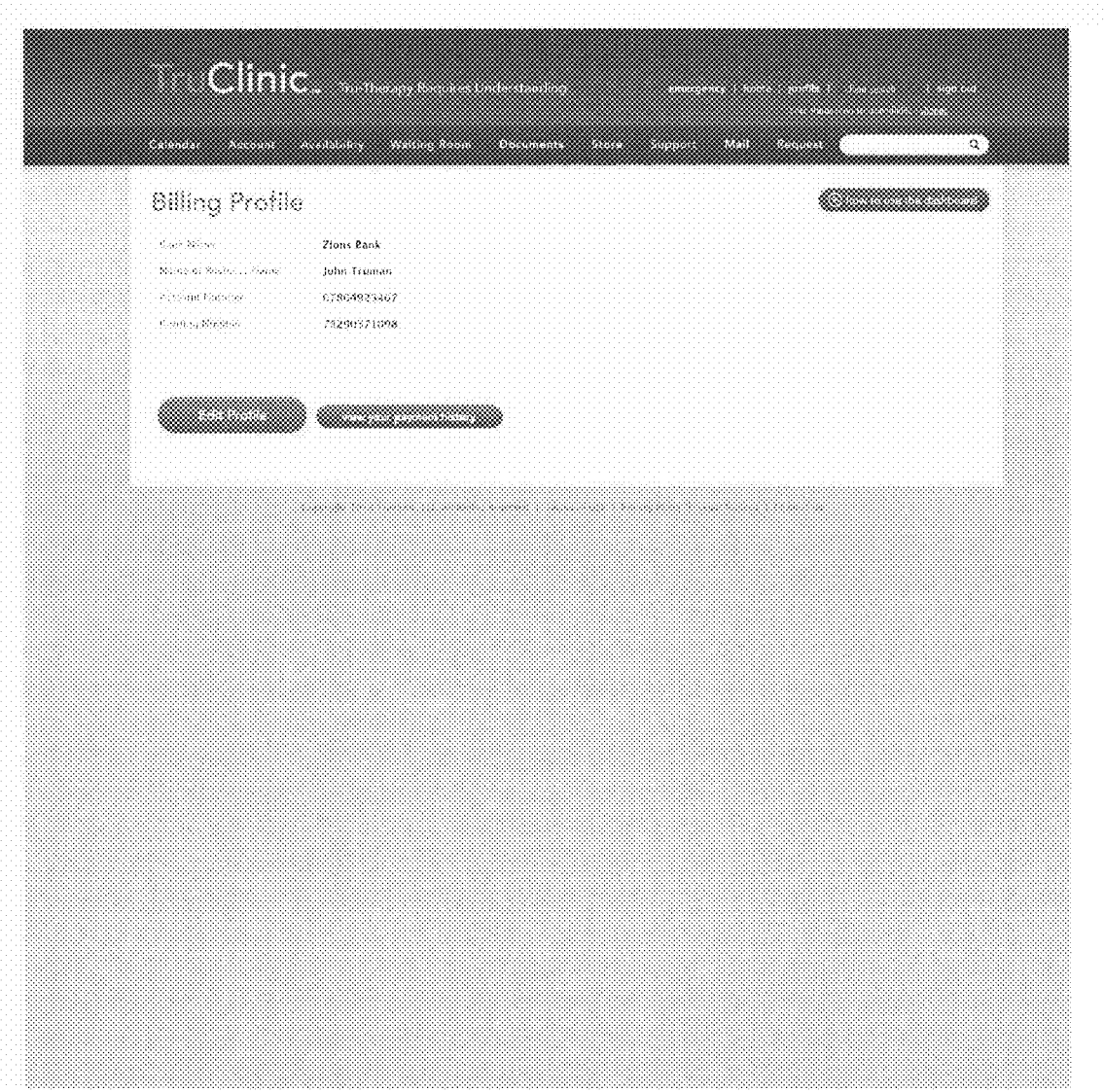
Figure 50:
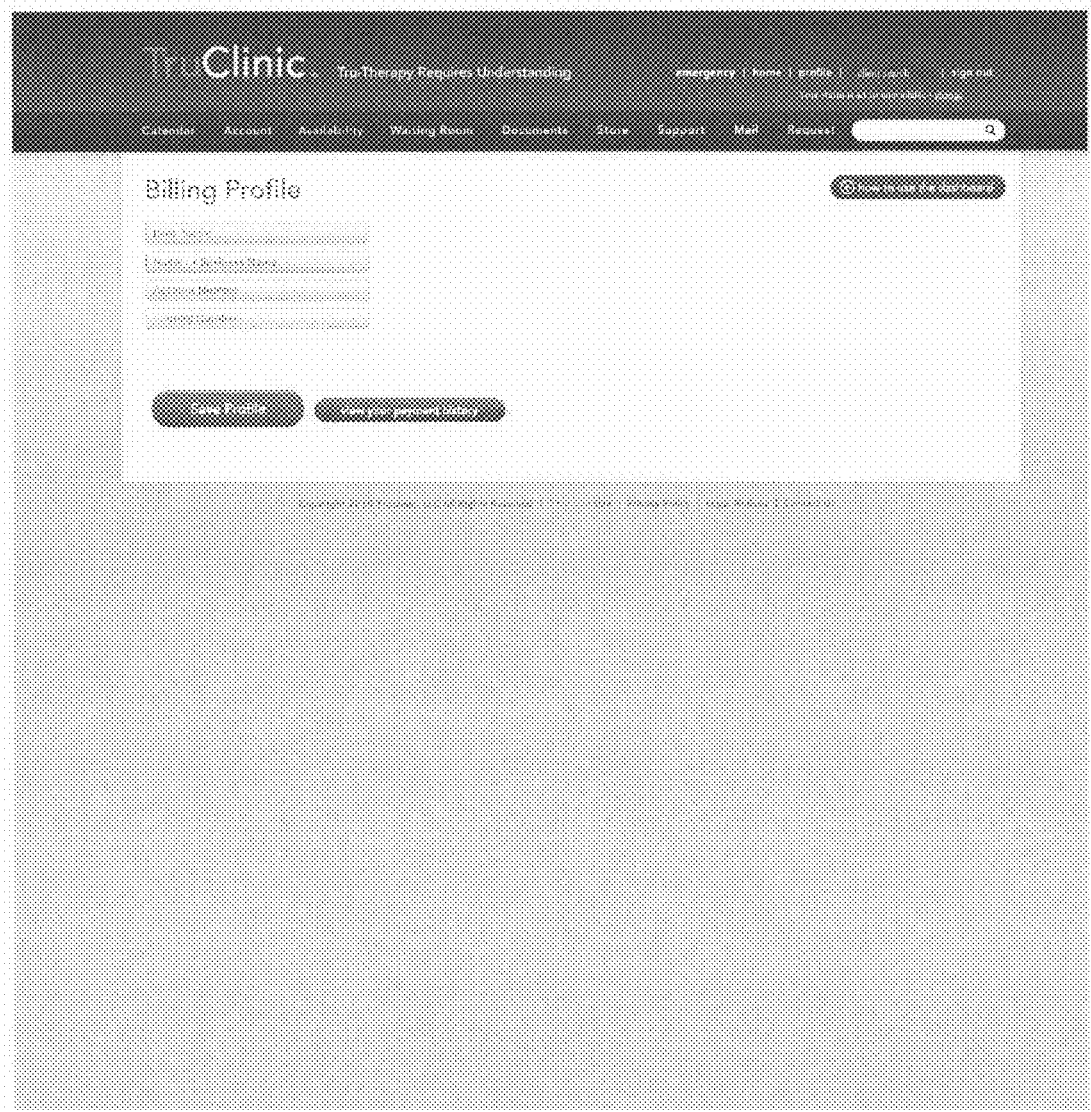
Figure 51:
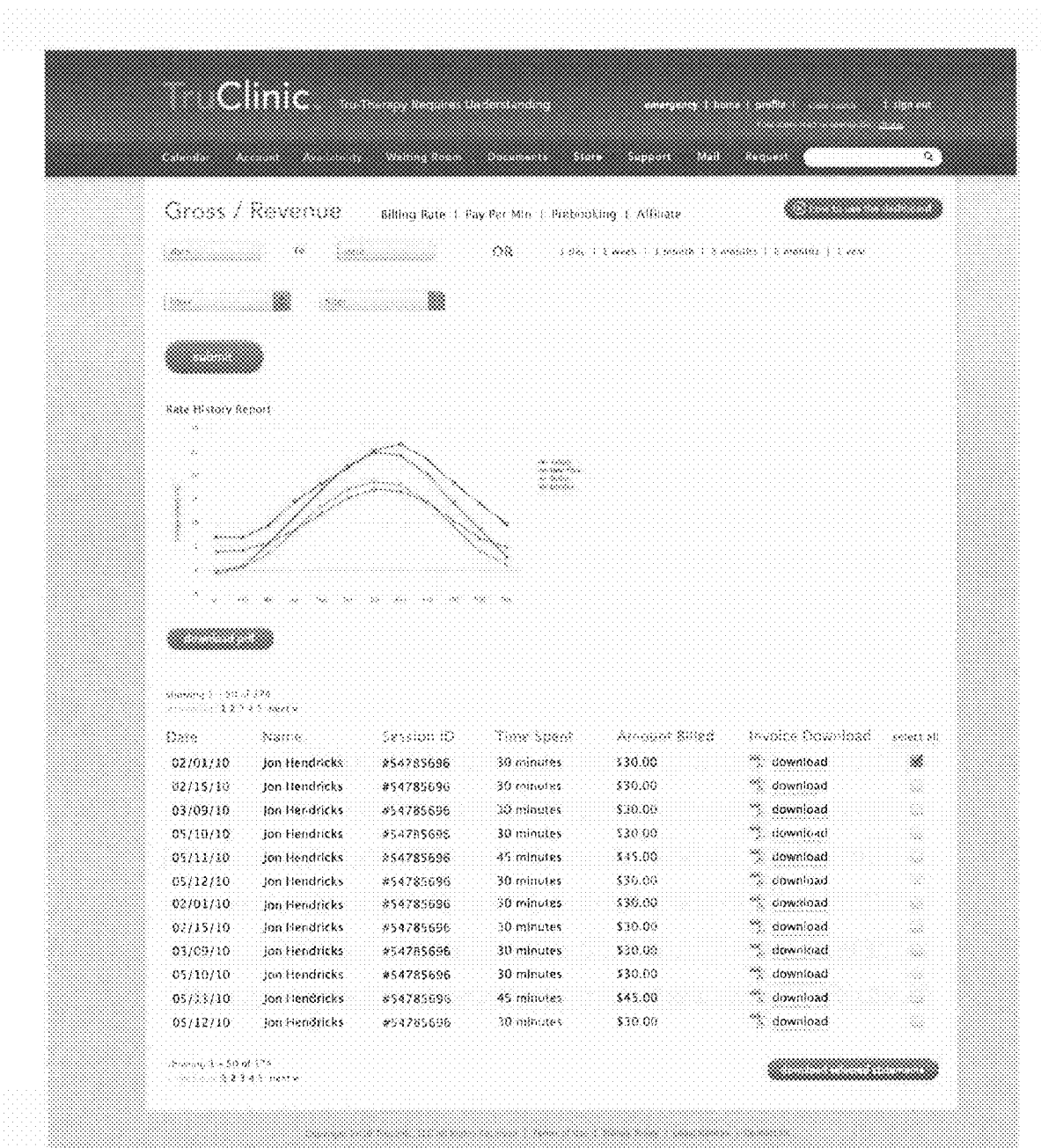
Figure 52:
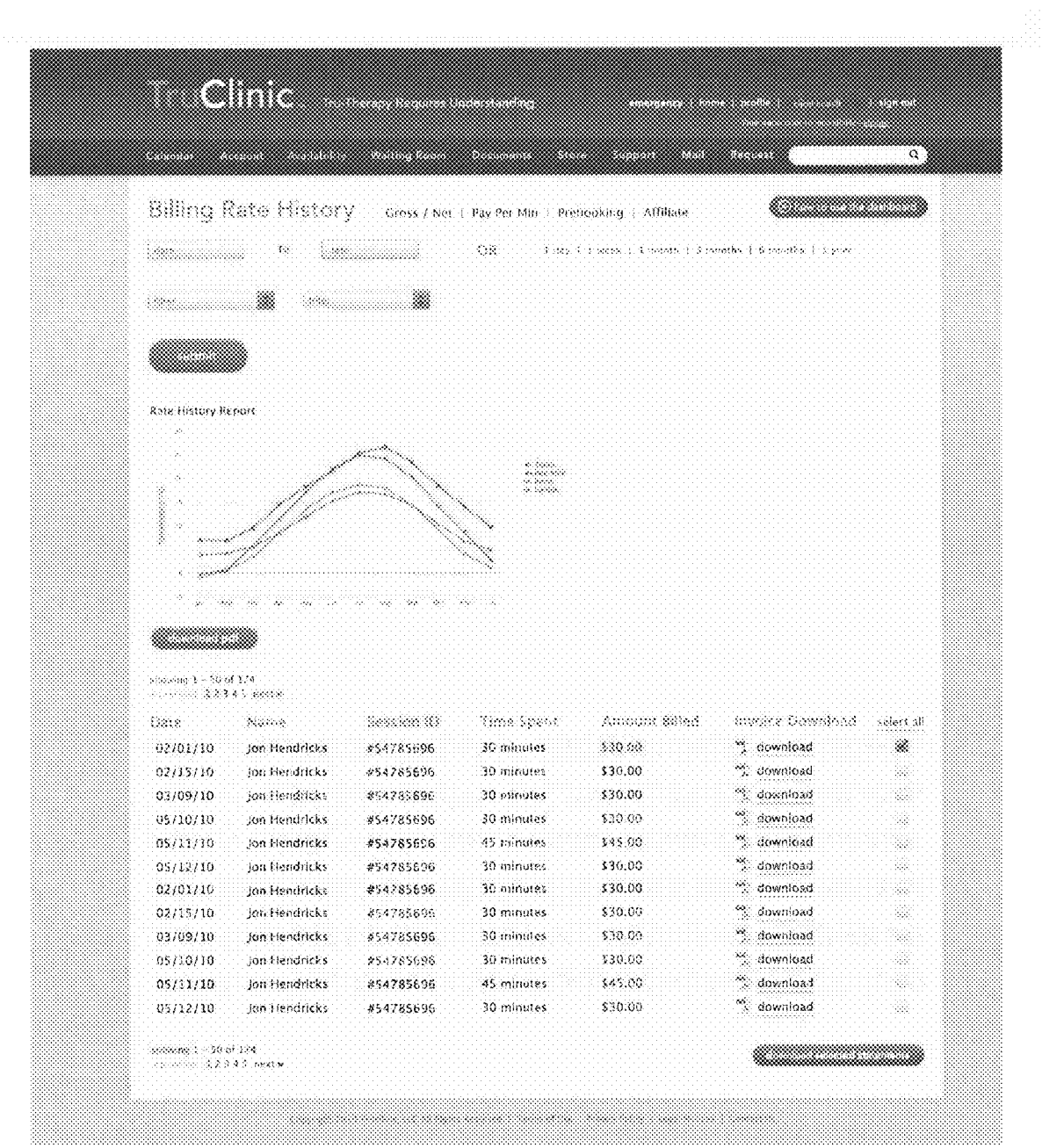
Figure 53:
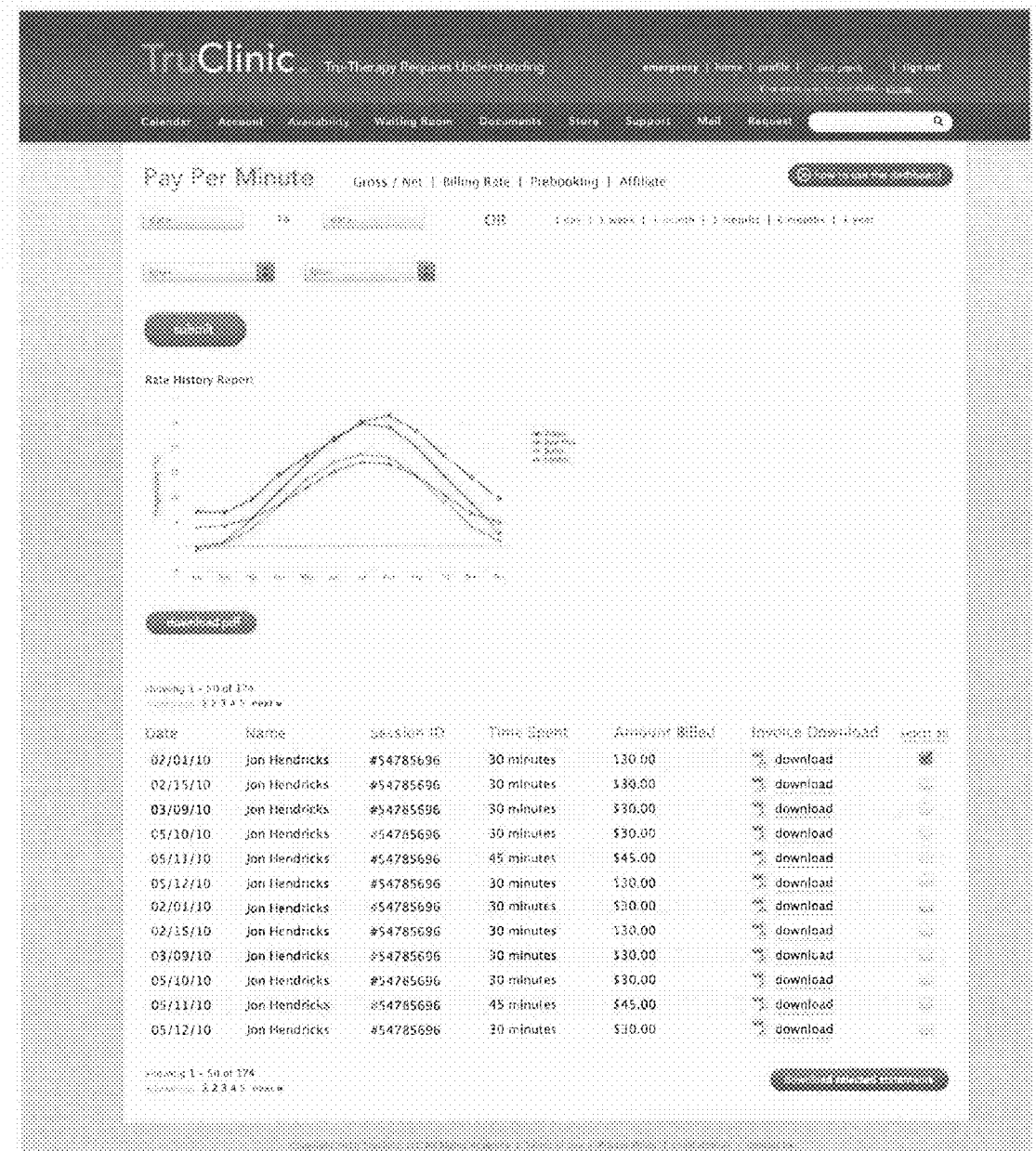
Figure 55:
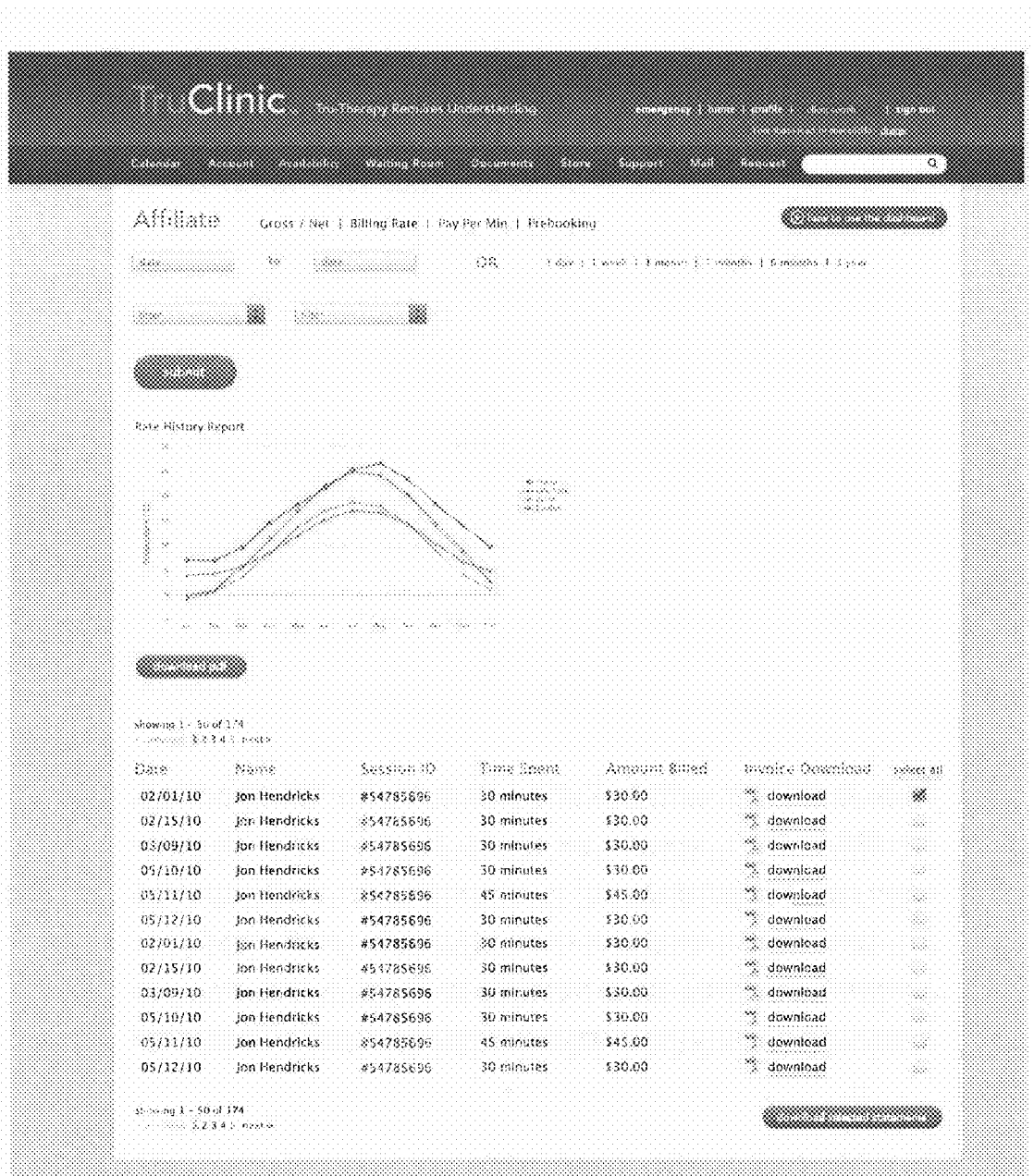
Figure 56:
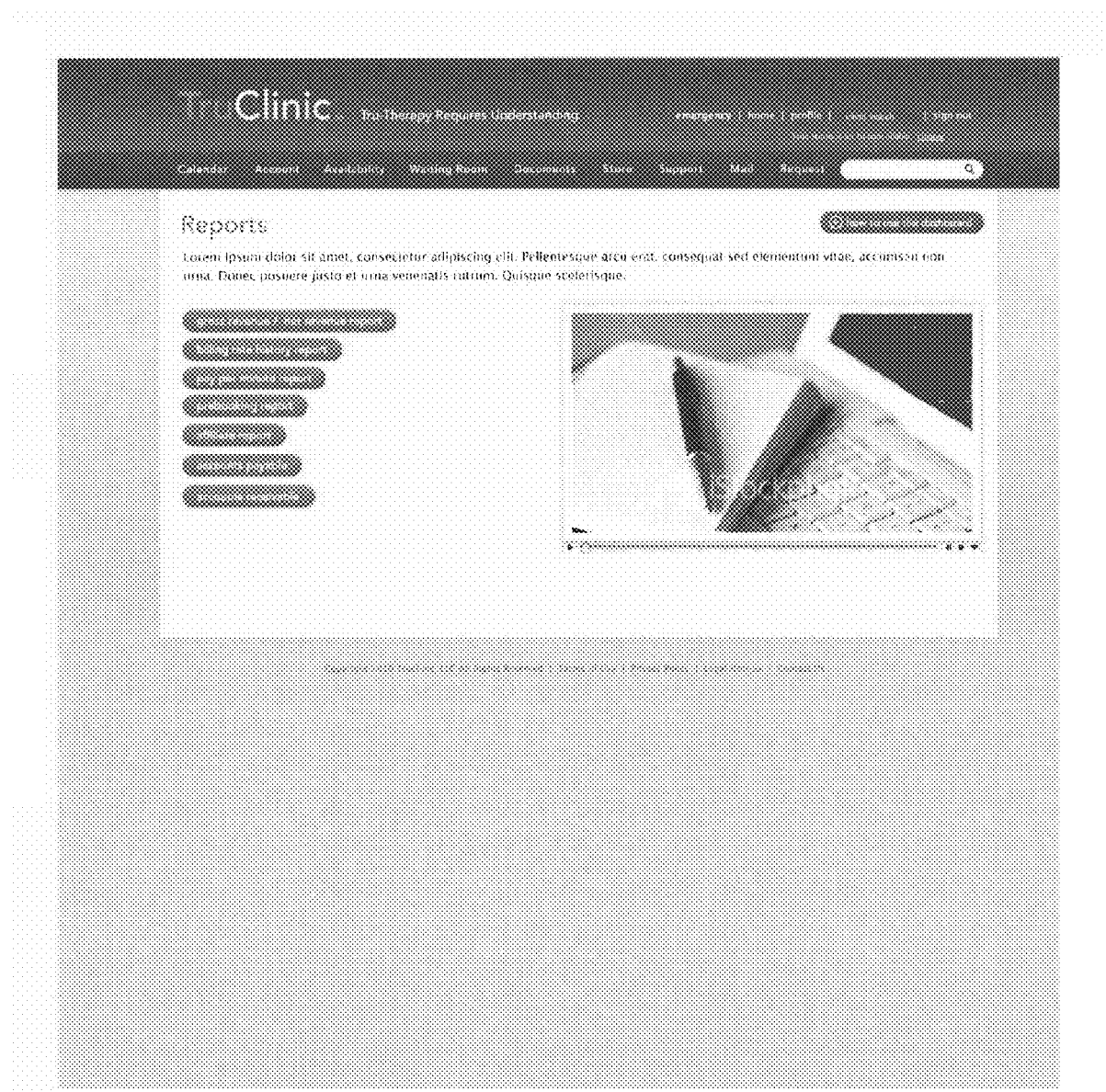
Figure 57:
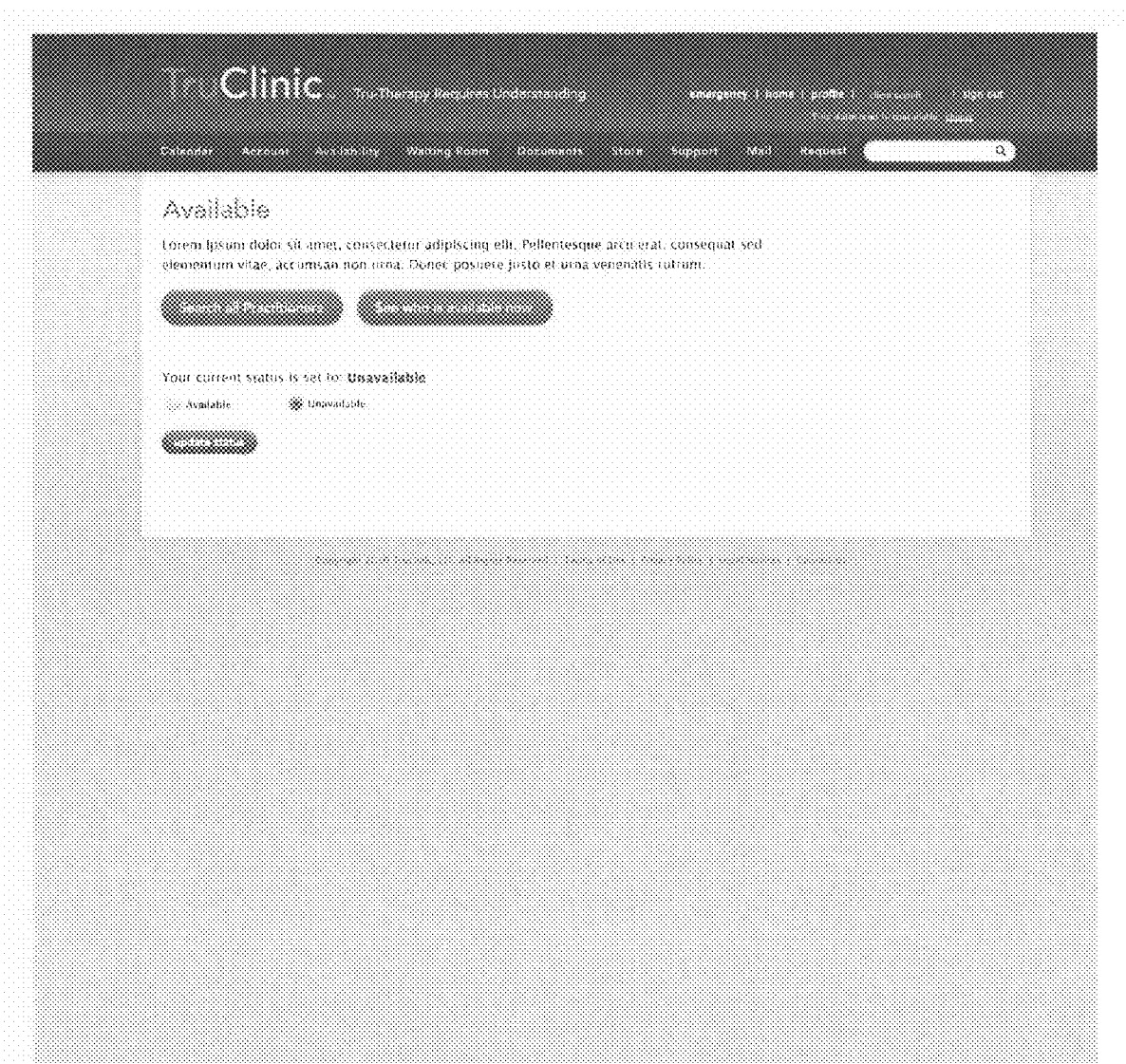
Figure 58:
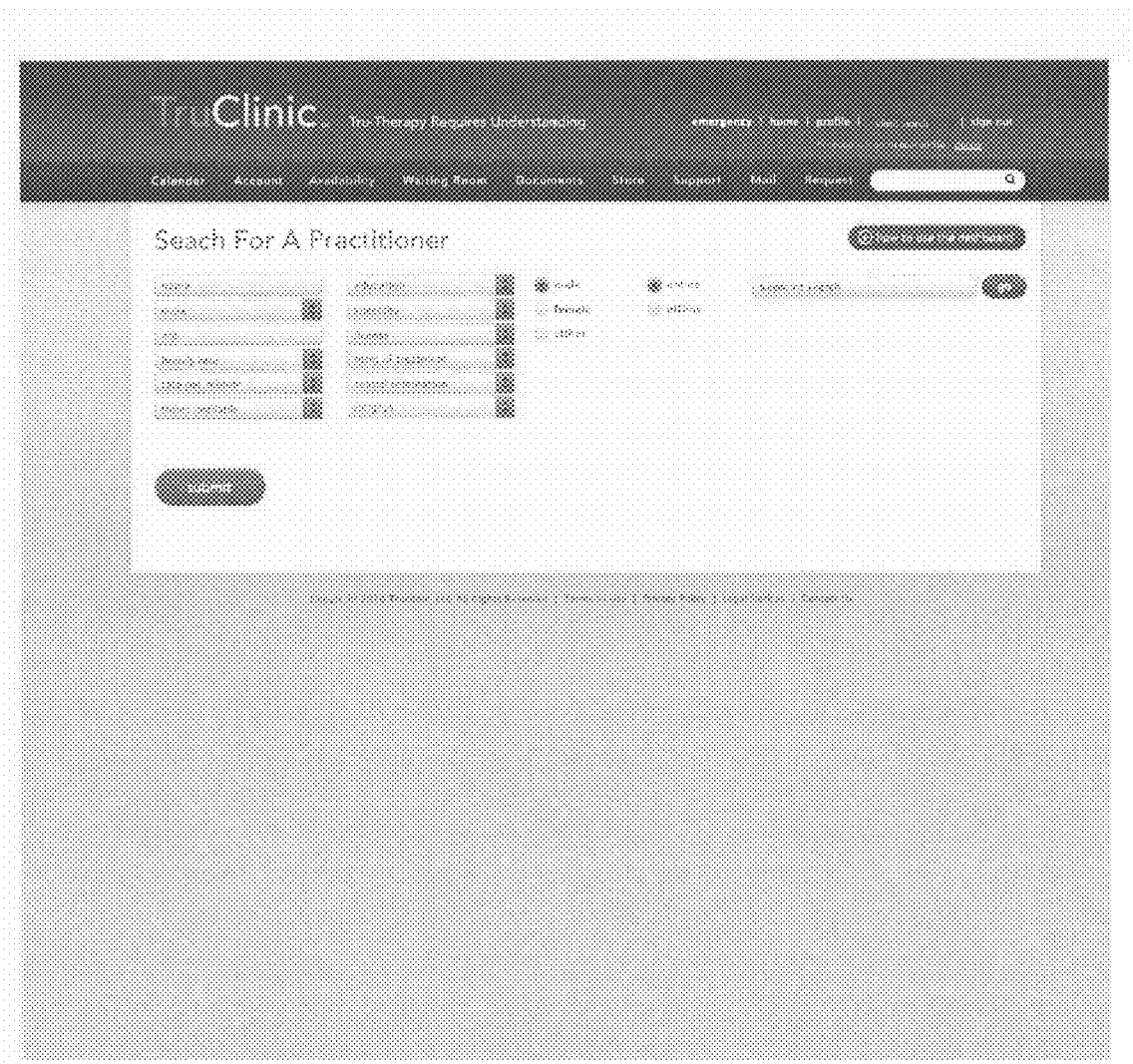
Figure 59:
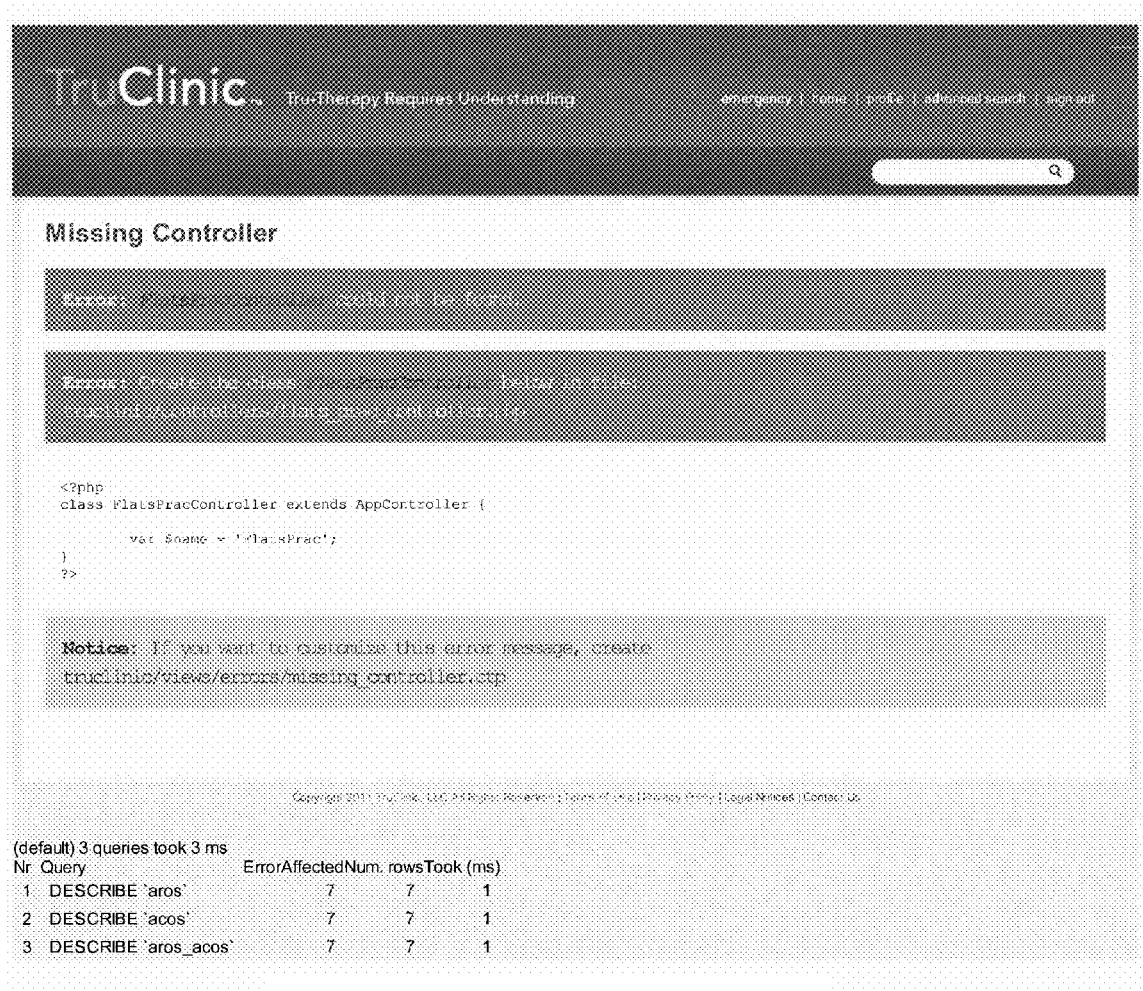
Figure 60:
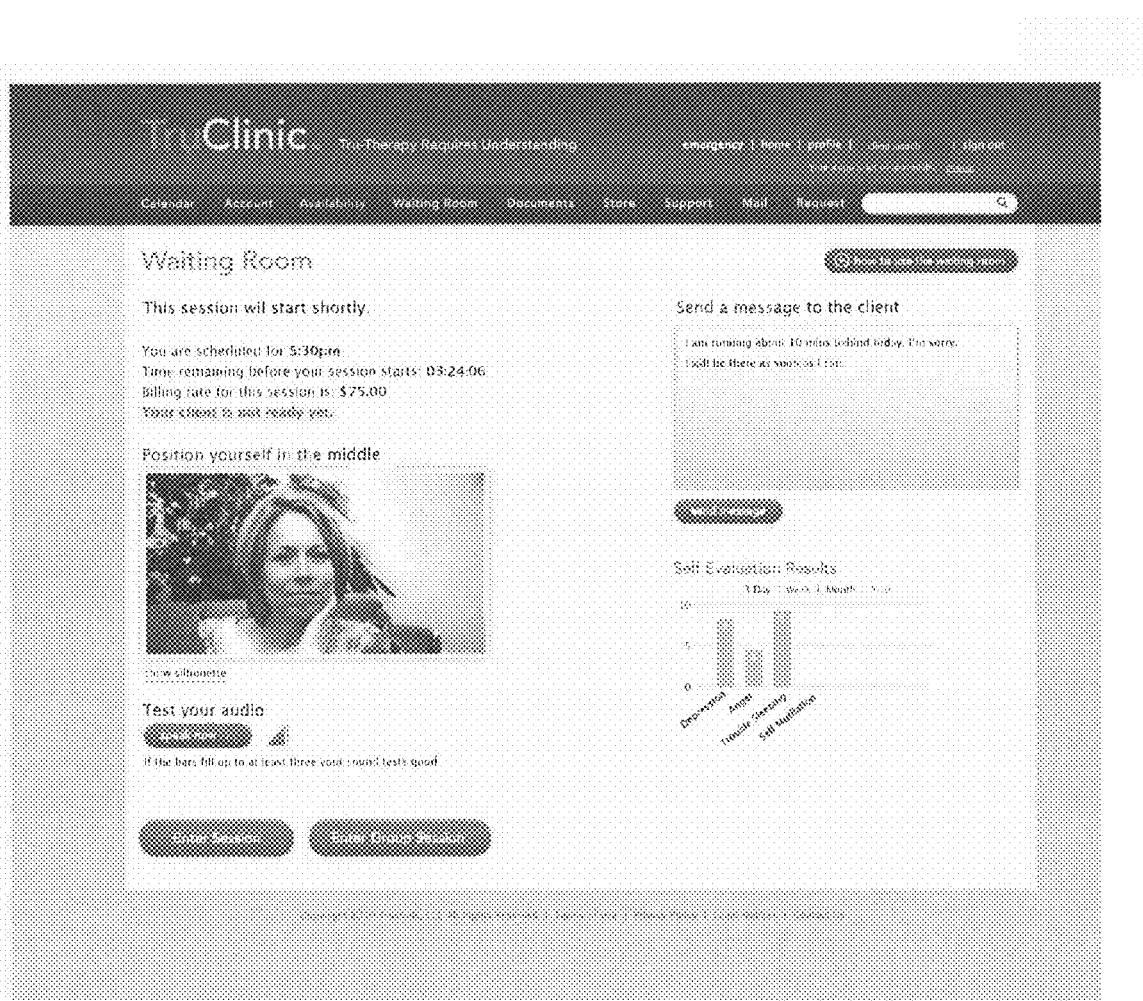
Figure 61:
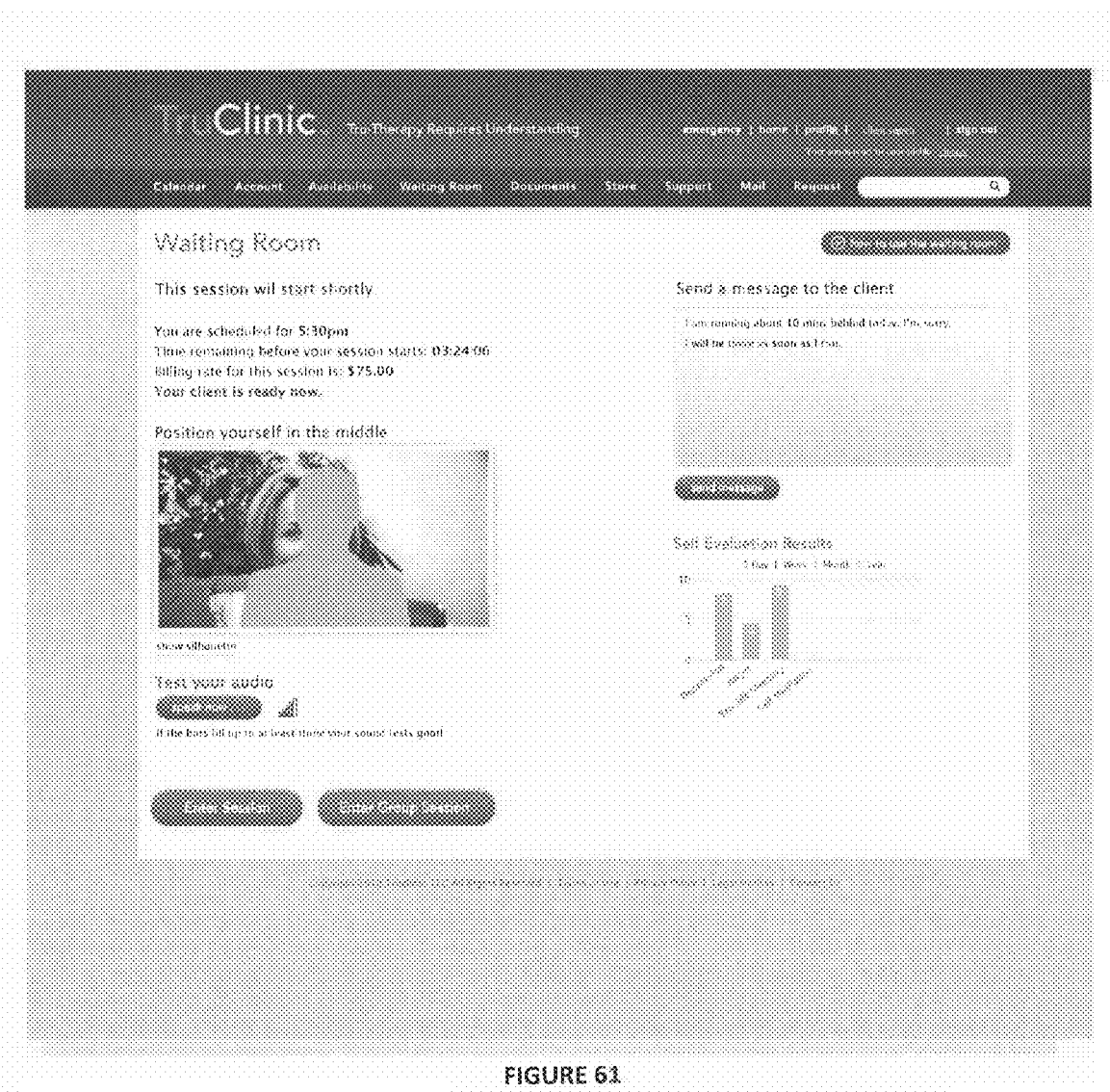
Figure 62:
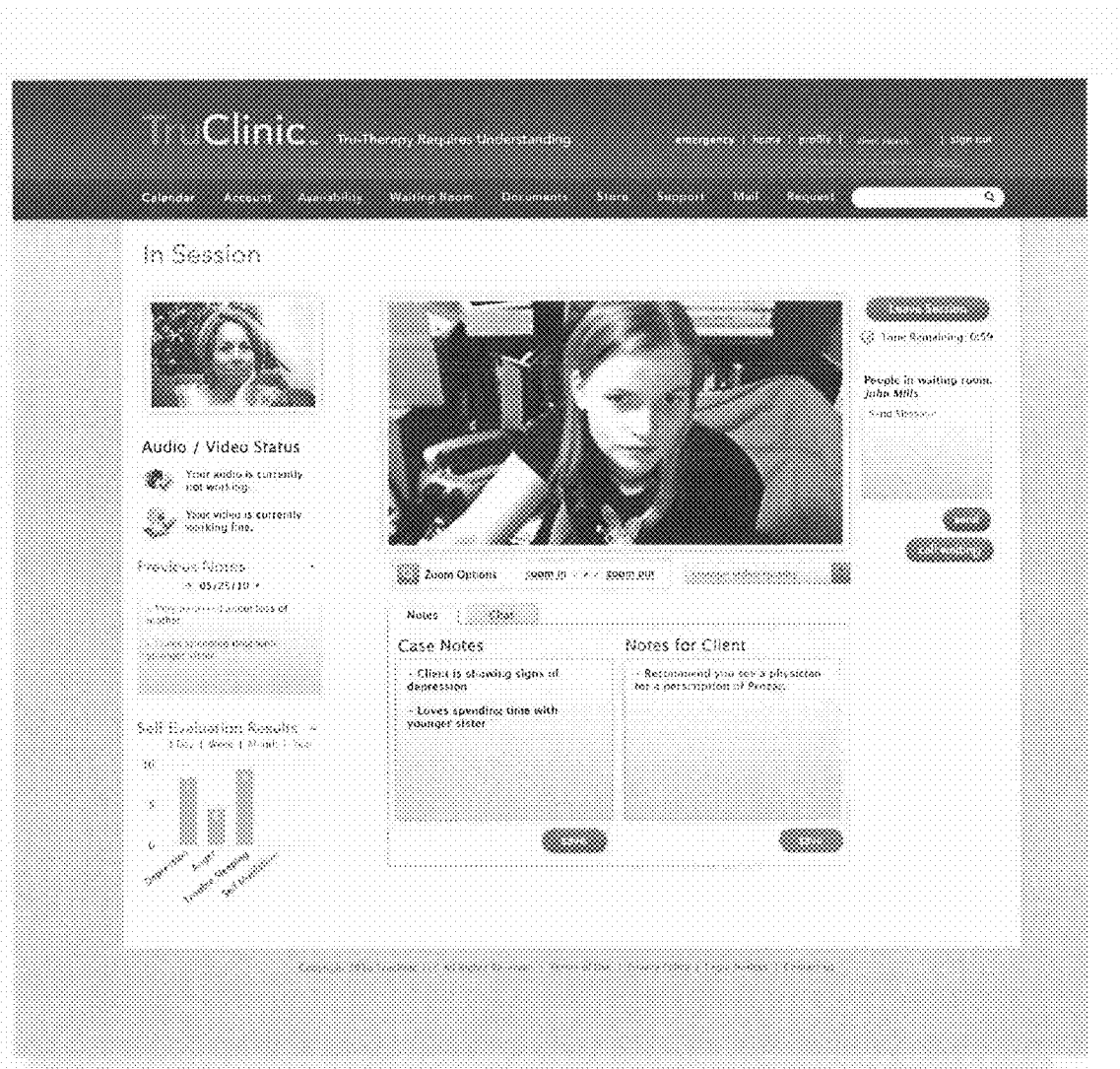
Figure 63:
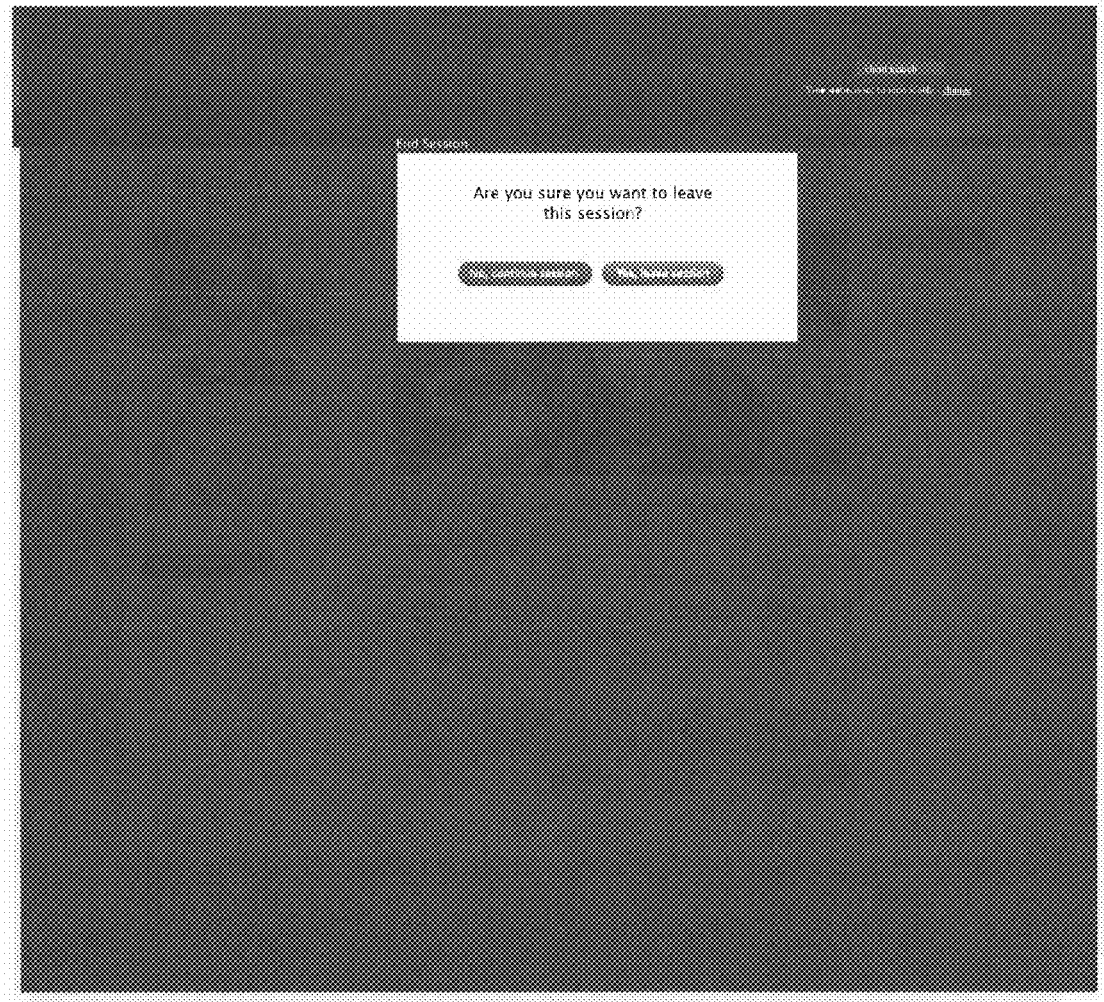
Figure 64:
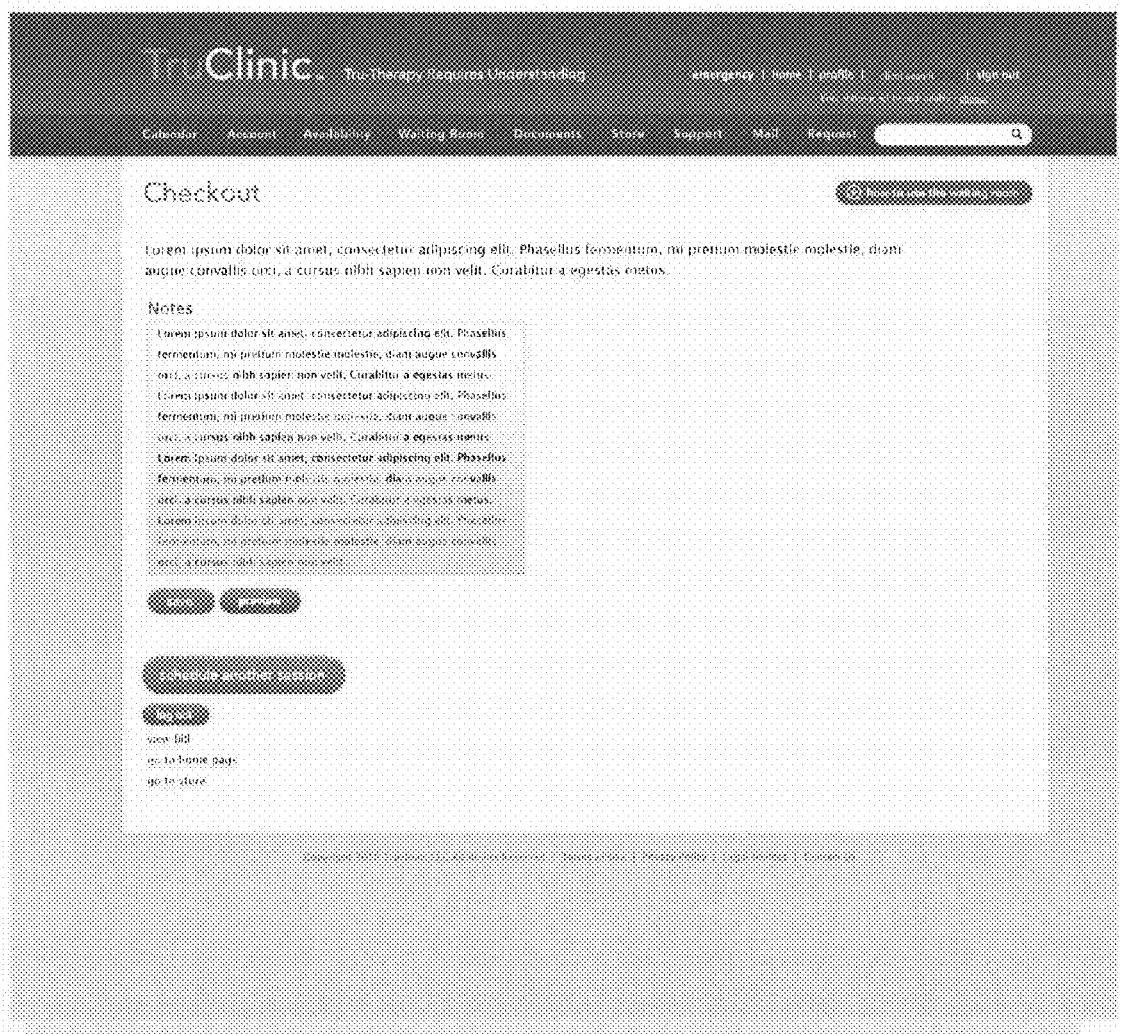
Figure 65:
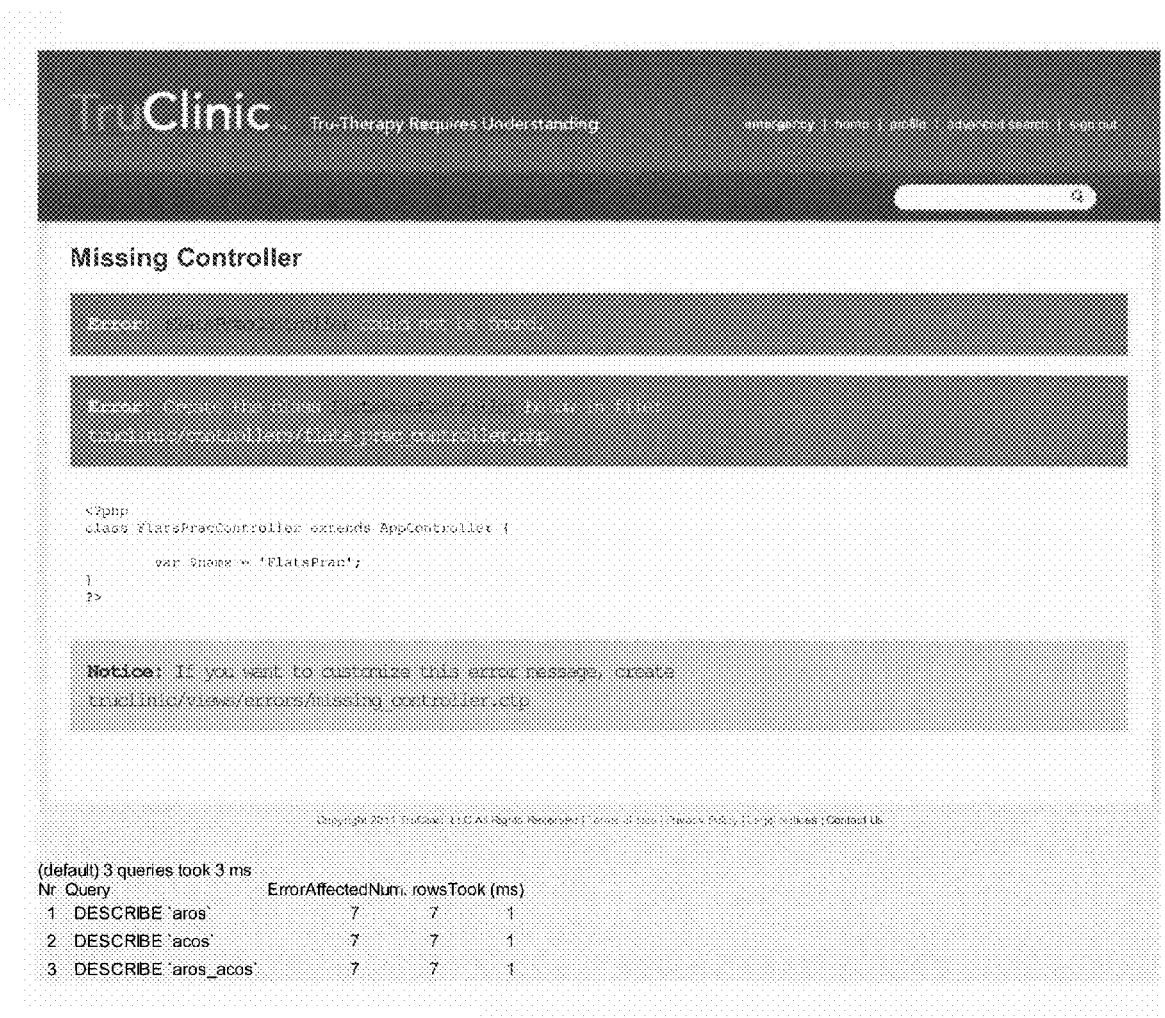
Figure 66:
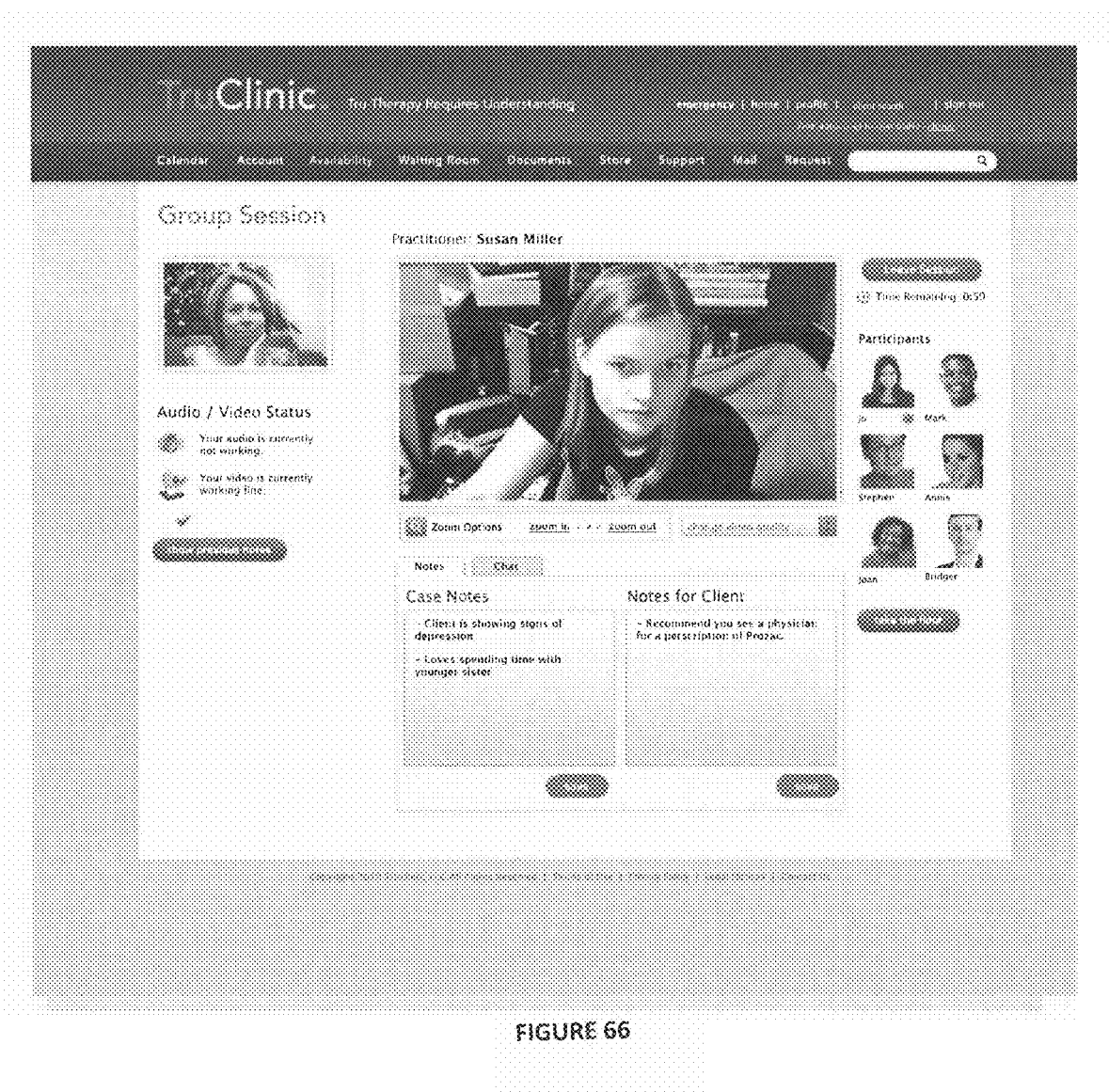
Figure 67:
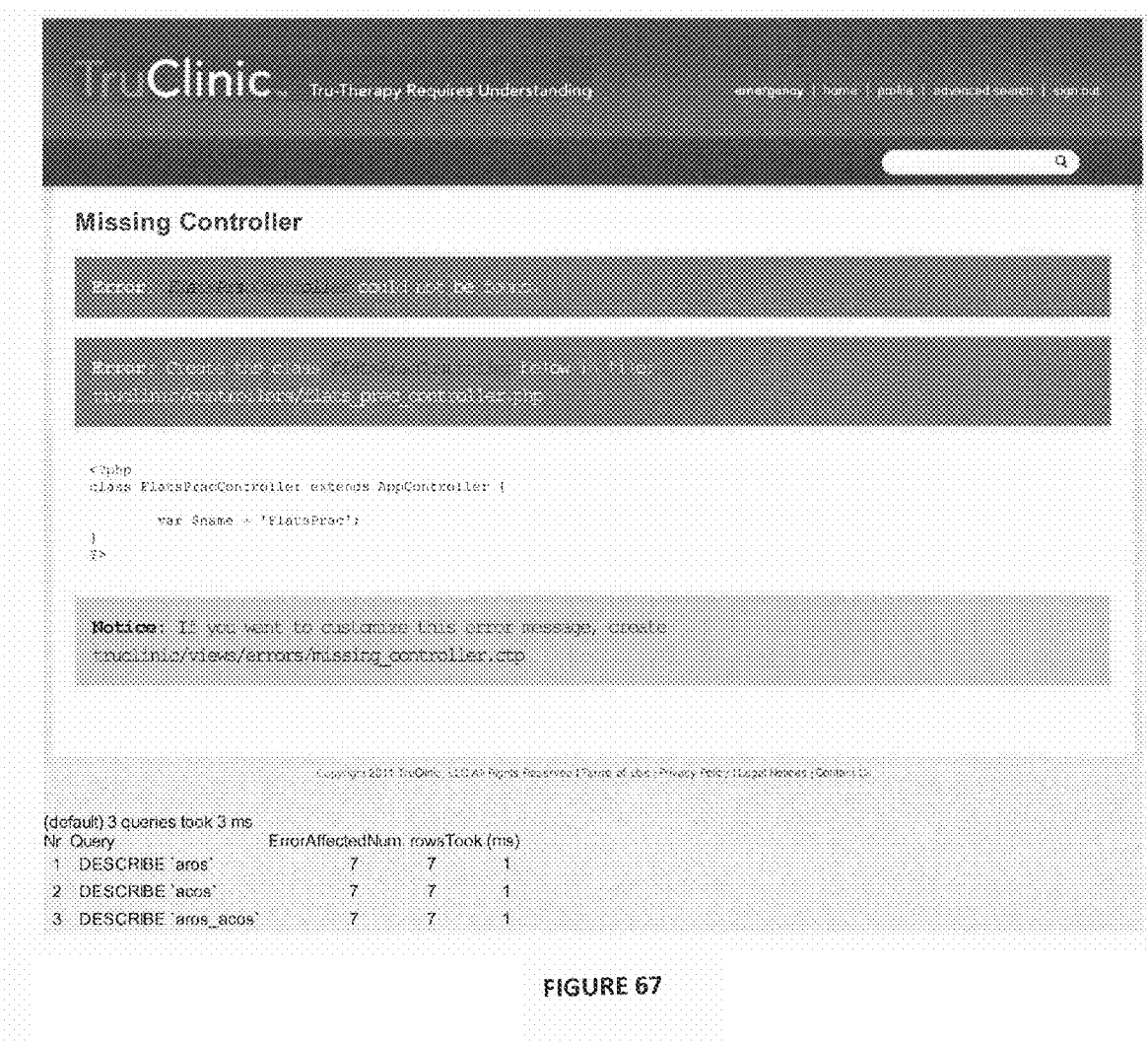
Figure 68:
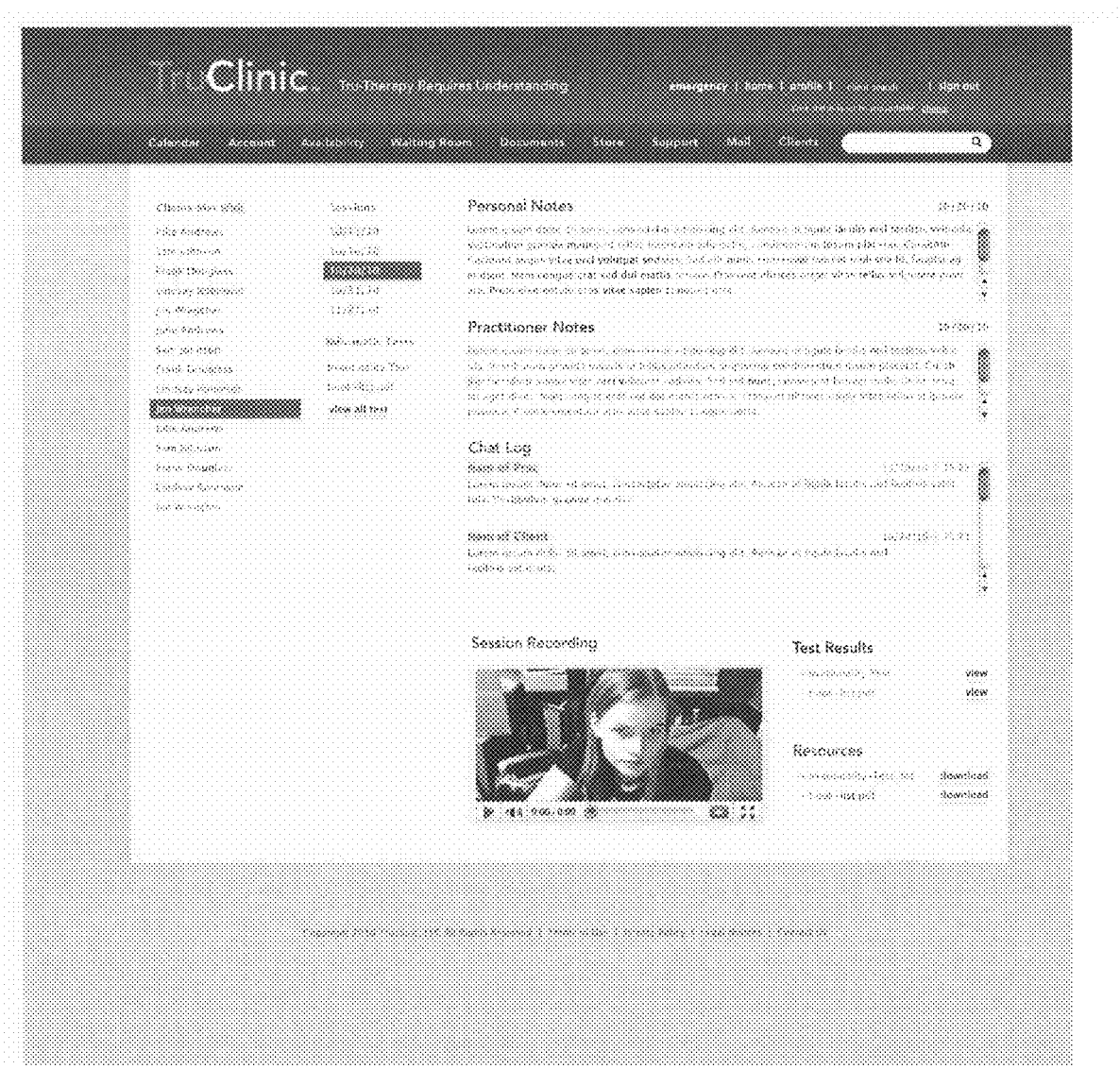
Figure 69:
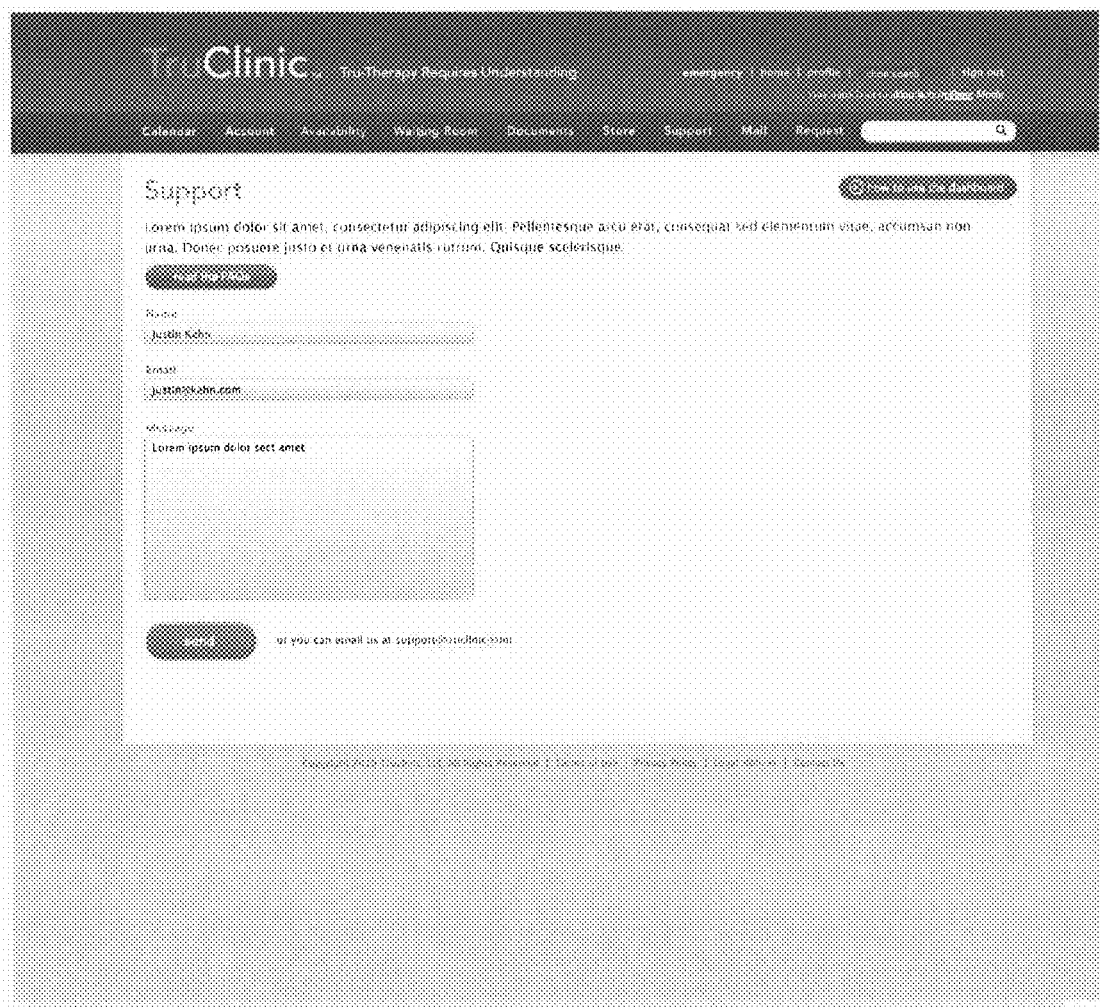
Figure 70:
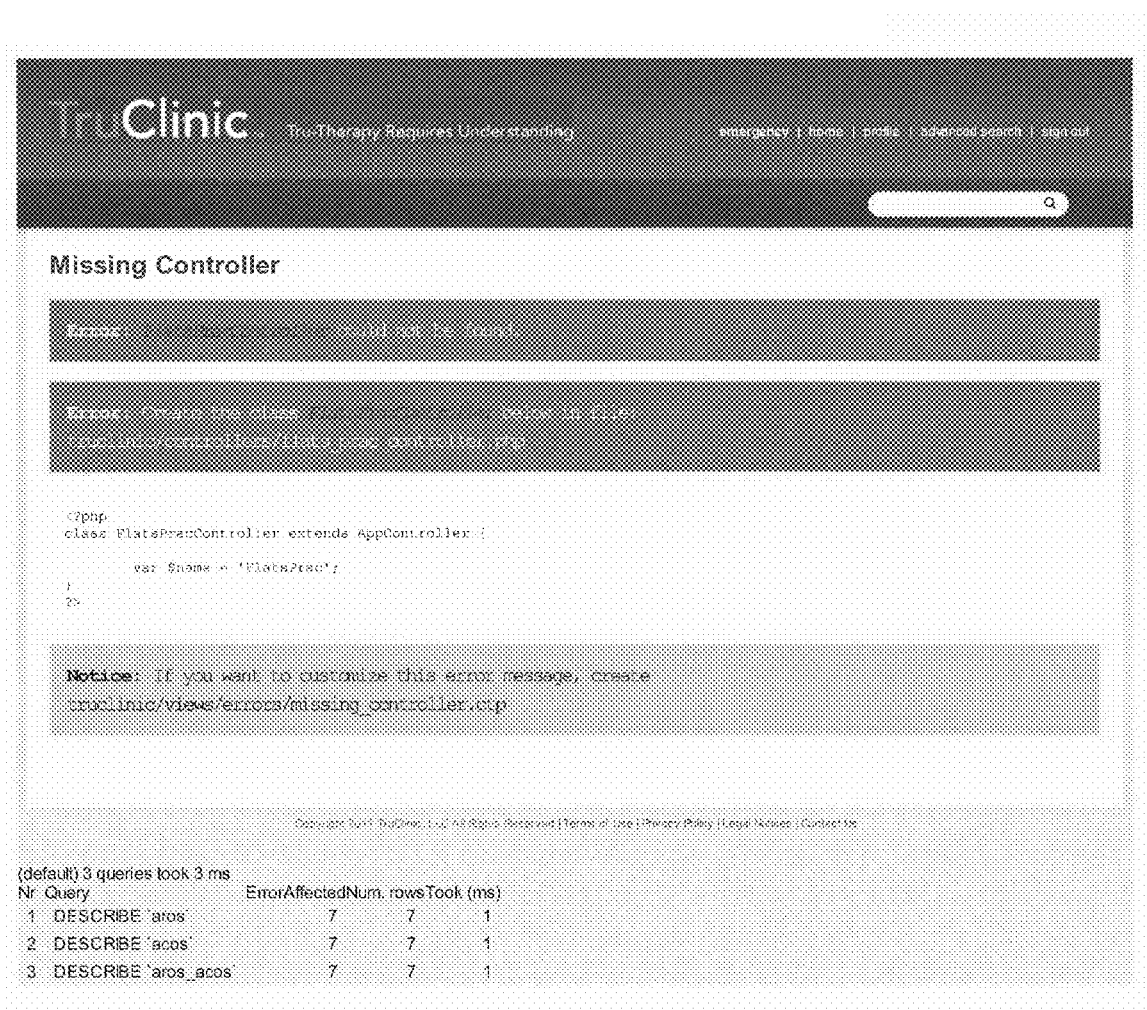
Figure 71:
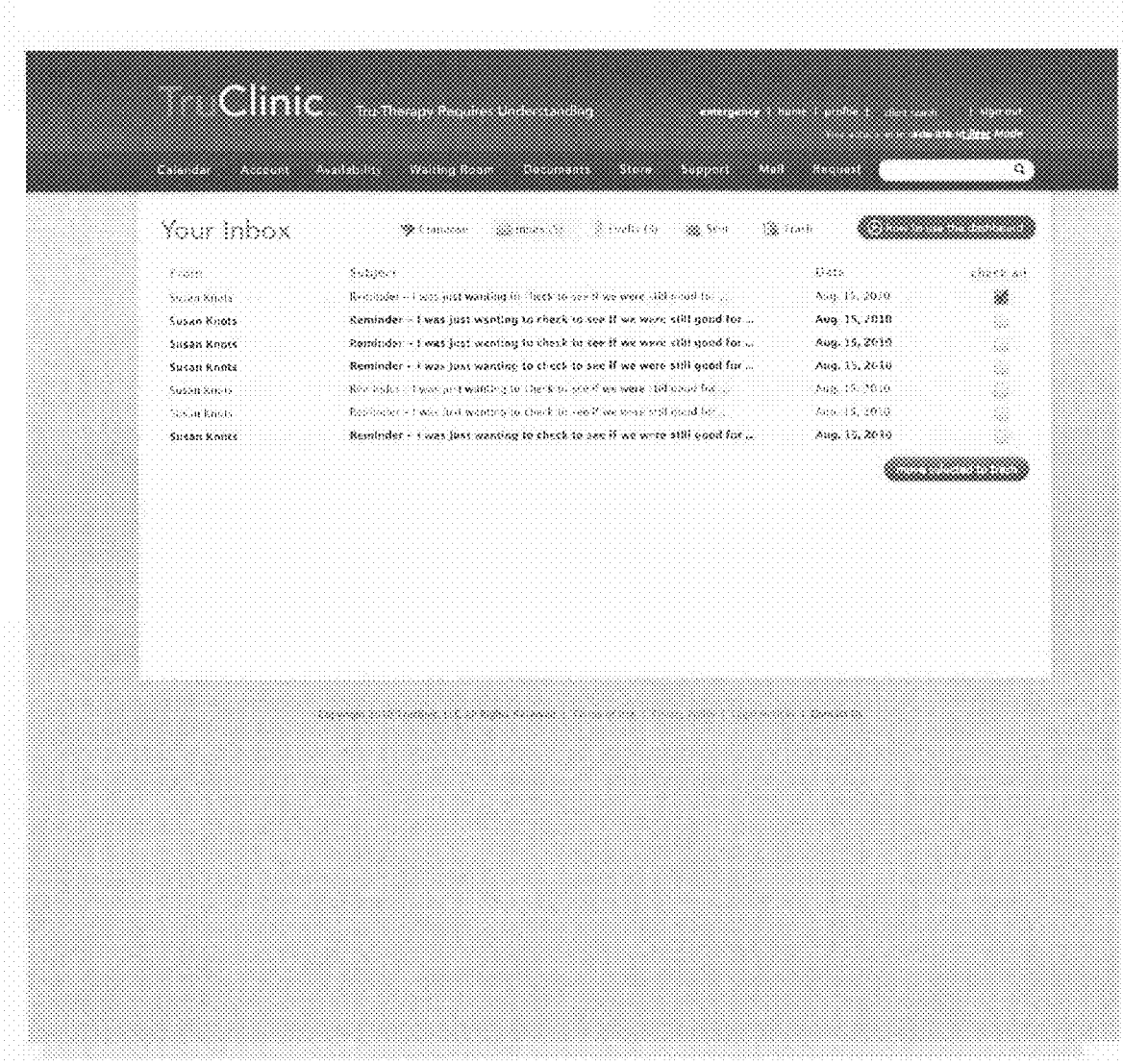
Figure 72:
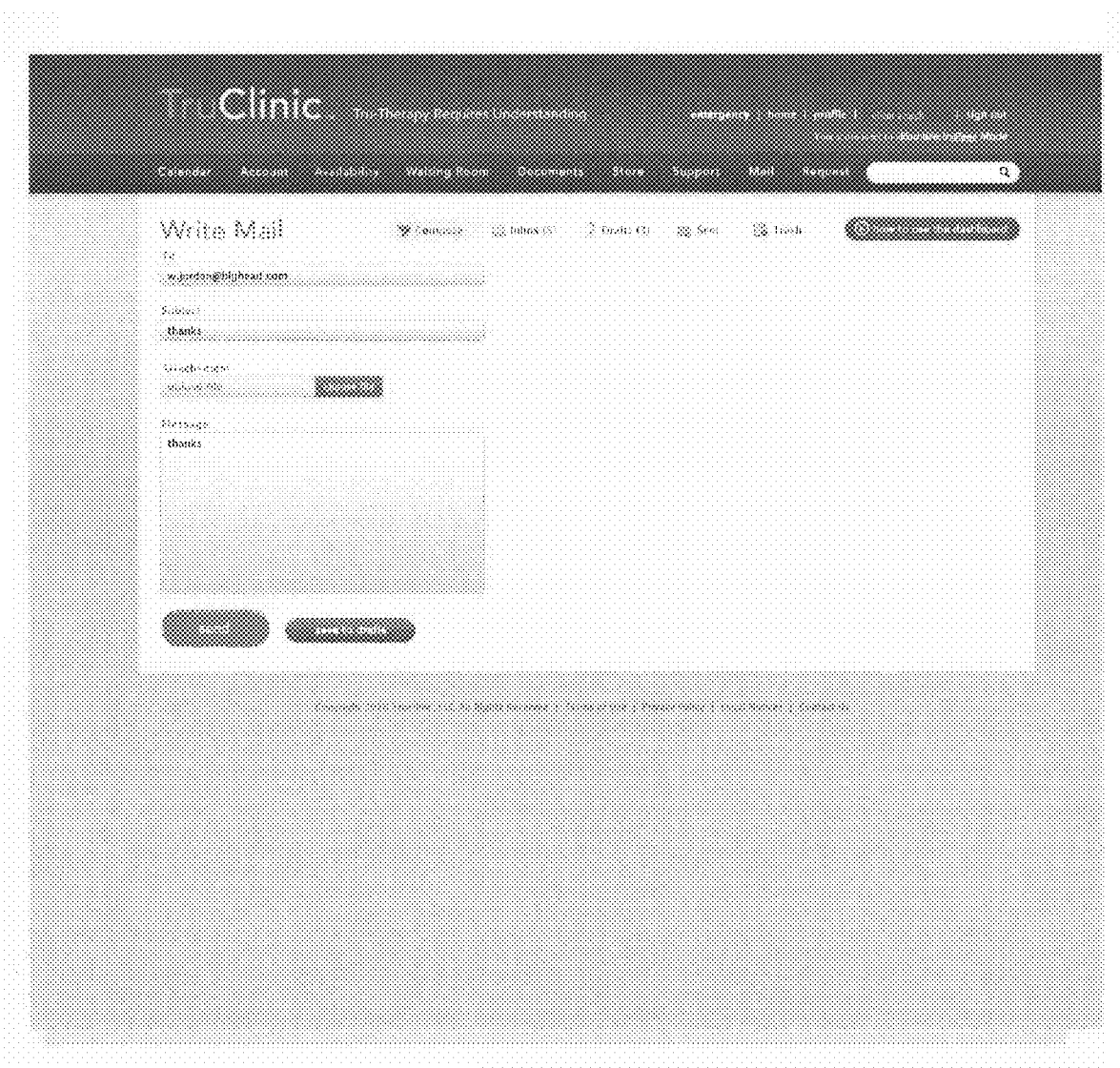
Figure 73:
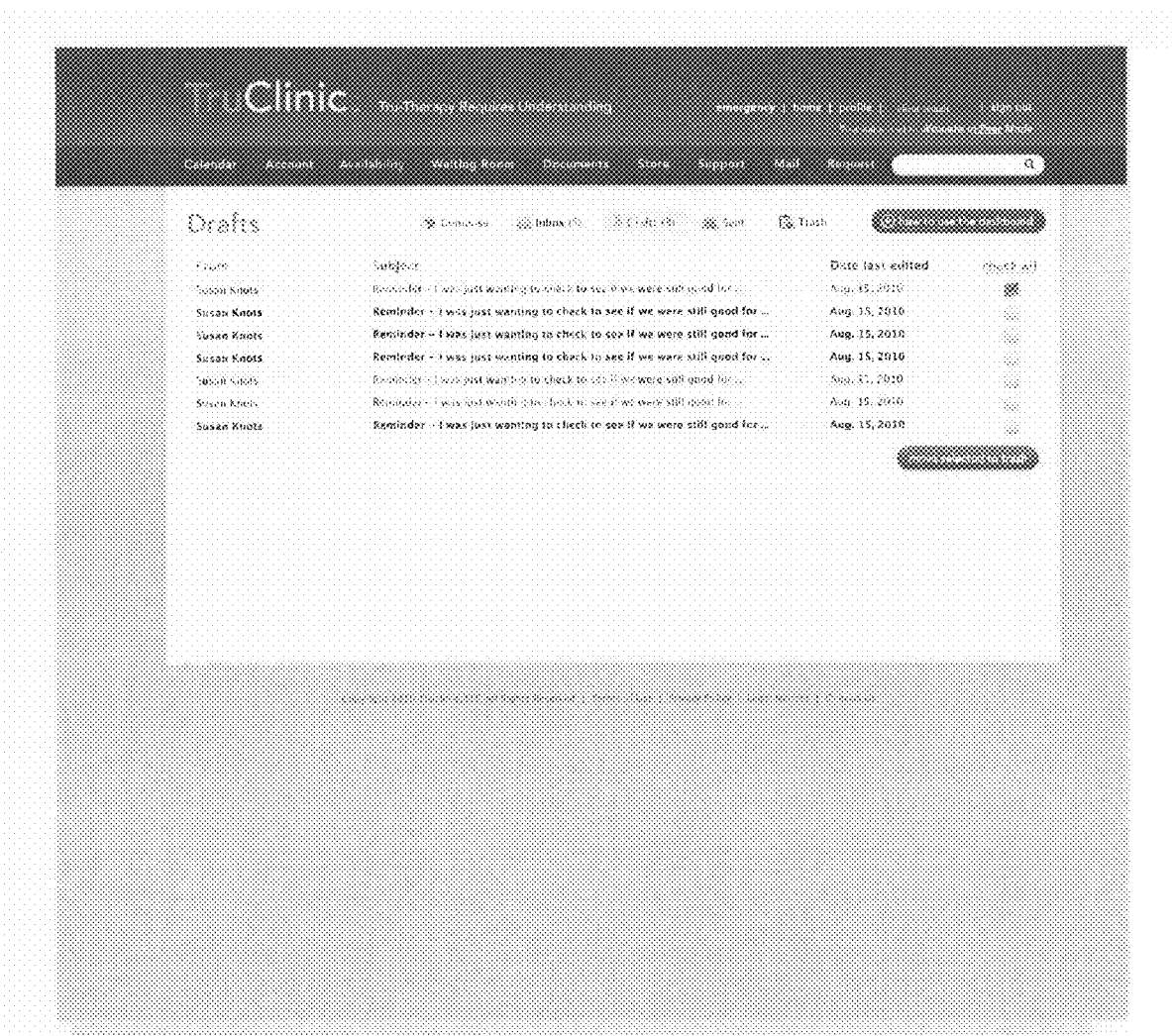
Figure 74:
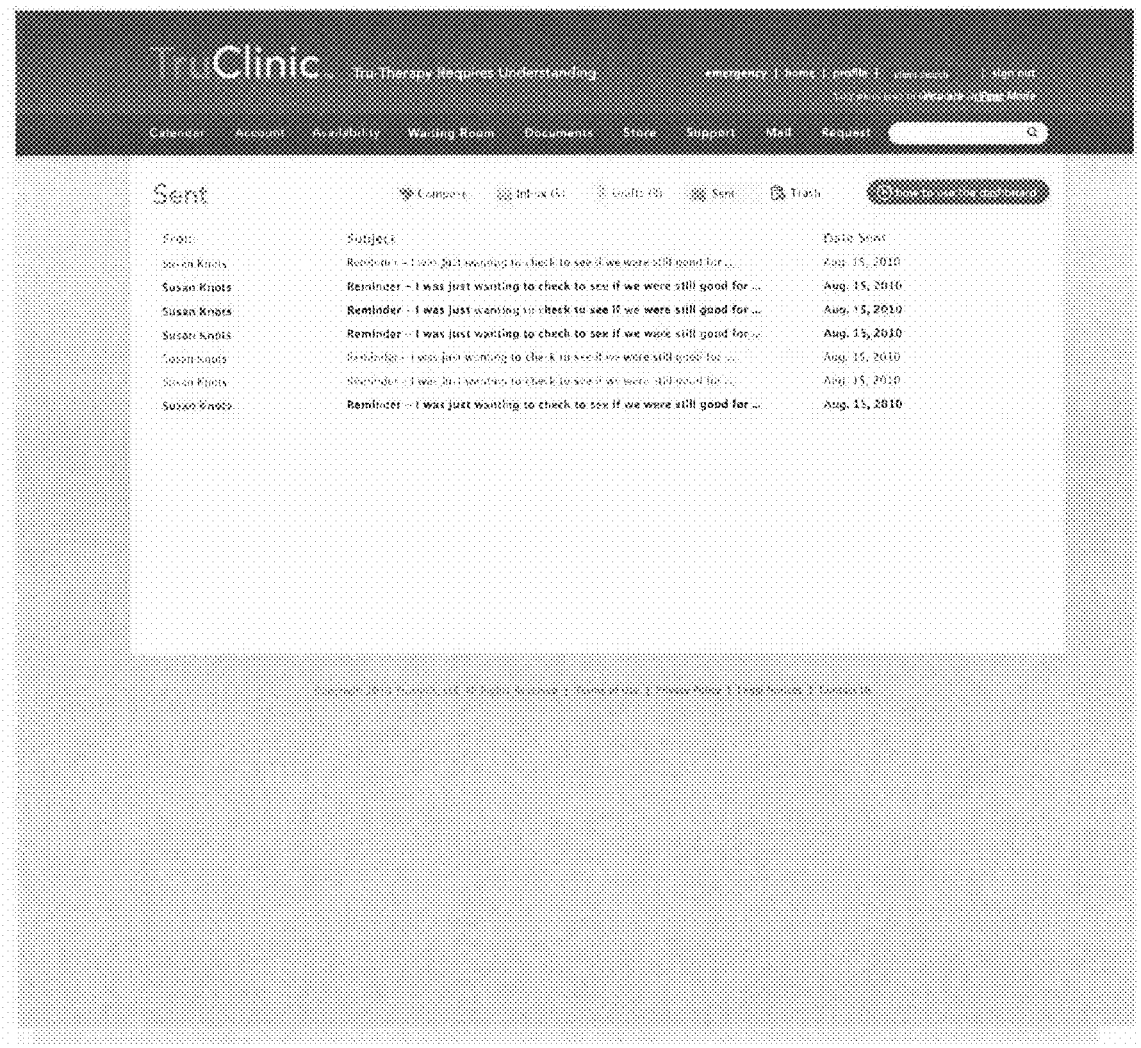
Figure 75:
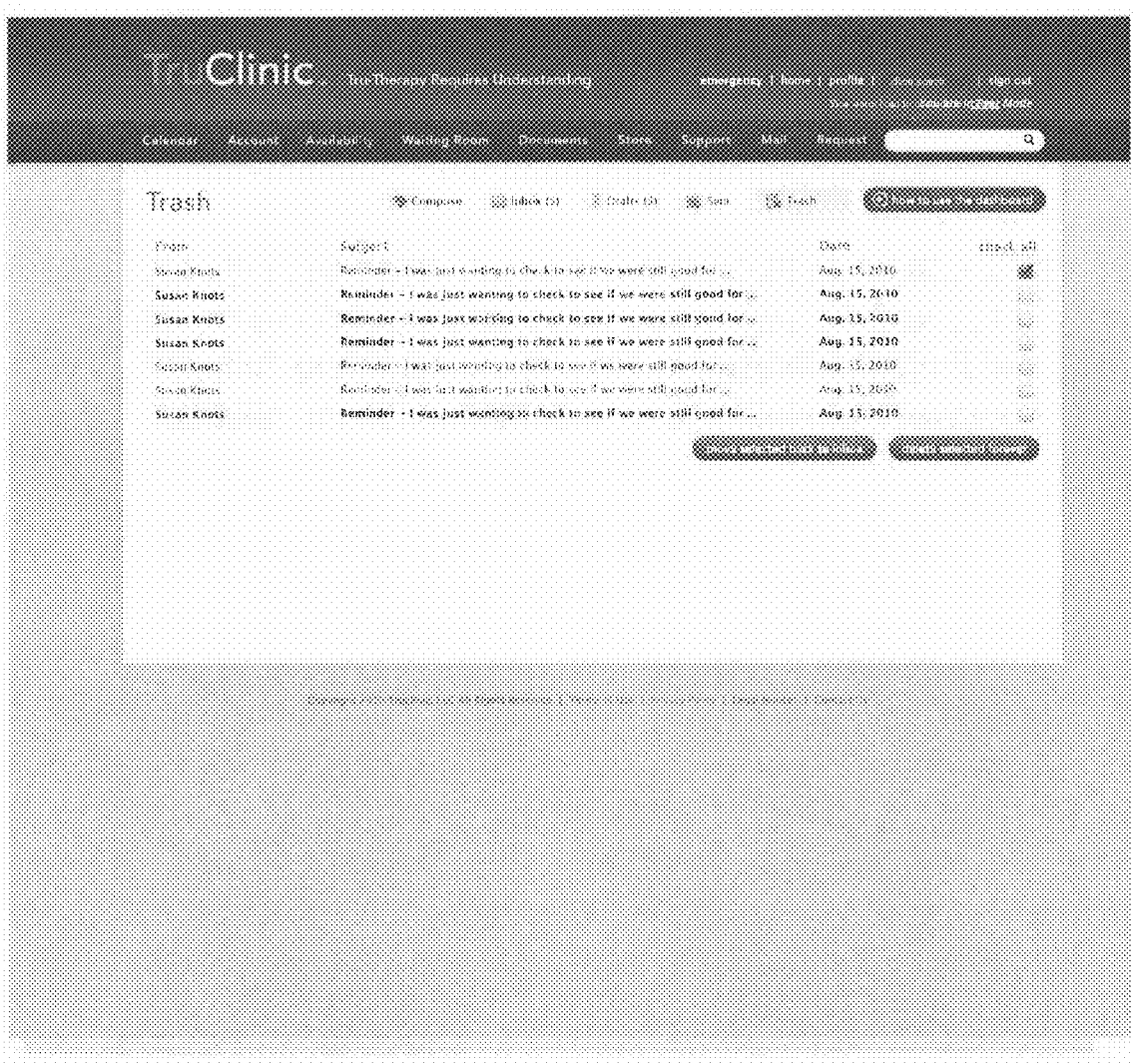
Figure 76:
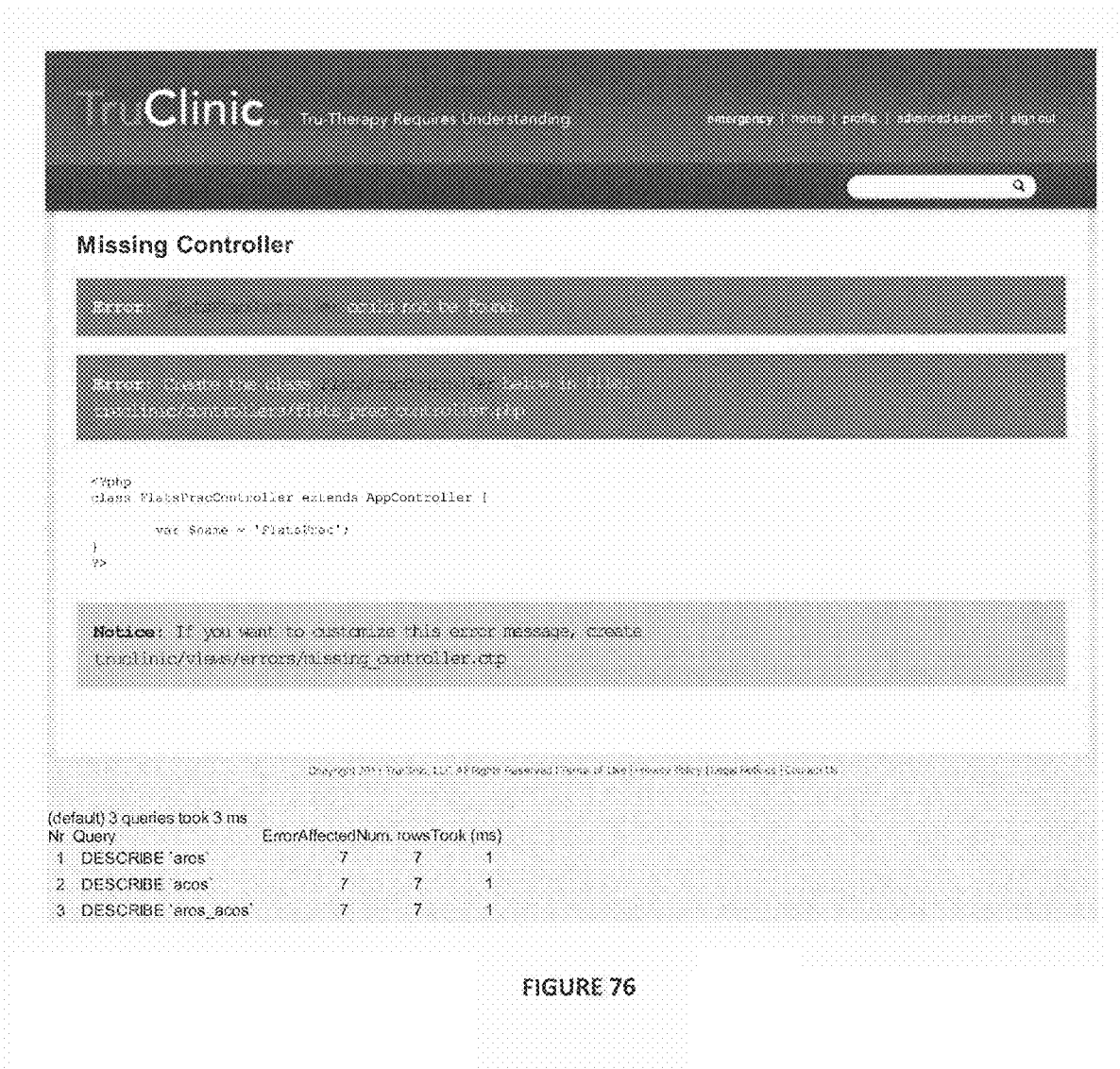
Figure 77:
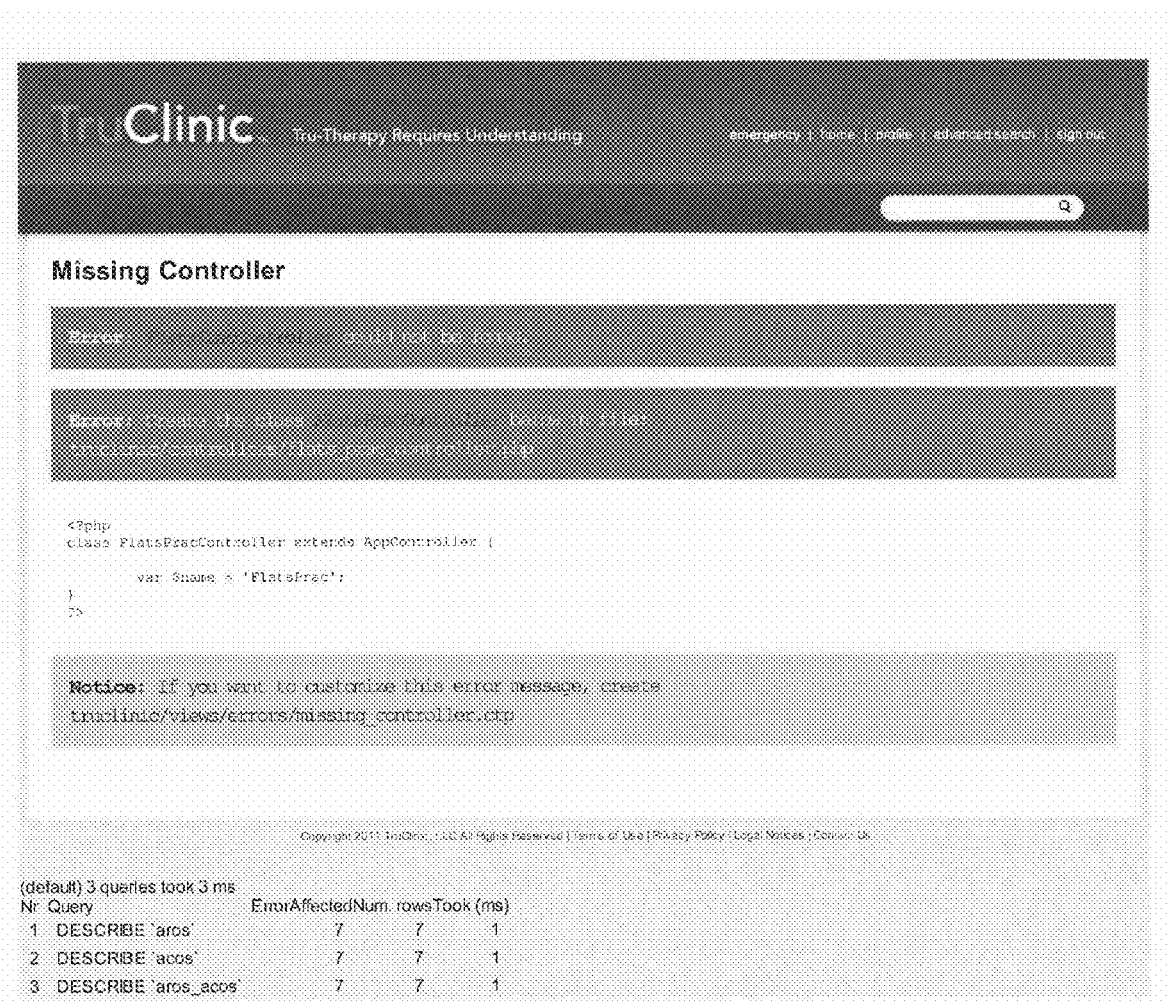

With reference now to FIG. 3, the invention relates generally to methods and systems for conducting counseling sessions. More particularly, the invention relates to methods and systems for counseling sessions and clinics conducted remotely, such as over the Internet and/or via satellite using WIFI as well as other web-based technologies. In addition, the invention relates to methods and systems for conducting remote counseling sessions by means of various mobile devices as well as biofeedback and/or biometric devices configured to interface with an associated network and/or portal to enhance the efficacy and value of the remote counseling sessions.

Accordingly, methods and systems for online counseling sessions conducted over the Internet are disclosed. In some embodiments, a method for remotely conducting counseling sessions between a client and an expert using an IP-based network includes providing a website accessible to the network wherein the expert and a client both have access to the website. In such embodiments, upon accessing and logging into the website, the client is permitted to search a database for online experts and select an appropriate expert for a counseling session. In some embodiments, the client initially completes various intake and/or registration forms in a virtual waiting room, wherein such forms are customized per the relevant expert. The method continues as an expert remotely conducts a counseling session with the client via remote means, including video conferencing. Following the counseling session, the client is automatically returned to the virtual waiting room and provided with subsequent counseling based options.

In some embodiments, the methods of the present invention are directed to expert marketing capabilities and/or strategies. In other embodiments, the methods of the present invention are directed to client scheduling or calendaring for counseling sessions, including synchronization with Outlook™, Gmail™, iCal™ or other electronic and/or web-based calendaring systems or programs. In still other embodiments, email, text, SMS messaging, instant messaging and the like are employed to confirm appointments and/or provide reminders of upcoming appointments, to customize general information presented to individual clients, to secure client access to personalized reports and documentation generated by the expert which, in some embodiments, are accessible to individual client and expert only, to provide access to products for purchase selected by the expert for the client, to provide a full accounting and payment system for experts as well as clients, to facilitate client rating and feedback on the expert relative to services rendered or previously provided, and many other aspects as further disclosed herein.

In some embodiments, the network and associated portal employed or used to practice various embodiments of the invention may further be utilized to provide training or educational services for experts categorized by field, topic, and/or experience level. Accordingly, in various embodiments, the methods and systems of the present invention provide resources for both clients seeking counseling as well as experts seeking additional education or training. In all such embodiments, various forms of electronic communication can be used to supplement online counseling sessions and/or training/education such as on demand products, live webcast products, electronic documents or print products and so forth. Experts seeking to use the systems and methods of the present invention can search for and find additional training and/or educational serves from other experts available through the service in much the same way that clients seeking counseling can find specific experts in a relevant field.

Some embodiments enable clients to access counseling services when and where it is most convenient for them, and increase the flexibility of counseling by offering 24-hour availability for pay-per-minute or other pay-per-view sessions. Some embodiments allow experts in any stage of their practice to provide more support to existing clients and to procure new clients regardless of geographical limitations.

In some embodiments, when scheduling an appointment, a client logs in to the expert's website or other type of Internet portal and accesses a scheduling calendar which displays the available counseling sessions. According to some embodiments, the expert has the ability to alter the calendar so that the view is client dependent. By way of example, in some embodiments the calendar may be manipulated so that fewer "available" counseling sessions are displayed for these clients. In some embodiments, one or more discrete or otherwise independent clinics can also employ the teachings disclosed herein to interface and/or coordinate with one another to simplify inter-office scheduling as well as streamlining other document and/or record keeping as well as a host of services that can be offered to a range of clients. In some embodiments, if an expert finds himself or herself without any clients, e.g., due to cancellations, the inability of clients to travel to the office due to severe weather, etc., that expert can place an "available" icon on the homepage so that clients desiring counseling know that they can have immediate access without consulting the calendar.

In some embodiments, group counseling sessions can be given. In some embodiments, all clients can see the expert and the expert can see all of the clients at the same time on smaller images on one screen. In such embodiments, the expert can assess the demeanor of the clients as they interact. In some embodiments, the clients will be able to see each other and/or hear each other. In some embodiments, online group counseling can be augmented by occasional private conversations. In some further embodiments, the client or the expert may press a button sending an indication that they desire a private conversation, the expert may then excuse himself or herself from the group discussion and engage in a private conversation shielded from the view and hearing of the other group members. In some embodiments, a hold type button (or a type of privacy button) is provided which allows the client to pause or temporarily suspend a particular session or to otherwise provide the client with an opportunity to put the session on hold without actually ending the session. In this way, the client has the ability to interrupt the session with respect to him or herself without affecting the session relative to other uses in order to protect the client's privacy. Specifically, the client has the ability to pause the session on his or her end so that if something in his or her environment changes, the client can control broadcasting such changes to either the expert and/or the other members of the group, or rather has control in order to avoid such a broadcast.

In various embodiments, a "take the floor" feature is offered during a group counseling session. In some embodiments, an expert offers a client the opportunity to lead the discussion by illuminating an icon or reference on the screen in the appropriate location. In some embodiments an "emergency" feature is offered to clients who need emergency contact information for an expert and/or an immediate counseling session with an expert.

In some embodiments, an expert or other practitioner can designate an assistant who has access to the systems of the present invention, including the portal. In some embodiments, for example, an assistant may be a registered nurse or a practitioner's assistant. In such embodiments, the assistant is capable of meeting with and/or pre-screening clients. Such embodiments further contemplate one or more, including multiple, assistants, some of whom work out of different clinics, working with any number of clients for, in connection with or on behalf of a single practitioner. In this way, one practitioner can be affiliated with multiple clinics and provide counseling or other treatment to multiple clients efficiently and effectively. In some embodiments, multiple assistants associated with multiple clinics are associated with multiple practitioners. In such embodiments, the assistants may have limited access to client information to preserve various privacy aspects and in some embodiments the assistants must be licensed in order to provide assistance.

With continued reference to FIG. 3, an online counseling system is provided according to some embodiments from which experts manage their practice, business, clientele, etc., and/or provide counseling to clients. Consistent with such embodiments, such experts or practitioners have online access to the records of their clientele.

In various embodiments, experts use the online counseling system as a means of managing their practice, business, clientele, etc. In some embodiments, experts have the capacity to set the rates they charge for their services. In various embodiments, experts may use the online counseling system to record and/or post a brief video introduction detailing their philosophy and credentials for potential clients to review. In some embodiments, experts can manage their schedules from within the system. In various embodiments, secure billing is a feature of the online counseling system. In some embodiments, experts can easily change their billing rate and create and/or edit a customized web page from the system's control center feature. In some embodiments, the online counseling system provides a number of templates from which experts can select to develop a personalized marketing web page displayed from within the online counseling system.

In some embodiments, practitioners create customized virtual waiting rooms for clients. In some embodiments, experts incorporate multiple waiting rooms for use with specific issues, needs, wants, disorders, etc., as a feature of the system. In some embodiments, the system provides experts with an option to create individual templates for particular clients. In some embodiments, after a session, clients may return to a checkout page where they can purchase products chosen by the expert to appear in their online store. In various embodiments, clients have the ability to prepay for a session, or be billed on a per-minute basis, depending on their particular priority or issue. In some embodiments, experts receive receipts on a regular basis for all transactions, which may include items such as monies received, services billed, fees charged and/or collected, etc. In some embodiments, experts have access to current accounting information, data regarding completed and upcoming sessions, client information, and session notes, laboratory information, medical background, legal history, as well as biometric and/or biofeedback information configured to interface with an associated network and/or portal to enhance the efficacy and value of the remote counseling sessions as well as to authenticate the identity of a given client.

In some embodiments, experts may schedule and/or change client appointments and view their schedule via a calendar interface or other easy-to-use interface. In some embodiments, experts may synchronize their online counseling system calendars with Outlook™, Gmail™, iCal™ and/or other suitable calendaring programs. In further embodiments, experts may also synchronize their online calendars with various mobile or handheld devices, other suitable calendar platforms, and the like. In some embodiments, when a client requests a particular time for a counseling session, the system automatically sends that information to the expert, who may either confirm or deny the appointment. If confirmed, in some embodiments, the appointment is automatically added to the expert's calendar. According to some embodiments, experts can set reminders for upcoming appointments via email, short message service (SMS) (i.e. text message), other alerts, etc. In various embodiments, if a client does not cancel a scheduled appointment within a preset time frame, experts have the option to indicate their availability for per-minute counseling.

Clients using some embodiments of the present invention have access to a number of services and resources, including any combination of: face-to-face meetings, video conferencing, phone sessions, one-on-one email/text chat, avatar chat, group therapy, message board/email/chat, online support groups, self-help tools, assessment instruments, blogs, SMS, social networking sites, personal websites/online journals, audio and/or video recordings, relaxation and meditation programs, biofeedback, biometric devices, testing devices or programs, and/or other communication or counseling technologies.

In some embodiments, the online counseling system is available up to 24 hours a day. In some embodiments, the online counseling system is configured for use with selected experts (including international experts) to ensure 24-hour consultation availability for clients. In other embodiments, licensed assistants may be employed to facilitate 24-hour availability for clients with respect to certain services for which the assistant is qualified.

In some embodiments, experts may choose, or be required, to enter their qualifications, credentials, etc., in order to register for and/or use or otherwise provide services through the online counseling system. In some embodiments, the qualifications, credentials, insurance, degree, work history, licensing information, etc. that is entered by experts may be individually verified through appropriate channels and/or third party sources. For example, in some instances a medical doctor may register with the online counseling system. Thereafter, his or her license to practice medicine may be verified with state health department(s) or other relevant organization(s) to ensure he or she has not been suspended or that his or her license is not otherwise fraudulent or subject to limitations. In various embodiments, an expert is required to maintain licensure requirements, purchase liability insurance, sign indemnity contracts, etc., before using the online counseling system. For example, in some instances a psychotherapist is required to maintain a license in good standing in order to continue to provide counseling via some embodiments of the present invention. In various embodiments, the online counseling system will offer secure, encrypted methods by which the expert and/or the client may enter his or her personal information.

In some embodiments, clients can grade, rate, provide feedback, score, etc., the services they received. For example, in some instances a user is allowed to submit a rating score after they have spent a predetermined amount of time, e.g., at least 5 minutes, 10 minutes, 20 minutes, 30 minutes, 40 minutes, 50 minutes or an hour with an expert. In some embodiments, a certain number of counseling sessions are required before a client is permitted to rate or otherwise score and expert. In some embodiments, clients can search for experts based on their ranking, location, areas of practice, credentials, years of experience, education, and/or other variables.

According to other embodiments, clients can purchase annual memberships allowing them to use features not available to all base-level users. In various embodiments, clients pay to use the online counseling system. For example, in some embodiments, clients pay an annual membership fee. In other embodiments, however, only third party payers who license the portal pay a licensing fee. In some embodiments, the portal will be given to an expert or other general practitioners free of charge. However, in embodiments contemplating additional training or education for experts or other practitioners, experts seeking additional training and/or education may be required to pay fees in connection therewith according to some embodiments. In other embodiments, additional training and/or educational services are provided free of charge to encourage or entice experts to participate further in the system.

In some embodiments, clients pay a fee to the practitioner as well as a fee associated with using the online services of the present invention. In some embodiments, clients pay a percentage of the expert's counseling session fees in order to use the online counseling system. For example, in some embodiments, clients pay 5%, 10%, 15%, 20% or anything between 1% and 20% on top of what the expert charges in order to use the online services of the present invention. For purposes of illustration, and not by way of limitation, if an expert charges a client $40 for an online counseling session, then the client is required to pay $40 to the expert and 10% of the experts fee to the online service. As such, in the foregoing example, the client's total bill is $44. In other embodiments, the percentage collected by the online service may be more or less than 10%. In some embodiments, clients are given a discount or other incentives to begin using the online services.

In various embodiments, advertisers, product manufacturers, private companies, insurance companies, government agencies, or other entities pay money to support the online counseling system, and services are provided to experts and/or users for free or for a reduced price. In various embodiments, experts, clients, and/or other entities can pay for various features, modules, levels, aspects, services, functionalities, etc., of the online counseling system. For example, in some embodiments an expert pays for a monthly fee for a base-level package providing access to most features provided by the online counseling session, and also pays a one-time fee for a pre-designed virtual waiting room for his or her clients. In some embodiments, general practitioners pay a onetime fee. In other embodiments, however, there is no monthly fee for an expert or other general practitioners. Likewise, in other embodiments, there is no onetime fee for experts or other general practitioners. In some embodiments, moreover, third party payers who license the portal pay a licensing fee and provide hosting and/or support for experts and/or practitioners.

In various embodiments, the online counseling system uses secure, encrypted, or otherwise protected methods to exchange data. In various embodiments, the online counseling system includes an on-call system administrator, customer service representatives, or other persons tasked to assist with technical questions and/or handle client or expert inquiries.

In various embodiments, experts have the option to sell any item(s) that they feel might be useful for their client(s). In some embodiments, administrators of the online counseling system collect a percentage, e.g., 5%, 10%, 15%, 20%, 25% 30% or anything between 1% and 30% of the cost of any, or select, products sold by experts through the online counseling system. In some embodiments, experts can determine the shipping and handling costs they wish to charge for items sold to clients within the online counseling system. In some embodiments, sales processing is handled by various service providers, e.g., Google Checkout, PayPal, and other suitable service providers common to those of skill in the art.

In some embodiments, experts can set their own billing rates. For example, in some embodiments the expert chooses to either bill a set amount for prescheduled sessions, and to bill clients on a pay-per-minute (PPM) basis for immediate or emergency services. In various embodiments, online counseling system administrators can set the fees or rates charged to use the service. For example, as mentioned above, in some embodiments, clients pay 5%, 10%, 15%, 20% or anything between 1% and 20% on top of what the expert charges in order to use the online services of the present invention. In other embodiments, the percentage collected by the online service may be more or less than 20%. In various embodiments, experts are responsible for their own taxes. In various embodiments, online counseling system administrators charge a fee for tax withholding and other services. In such embodiments, provisions of tax withholding and other services are explained in a terms and conditions document provided to experts during registration with the online counseling system.

In some embodiments, the online counseling system sends the fees for completed sessions to experts on a daily, weekly, bi-monthly, monthly, semi-annually and/or annual basis via wire transfer, less the amount collected in connection with use of the online services, i.e. the percentage on top of what the expert charges for use of the online services, such as 5%, 10%, 15%, 20% or anything between 1% and 20% as discussed previously. In some embodiments, additional fees collected for services and product sales are also sent to experts on a daily, weekly, bi-monthly, monthly, semi-annually and/or annual basis less the cost of any higher-level services for which experts may opt or any additional percentages which are owed to the online service. In some embodiments, practitioners can change their options at any time. When such options are changed, in some embodiments, the billing is prorated when settings are changed in the middle of a billing cycle. In some embodiments, experts can view their account for the past year of services at any time and/or download digital invoices.

In some embodiments, practitioners can designate in advance the times that they are available for prescheduled sessions. In various embodiments, practitioners can designate their availability for per-minute services. In some embodiments, experts can access a calendar maintained on their computer allowing them to enter prescheduled appointments or designate their per-minute availability. In various embodiments, the expert's calendar can be synced with their profile to indicate available remaining slots. In some embodiments, experts can choose the view that the public sees of their calendar. For example, in some embodiments the expert chooses to show only currently available slots. In some embodiments, clients can submit a request to a particular expert for a specified time slot. In such embodiments, the request is automatically forwarded to the desired expert or to an assistant designated to assist the expert with respect to the individual client or a group of clients wherein the assistant can confirm or deny the appointment. In some embodiments, if a request for an appointment is confirmed, it automatically schedules a counseling session on the expert's calendar and/or creates automated reminders for the parties involved. In some embodiments, any party can change the frequency of reminders they receive for a particular appointment and/or for all appointments. In some embodiments, if the expert denies a request for an appointment, the client is notified and is given the opportunity to request a different proposed time for a counseling session.

In some embodiments, experts can conduct individual sessions via web cam and/or act as a moderator for group sessions. In various embodiments, groups counseling sessions can consist of one, two, three, four, five, six, seven, eight, nine, ten, eleven, twelve, thirteen, fourteen, fifteen, sixteen, seventeen, eighteen, nineteen, twenty, or more clients. It is contemplated that group sessions can consist of as many clients as the technology used by the online counseling system allows. In some embodiments, the online counseling system incorporates functionality that allows experts to have digital zoom, enhancement, volume, analysis, or other features or capabilities that assist in evaluating clients' body language and/or state of mind.

However, as mentioned above, in some embodiments, a hold type button (or a type of privacy button) is provided which allows the client to pause or temporarily suspend a particular session or to otherwise provide the client with an opportunity to put the session on hold without actually ending the session. In this way, the client has the ability to interrupt the session with respect to him or herself without affecting the session relative to other uses in order to protect the client's privacy. Specifically, the client has the ability to pause the session on his or her end so that if something in his or her environment changes, the client can control broadcasting such changes to either the expert and/or the other members of the group, or rather has control in order to avoid such a broadcast.

In some embodiments, any client and/or expert can record any portion of group counseling sessions (with the exception of control afforded to individual client participants in connection with the privacy button discussed previously). In various embodiments, recordings are downloaded directly to the recording party's computer, and/or are stored remotely on the online counseling sessions' hardware, and/or are stored on a third-party's hardware. In some embodiments, as discussed with reference to FIGS. 1 and 2, cloud-based architectures are contemplated. In such embodiments, recordings or other data stored in connection with any given counseling session may also, or alternatively be stored on the cloud. In some embodiments, storage is held on the cloud be default. In some embodiments, group counseling sessions involving multiple individuals in separate locations are not recordable by client(s). In some embodiments, group counseling sessions are recordable only by expert(s).

In various embodiments, calendaring tools are used to facilitate scheduling counseling sessions. In various embodiments, buttons and/or other interface objects providing calendaring options are presented to the client and/or the expert that assist them in scheduling counseling sessions. In some embodiments, experts are given access to a "View Affected" button, a "View Conditions" button, a "Restrictions" button, or something similarly entitled, which permits an expert to view and/or place restrictions on clients' ability to view and/or schedule appointments. In some embodiments, access is given to experts through the use of such buttons, or similarly titled buttons, which permit the expert to modify or otherwise alter certain components of client information, including in some embodiments personal information, as well. For example, in some embodiments an expert can limit the client to one session per day, per week, etc., so as to prevent a client from needlessly over-scheduling counseling sessions. In some embodiments, the expert can restrict a client from viewing and/or scheduling counseling sessions during specific times or dates. For example, in some embodiments a client who has insurance that pays a set fee or a low fee can be restricted to view and/or schedule only off-peak hours or dates.

In other embodiments, when an expert is unable to be on-time for a counseling session, the expert can press the "View Affected" button, or something similarly titled, permitting the expert to see which counseling sessions are affected and providing options regarding what can be done to reschedule the affected counseling sessions. In various embodiments, clients are given access to an "Emergency" button, a "Get Help Now" button, a "Hotline" button, or something similarly entitled, which permits a client to receive counseling immediately. In some embodiments, pressing the "Emergency" button, or similarly entitled button, sends an alert to available experts. In such embodiments, an expert may confirm the alert and begin a counseling session with the client who indicated they were in emergent need. In various embodiments, clients are given access to a "See Immediate" button, a "See Available" button, or something similarly entitled, which allows clients to view and/or schedule counseling sessions with experts who are currently available, regardless of whether or not there is emergent need.

In various embodiments, dynamic tools are used to improve counseling sessions. In various embodiments, buttons and/or other interface objects providing dynamic abilities to mute, start, stop, enhance, emphasize, record, remove, re-organize, delay, pause, forward, rewind, and/or other dynamic abilities, are presented to the client and/or the expert that improve the ability to provide psychiatric care during the counseling sessions. For example, in some embodiments the expert uses a "Privacy" button, a "Go Private" button, or other something similarly entitled, to speak, text, or otherwise communicate in private with a subset of clients during a group counseling session. In some embodiments, the effect would be to reduce or mute the audio, text, video capabilities, and/or restrict other forms of communication for the group member(s) who were not invited to speak in private. In other embodiments, similarly entitled buttons are available to a client to temporarily pause a given counseling session so as to preserve his or her privacy if the environment he or she is in during the session changes and the client prefers not to broadcast his or her environment for a period of time without ending the session altogether. In such embodiments, the remaining members of the session (i.e. experts and/or other clients) are permitted to continue with the session in progress. In some embodiments, the use of a dynamic tool has the effect of reducing or muting what the clients can type, hear, see, and/or restrict other forms of communication. In some embodiments, the use of a dynamic tool has the effect of playing a predetermined text, audio track, video clip, and/or other communicative presentation.

In some embodiments, the expert and/or client has access to a "Take the Floor" button, an "I Hold the Conch" button, or something similarly entitled, that allows only a subset of clients to "take the floor," i.e., speak, type, or otherwise communicate during a group counseling session without allowing others to speak, type, or otherwise communicate. In some embodiments, only the expert has the power to grant the ability to take the floor. In some embodiments, the client has to request permission from the expert and/or group before being able to take the floor. In some embodiments, the client is allowed to take the floor only for a set amount of time; in other embodiments, the client may receive the right to take the floor for the full length of the counseling session. In some embodiments, the person(s) who have taken the floor are emphasized by some text, audio, or visual indication. For example, in some embodiments a group counseling session that has both audio and video feeds in which taking the floor has the effect of increasing that client's volume and chat window size, while reducing the other clients' volume and chat window size. In some embodiments, for example, a digital zoom function is provided to facilitate the emphasis of the individual taking the floor.

In some embodiments, when a client requests a specific expert for a pay-per-minute session, and the expert does not connect with the client for a session within a set time period, the client has the option to send an email requesting that the expert provide information about their next available time slot. In some embodiments, clients can be redirected to a page listing alternative experts currently online that meet the client's desired criteria.

In some embodiments, an online counseling system allows experts to design or import documents they deem necessary for services provided to their clients. In some embodiments, files created by experts for a particular client can be downloaded to the expert's computer and/or the client's computer. In alternative embodiments, such files and/or documents are made available in real time via cloud architecture as discussed with reference to FIGS. 1 and 2. In various embodiments, the online counseling system enables experts to integrate various client records with information from other sources. For example, in some embodiments, records generated during online counseling sessions can be integrated with psychotherapy records obtained from a third-party. In various embodiments, the process of generating records or other files and/or documents during an online counseling session are created via an application integration utility (AIU).

In various embodiments, the online counseling system is used for more than individualized and/or group counseling sessions, but is also used for training programs and educational sessions. For example, in some embodiments an online counseling system is used to teach mental health classes, pre-nuptial classes, birthing classes, shaken-baby training, anger-control training, language training, etc. In other embodiments, various educational and/or training programs are provided with respect to specific fields of study in which students are provided with supervised opportunities to practice or apply certain teachings commensurate with learning such information or shortly thereafter. In other words, some embodiments contemplate the provision of hands-on experience with certain educational features or subjects or otherwise contemplate the provision of a practicum which enables students to apply theoretical knowledge contemporaneously with the acquisition of such knowledge.

In various embodiments, the online counseling system is used by experts fluent in various different languages. For example, in some embodiments refugees are taught English classes by an expert who speaks their native language which facilitates the language instruction. In another non-limiting example, in some embodiments a deaf individual may receive psychotherapy treatment using a videoconferencing feature of the online counseling system from an expert psychologist who speaks American Sign Language. In other embodiments, for example, certain clients are able to access therapy in connection with diverse topics, such as shaken baby syndrome and prevention of the same. In such embodiments, such therapy, counseling and/or educational information is provided in the first language of the client in order to maximize the efficacy of such sessions.

In other embodiments, counseling and/or educational sessions are also available via video counseling and associated technologies for incarcerated persons, such as people in jail, prison, mental institutions and other formats where clients are unable or precluded from leaving a given facility but yet have access to Internet or web-based services. In such embodiments, counseling and/or education could be provided as a means of treating incarcerated individuals or other persons with mental or emotional challenges.

Various embodiments that use the online counseling system described herein to provide counseling sessions are called "TruClinic." For example, in some embodiments psychotherapy services are provided through an online counseling system called TruClinic. Some embodiments of TruClinic include a control center for experts to change any aspect of their marketing information and billing rate. Some embodiments of TruClinic include a billing matrix/payment management system that allows experts to charge whatever they choose, with a preset minimum, such as the non-limiting example in which an expert charges $1.00 per minute with a $25.00 minimum. In other embodiments, there is no minimum charge; rather clients are permitted to access the system and participate in a session on a pay-per-minute basis while being allowed to terminate the session at any time without incurring a minimum charge. In this way, clients are not discouraged from trying the services for fear of incurring a minimum charge.

Some embodiments of TruClinic include a module that allows experts to record a brief introduction of themselves, as well as an overview of the services they provide. Some embodiments of TruClinic include a digital or virtual waiting room for which experts can set up various wallpapers or backgrounds depending on the client they are seeing. For example, in some embodiments the expert is working with someone that has post-traumatic stress disorder, and can utilize a pre-made or customized virtual waiting room populated with questionnaires, articles, videos, and particular products for sale, such as books about the disorder. In some embodiments of TruClinic, such features may be managed from the expert's control center within the online counseling system.

Some embodiments of TruClinic include regularly and/or immediately updated accounting and statistical information regarding the expert's practice. Some embodiments of TruClinic may include a scheduling and client management system that will remind clients and/or experts of appointments via email, text message, a computer alarm, social networking such as Facebook, Twitter, as well as SMS, instant messaging, etc. In some embodiments of TruClinic experts can synchronize their calendar with various calendar programs as discussed previously.

Some embodiments of TruClinic include a module that allows experts to record a session (starting at any point during the session) without TruClinic maintaining any records of client/expert appointments or interactions. Embodiments of TruClinic are fully compliant with all internet protocols, security standards, confidentiality standards, or other requirements imposed on experts of businesses in various fields. For example, in some embodiments some embodiments of TruClinic that provide medical and/or psychotherapeutic counseling services are fully compliant with the confidentiality and record-keeping standards imposed by the Health Insurance Portability and Accountability Act of 1996 ("HIPAA"). In addition, embodiments of TruClinic are fully compliant with standards propagated, established, maintained and/or enforced by Health Level Seven International, the American Medical Association, the American Psychological Association, and Assessment & Treatment Alternatives clinic among other health oriented organizations with regard to the interoperability of health information technology and associated protocols.

Some embodiments of TruClinic include allowing experts from the United States, and/or experts from countries with similar standard-of-care modalities as those in the United States to use TruClinic to provide online counseling services. In such embodiments, internationally-based experts are required to meet United States standards related to medical records, information, confidentiality, etc. For example, in some embodiments experts from Great Britain, Germany, New Zealand, Ireland, Scotland, Australia, France, Japan, and Canada are eligible to register and/or use such embodiments of TruClinic because psychotherapy experts in those countries are required to meet standards comparable to those imposed here in the United States. The foregoing list of countries that may be permitted to register and/or use various embodiments of TruClinic is merely illustrative and may be reduced, supplemented, augmented or otherwise modified according to various embodiment of the present invention.

The embodiments of online counseling systems provided herein provide many advantages. Various embodiments ensure privacy and confidentiality assuring clients they can express themselves freely, which assists in the provision of effective counseling. Various embodiments assist individuals to receive counseling at critical times. Because of their worldwide reach, flexible scheduling, and/or 24-hour availability, various embodiments make effective counseling available at convenient times and places, and/or at a price that is sustainable for many clients. For example, such embodiments can provide important counseling for veterans, military personnel, indigent, home-bound, in jail, or other persons who cannot or are too far away to travel to a traditional brick-and-mortar building to receive counseling, etc. In various embodiments, because the technology is able to simulate real-time, in-person interactions, experts can provide the same kind of services they would be able to provide were they to meet the client in-person, but do so in a manner that allows the client to meet in a space of their choosing that is comfortable for them, making them more likely to be at ease during the therapy session, thus increasing the likelihood of effective communication and effective therapy.

In various embodiments, the use of virtual or "digital" waiting rooms help to put clients at ease and enable the expert to further replicate the experience of in-person interactions. In various embodiments, if a client cancels his or her counseling session, experts can use the flexible scheduling features to recoup time that would have otherwise been lost in a solely brick-and-mortar practice. In various embodiments, the ranking and feedback feature(s) provide clients with the ability to assess and experiment with experts and to locate the expert(s) that perfectly meet their needs on an immediate and/or long-term basis.

Some embodiments of the present invention minimize or eliminate much of the overhead associated with running a traditional therapy office, e.g., such as rent, fees, utilities, and staff. Some embodiments of the invention enable experts to provide effective services to clients in any location, thus increasing their potential client base and referral pool to a worldwide scale. Some embodiments of the invention also enable experts to work the hours they prefer, since clients can be in any time zone. Some embodiments of the present invention create new client and service opportunities for experts. Some embodiments of the present invention allow experts who are just starting their businesses to have a viable and economical alternative to the high-cost structure of joining a group of other experts to start building a client base. Some embodiments allow experts with an established practice to expand their reach by offering existing clients the option to use online consultations to supplement regularly scheduled in-person appointments. Some embodiments allow experts looking to scale back their practice for such reasons as imminent retirement to continue to provide high-quality services to select long-standing clients without the expense and stress associated with maintaining a physical office environment.

In some embodiments of the present invention, entrance codes can be provided to allow clients to enter a waiting room. For example, when scheduling an appointment, a client can be provided an entrance code that will allow him to enter the waiting room at an appropriate time. In some embodiments, the expert or an administrator of the system can deactivate an entrance code to prevent the client from using it to enter the waiting room. Also, in some embodiments, after a client has used an entrance code to enter a waiting room, the expert or other administrator can remove the client from the waiting room without deactivating the entrance code used by the client to enter the waiting room. In this way, the client can reenter the waiting room using the same entrance code at a later time.

In some embodiments of the present invention, anonymous entrance codes can be employed to allow a client to anonymously enter an expert's waiting room to conduct an anonymous counseling session. For example, the expert may email or otherwise transmit anonymous entrance codes to clients.

The present invention can be used by experts to provide counseling sessions in many different medial fields including but not limited to: Addiction Medicine, Adolescent & Young Adult Medicine, Allergy/Immunology, Anatomic Pathology & Laboratory Medicine, Anesthesiology, Blood Banking/Transfusion Medicine, Body Imaging, Cardiology, Chemical Pathology, Child/Adolescent Neurology, Child/Adolescent Psychiatry, Clinical Cardiac Electrophysiology, Critical Care Medicine, Cytopathology, Dermatology, Dermatopathology, Diagnostic Radiology, Diagnostic Roentgenology, Diagnostic Ultrasound, Emergency Medical Services, Emergency Medicine, Facial Plastic Surgery, Family Medicine and OMT, Family Physicians, Female Pelvic Medicine/Reconstructive Surgery, Forensic Pathology, Gastroenterology, General Vascular Surgery, Geriatric Medicine, Geriatric Psychiatry, Gynecologic Oncology, Hand Surgery, Hematology, Hematology-Pathology, Home Health, Hospice, Hospice and Palliative Medicine, Immunopathology, In Vivo and In Vitro Nuclear Medicine, Infectious Disease, Internal Medicine, Interventional Cardiology, Laboratory Medicine, Maternal and Fetal Medicine, Medical Microbiology, Medical Toxicology, MOHS-Micrographic Surgery, Nephrology, Neurological Surgery, Neurology, Neuromusculoskeletal Medicine & OMM, Neuropathology, Neurophysiology, Neuroradiology, Nuclear Cardiology, Nuclear Imaging and Therapy, Nuclear Medicine, Nuclear Radiology, Obstetrics & Gynecology, Obstetrics & Gynecology Surgery, Occupational Medicine, Oncology, Ophthalmology, Orthopedic Surgery, Otolaryngic Allergy, Otolaryngology, Otolaryngology/Facial Plastic Surgery, Pain Management, Pain Medicine, Palliative Medicine, Pediatric Endocrinology, Pediatric Pulmonology, Pediatric Radiology, Pediatrics, Physical Medicine & Rehabilitation, Plastic & Reconstructive Surgery, Preventive Medicine, Preventive Medicine/Aerospace Medicine, Preventive Medicine/Occupational, Preventive Medicine/Occupational-Environmental Medicine, Preventive Medicine/Public Health, Proctology, Psychiatry, Radiation Oncology, Radiation Therapy, Radiology, Reproductive Endocrinology, Rheumatology, Roentgenology, Sleep Medicine, Sports Medicine, Surgical Critical Care, Thoracic Cardiovascular Surgery, Undersea and Hyperbaric Medicine, Urological Surgery, and Vascular & Interventional Radiology.

The present invention can also be used by experts to provide counseling sessions in many different surgical sub-specialties including but not limited to: Amputations, Bariatrics, Cardiac Surgery, Endocrine Surgery, Eye Surgery, General Surgery, Gynecological Surgery, Neurosurgery, Oral and maxillofacial surgery, Orthopedic surgery, Otolaryngology, Plastic Surgery, Proctology, Surgical Oncology, Thoracic Surgery, Trauma surgery, Urology, Vascular surgery, Abdominal Surgery, Cardiothoracic surgery, Dental Surgery, Endoscopic Endonasal surgery, Neurointerventional surgery, Orthognathic surgery, Pediatric surgery, Shoulder surgery, and Urogynecology.

The present invention can also be used by experts to provide counseling sessions in many different nursing sub-specialties including but not limited to: Ambulatory care nursing, Advanced practice nursing, Burn nursing, Camp nursing, Cardiac nursing, Cardiac catheter laboratory nursing, Medical case management, Community health nursing, Correctional nursing, Critical care nursing, Emergency and trauma nursing, Environmental health nursing, Faith community nursing, Flight nursing, Forensic nursing, Gastroenterology nursing, Genetics nursing, Geriatric nursing, Health visiting, Holistic nursing, Home health nursing, Hospice and palliative care nursing, Hyperbaric nursing, Immunology and allergy nursing, Intellectual disability nursing, Intravenous therapy nursing, Infection control nursing, Infectious disease nursing, Legal nursing, Learning disability nursing, Maternal-child nursing, Medical-surgical nursing, Mental health or psychiatric nursing, Military and uniformed services nursing, Neonatal nursing, Neurosurgical nursing, Nursing informatics, Nursing management, Nursing research, Nursing midwife, Obstetrical nursing, Occupational health nursing, Oncology nursing, Orthopaedic nursing, Ostomy nursing, Pediatric nursing, Perianesthesia nursing, Perioperative nursing, Private duty nursing, Psychiatric or mental health nursing, Public health nursing, Pulmonary nursing, Quality improvement, Radiology nursing, Rehabilitation nursing, Renal nursing, School nursing, Space nursing, Sub-acute nursing, Substance abuse nursing, Surgical nursing, Telenursing, Telephone triage nursing, Transplantation nursing, Travel nursing, Urology nursing, Utilization management, and Wound care.

The present invention can also be used by experts to provide counseling sessions in many different mental health specialties/sub-specialties including but not limited to: Abuse, Academic, Addictions, Adjustment, Adolescents, Adoption, Adults, AIDS/HIV, Alcohol Abuse, Alzheimer's/Dementia, Anxiety/Panic, Attention Deficit Hyperactivity, Autism Spectrum, Behavioral Issues, Behavioral Medicine, Bipolar, Borderline Personality Disorder, Brain Injury (TBI), Business Consultation, Cancer/Terminal Illness, Caregiver Support, Child, Child Abuse, Children of Alcoholics, Children of Mentally Ill, Chronic Pain or Illness, Clinical, Codependency, Compulsive Gambling, Conduct Disorder, Consultation—Liaison, Cultural Issues, Cyberbullying, Deaf/Hard of Hearing Issues, Depression, Developmental Disorders, Diabetic, Disability, Disaster Intervention & Recovery, Dissociative, Divorce/Custody, Domestic Violence, Drug Abuse, Dual Diagnosis, Eating Disorders, Elder Abuse, Elder/Geriatric, Executive/Career/Life Coaching, Family Issues, Forensic, Gender Identity Concerns, Grief, Holistic, Hospital, Impulse Control, Individuals, Infants, Infertility, Integrative Medicine, Internet Addiction, Intimacy Issues, Learning Disabilities, Legal Issues, Life Transitions, Marital Counseling, Mediation/Collaboration, Medication, Mens Issues, Mental Conditions, Mental Deficiency, Military Issues, Mood Disorders, Narcissistic, Neuropsychiatry, Neuropsychology, Obesity, Obsessive Compulsive, Occupational Psychiatry, Oppositional Defiant, Organizational Psychology, Other, Parenting Issues/Training, Personality Disorders, Phobias, Pornography addiction, Post Traumatic Stress Disorder/PTSD, Postpartum, Psychological Educational Consultations, Psychological Testing, Psychological Trauma, Psychosomatic, Relationship Issues, Reproductive, Schizophrenia/Psychosism, Self-Esteem Issuesm, Self-Harm/Suicide, Sexual Harassment, Sexual Issues, Sleep/Insomnia, Spiritual Concerns, Sports Psychology, Stalking, Stress Management, Telepsychiatry/Telemedicine, Violent Offenders, Womens Issues, Work Issues, and Workers Compensation.

The present invention may also be used by experts to provide counseling sessions in many different veterinarian fields including but not limited to: Alternative medicine, Anaesthesiology, Animal behavior, Animal welfare, Birds (pet and ornamental), Bovine, Canine, Cardiology, Chiropractic, Clinical pathology, Clinical pharmacology, Dentistry, Dermatology, Diagnostic imaging, Equine, Emergency and critical care, Exotics, Feline, Internal medicine, Laboratory animal medicine, Microbiology, Neurology, Nutrition, Oncology, Ophthalmology, Parasitology, Pathology, Poultry, Preventive medicine, Radiology, Reptile and amphibian, Shelter medicine, State veterinary medicine, Sports medicine, Surgery, Theriogenology, Toxicology, Veterinary Surgery, and Zoo animals and wildlife.

The present invention may also be used by experts to provide counseling sessions in many different legal fields including but not limited to: Administrative law, Admiralty law, Advertising law, Agency law, Alcohol law, Alternative dispute resolution, Animal law, Antitrust law, Appellate practice, Art law, Aviation law, Banking law, Bankruptcy law, Bioethics, Bird law, Business law, Business organizations law, Class action litigation/Mass tort litigation, Communications law, Computer law, Conflict of law (or private international law), Constitutional law, Construction law, Consumer law, Contract law, Copyright law, Corporate law (or company law), Corporate compliance law and corporate governance law, Criminal law, Cryptography law, Cultural property law, Custom law, Cyber law, Defamation, Derivatives and futures law, Drug control law, Elder law, Employee benefits law (ERISA), Employment law, Energy law, Entertainment law, Environmental law, Equipment finance law, Evidence, Family law, FDA law, Financial services regulation law, Firearm law, Food law, Franchise law, Gaming law, Health law, Health and safety law, Health care law, Immigration law, Insurance law, Intellectual property law, International law, International trade and finance law, Internet law, Labor law, Land use & zoning law, Litigation, Martial law, Media law, Mergers and acquisitions law, Military law, Mining law, Juvenile law, Music law, Mutual funds law, Nationality law, Native American law, Obscenity law, Oil & gas law, Parliamentary law, Patent law, Poverty law, Privacy law, Private equity law, Private funds law/Hedge funds law, Procedural law, Product liability litigation, Property law, Public health law, Railroad law, Real estate law, Securities law/Capital markets law, Social Security disability law, Space law, Sports law, Statutory law, Tax law, Technology law, Timber law, Tort law, Trademark law, Transport law/Transportation law, Trusts & estates law, Utilities Regulation, Venture capital law, and Water law.

The present invention may also be used by experts to provide counseling sessions in many different dental fields including but not limited to: Dental Public Health, Endodontics, Oral and Maxillofacial Pathology, Oral and Maxillofacial Radiology, Oral and Maxillofacial Surgery, Orthodontics and Dentofacial Orthopedics, Pediatric Dentistry, Periodontics, and Prosthodontics.

The present invention may also be used by experts to provide counseling sessions in many other fields including but not limited to: Art, Music, Computers, Electronics, Cooking, Fashion & Beauty, Fitness, Nutrition, Home & Garden, and Health & Wellness.

While the foregoing advantages of the present invention are manifested in the detailed description and illustrated embodiments of the invention, a variety of changes can be made to the configuration, design and construction of the invention to achieve those advantages. Hence, reference herein to specific details of the structure and function of the present invention is by way of example only and not by way of limitation.

Accordingly, the present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed is:

1. A method for remotely conducting counseling sessions between a client and an expert via a website, the method comprising:

providing a website by which a client can interact with an expert, the website including a first virtual waiting room for the expert;

receiving, via the website, a request from a client that selects the expert for a therapy session;

identifying one or more attributes of the client;

customizing the first virtual waiting room based on at least one of the one or more attributes of the client; and conducting, via the website, a counseling session between the expert and the client.

2. The method according to claim 1, wherein the one or more attributes of the client include one or more of:

an identity of the client;

a known need of the client;

a disorder of the client;

a questionnaire related to a condition of the client;

an article related to a condition of the client;

a video related to a condition of the client; or a product for sale related to a condition of the client.

3. The method of claim 1, wherein the one or more attributes comprise one or more of an issue of a client, a need of a client, a want of a client, or a disorder of a client.

4. The method of claim 1, wherein the one or more attributes of the client are identified prior to receiving the request from the client that selects the expert for a therapy session.

5. The method of claim 1, wherein the one or more attributes of the client are identified using one or more questionnaires or intake forms filed out by the client by interacting with the website.

6. The method of claim 1, wherein customizing the first virtual waiting room comprises customizing a wallpaper or background of the first virtual waiting room.

7. The method of claim 1, wherein the one or more attributes of the client includes a condition of the client, and customizing the first virtual waiting room comprises populating the first virtual waiting room with one or more questionnaires, articles, videos, products, or books related to the condition of the client.

8. The method of claim 1, further comprising:

receiving, via the first virtual waiting room, client input that completes an intake or registration form while the client waits in the first virtual waiting room.

9. The method of claim 1, further comprising:

after conducting the counseling session, updating the website to again display the first virtual waiting room to the client.

10. The method of claim 9, wherein, when the first virtual waiting room is again displayed, the first virtual waiting room is displayed with one or more items that the expert has recommended for the client based on the counseling session.

11. The method of claim 9, further comprising:

when the first virtual waiting room is again displayed, providing, within the first virtual waiting room, an option for the client to schedule another counseling session with the expert.

12. The method of claim 1, wherein conducting, via the website, a counseling session between the expert and the client comprises providing videoconferencing between the expert and the client via the website.

13. The method of claim 1, further comprising:

receiving, via the website and from the expert, one or more of:

time available for pre-booked sessions with established clients;

time available for pay-per-minute sessions with established clients;

time available for pre-booked sessions with public clients; and time available for pay-per-minute sessions with public clients.

14. The method of claim 1, wherein the counseling session is also between the expert and at least one other client.

15. The method of claim 14, wherein the counseling session comprises a videoconference, the method further comprising:

receiving input from the expert that controls who is viewable and audible in the videoconference and which of the clients has the floor to speak in the videoconference.

16. The method of claim 1, further comprising:

providing, via the website, an option for the client to enter the first virtual waiting room without having scheduled an appointment with the expert.

17. The method of claim 1, further comprising:

displaying, via the website, information regarding a previous counseling session conducted between the client and the expert.

18. A method for remotely conducting counseling sessions between a client and an expert via a website, the method comprising:

providing a website by which a client can interact with an expert, the website including a first virtual waiting room for the expert;

receiving, via the website, a request from a client that selects the expert for a therapy session;

identifying a condition of the client;

customizing the first virtual waiting room based on the condition of the client; and conducting, via the website, a counseling session between the expert and the client.

19. The method of claim 18, wherein customizing the first virtual waiting room comprises customizing one or more forms displayed within the first virtual waiting room.

20. The method of claim 18, wherein identifying a condition of the client comprises identifying a want, need, issue, or disorder of the client.

\* \* \* \* \*